US007749700B2

(12) United States Patent
Baird et al.

(10) Patent No.: US 7,749,700 B2
(45) Date of Patent: Jul. 6, 2010

(54) DIFFERENTIAL EXPRESSION OF MOLECULES ASSOCIATED WITH ACUTE STROKE

(75) Inventors: Alison E. Baird, Brooklyn, NY (US); David F. Moore, Rockville, MD (US); Ehud Goldin, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 500 days.

(21) Appl. No.: 11/155,835

(22) Filed: Jun. 17, 2005

(65) Prior Publication Data

US 2006/0046259 A1 Mar. 2, 2006

Related U.S. Application Data

(63) Continuation-in-part of application No. PCT/US2005/018744, filed on May 27, 2005.

(60) Provisional application No. 60/575,279, filed on May 27, 2004.

(51) Int. Cl.
*C12Q 1/68* (2006.01)
*C12M 1/34* (2006.01)

(52) U.S. Cl. .................. 435/6; 435/287.1

(58) Field of Classification Search .................. None
See application file for complete search history.

(56) References Cited

U.S. PATENT DOCUMENTS

| 6,183,752 | B1 | 2/2001 | Epstein et al. |
| 6,486,299 | B1 | 11/2002 | Shimkets |
| 2002/0172958 | A1 | 11/2002 | Gonzalez-Zulueta et al. |
| 2003/0013649 | A1 | 1/2003 | Rosen et al. |
| 2003/0055019 | A1 | 3/2003 | Shimkets |
| 2004/0005577 | A1 | 1/2004 | Rosen et al. |
| 2005/0054570 | A1 | 3/2005 | Rosen et al. |

FOREIGN PATENT DOCUMENTS

| EP | 1347063 A1 | 9/2003 |
| WO | WO 03/008647 A2 | 1/2003 |

OTHER PUBLICATIONS

Teasseli. Canadian Family Physician, vol. 38, pp. 381-382, 385-388, Feb. 1992.*
Cheung et al (2003) Nature Genetics, vol. 33, pp. 422-425.*
Wu (2001) Journal of Pathology 195:53-65.*
Newton et al (2001) Journal of Computational Biology, vol. 8, No. 1, pp. 37-52.*
Affymetrix. Expression Probe Set Details. 215049_x_at. Accessed from https://www.affymetrix.com/analysis/netaffx/fullrecord.affx?pk=HG-U133A%3A215049_X_AT, on Oct. 6, 2009. three pages.*

"Affimetrix GeneChip Human Genome U133 Array Set HG-U133A," GEO, Mar. 11, 2002, XP002254749.
Lynch et al., "Novel Diagnostic Test for Acute Stroke," *Stroke* 35:57-63 (2004).
Miklos et al., "Microarray Reality Checks in the Context of a Complex Disease," *Nature Biotechnol.* 22:615-621 (2004).
Baird, "Blood Genomics in Human Stroke," *Stroke* 38:694-698, 2007.
Sharp et al., "Genomic Profiles of Stroke in Blood," *Stroke* 38:691-693, 2007.
Tang et al., "Gene Expression in Blood Changes Rapidly in Neutrophils and Monocytes after Ischemic Stroke in Humans: a Microarray Study," *J. Cereb. Blood Flow Metab.* 26:1089-1102, 2006.
Kim et al., "DNA Array Reveals Altered Gene Expression in Response to Focal Cerebral Ischemia," *Brain Res. Bull.* 58:491-498 (2002).
Kostulas et al., "Ischemic Stroke is Associated with a Systemic Increase of Blood Mononuclear Cells Expressing Interleukin-8 mRNA," *Stroke* 29:462-466 (1998).
Lu et al., "Genomics of the Periinfarction Cortex After Focal Cerebral Ischemia," *J. Cereb. Blood Flow Metab.* 23:786-810 (2003).
Moore et al., "Genetic Fingerprint of Acute Ischemic Stroke," *Ann. Neurol.* 54:S24 (2003).
Moore et al., "Using Peripheral Blood Mononuclear Cells to Determine a Gene Expression Profile of Acute Aschemic Stroke; a Pilot Investigation," *Circulation* 111:212-221 (2005).
Schmidt-Kastner et al., "DNA Microarray Analysis of Cortical Gene Expression During Early Recirculation After Focal Brain Ischemia in Rat," *Mol. Brain Res.* 108:81-93 (2002).
Schwarz et al., "Identification of Differentially Expressed Genes Induced by Transient Ischemic Stroke," *Mol. Brain Res.* 101:12-22 (2002).

(Continued)

*Primary Examiner*—Juliet C Switzer
(74) *Attorney, Agent, or Firm*—Klarquist Sparkman, LLP

(57) ABSTRACT

Methods are provided for evaluating a stroke, for example for determining whether a subject has had an ischemic stroke, determining the severity or likely neurological recovery of a subject who has had an ischemic stroke, and determining a treatment regimen for a subject who has had an ischemic stroke, as are arrays and kits that can be used to practice the methods. In particular examples, the method includes screening for expression in ischemic stroke related genes (or proteins), such as white blood cell activation and differentiation genes (or proteins), genes (or proteins) related to hypoxia, genes (or proteins) involved in vascular repair, and genes (or proteins) related to a specific peripheral blood mononuclear cell (PBMC) response to the altered cerebral microenvironment. Also provided are methods of identifying one or more agents that alter the activity (such as the expression) of an ischemic stroke-related molecule.

11 Claims, 1 Drawing Sheet

OTHER PUBLICATIONS

Soriano et al., "Parallel Gene Expression Monitoring Using Oligonucleotide Probe Arrays of Multiple Transcripts with an Animal Model of Focal Ischemia," *J. Cereb. Blood Flow Metab.* 20:1045-1055 (2000).

Steffens et al., "Low Dose Oral Cannabinoid Therapy Reduces Progression of Atherosclerosis in Mice," *Nature* 434:782-786 (2005).

Tang et al., "Blood Genomic Responses Differ After Stroke, Seizures, Hypoglycemia, and Hypoxia: Blood Genomic Fingerprints of Disease," *Ann. Neurol.* 50:699-707 (2001).

Tang et al., "Genomic Responses of the Brain to Ischemic Stroke, Intracerebral Haemorrhage, Kainate Seizures, Hypoglycemia, and Hypoxia," *Eur. J. Neurosci.* 15:1937-1952 (2002).

Tang et al., "Blood Genomic Expression Profile for Neuronal Injury," *J. Cereb. Blood Flow Metab.* 23:310-319 (2003).

* cited by examiner

DIFFERENTIAL EXPRESSION OF MOLECULES ASSOCIATED WITH ACUTE STROKE

CROSS REFERENCE TO RELATED APPLICATIONS

This is a continuation-in-part of PCT/US2005/018744 filed May 27, 2005, which claims priority to U.S. Provisional Application No. 60/575,279 filed May 27, 2004, all herein incorporated by reference in their entirety.

FIELD

This application relates to methods of evaluating an ischemic stroke, methods of identifying a treatment modality for a subject who has had an ischemic stroke, methods of identifying compounds that alter the activity of an ischemic stroke-related molecule, as well as arrays and kits that can be used to practice the disclosed methods.

BACKGROUND

Stroke is the third leading cause of death and the leading cause of adult disability in developed countries (Simons et al., *Stroke* 29:1341-6, 1998; Adams et al., *Ischemic Cerebrovascular Disease*. New York: Oxford, 2001). Strokes are caused by an interruption of blood flow to the brain, by either an intravascular occlusion (such as an arterial thrombus) or a hemorrhage. The American Heart Association estimates that there are approximately three million stroke survivors in the United States, most of whom are disabled. Despite the prevalence and burden of this disease, stroke precipitants and pathophysiological mechanisms in individual patients are often unknown. It is also difficult to accurately predict whether a stroke will lead to only minor neurological sequelae or more serious medical consequences.

Gene expression profiling involves the study of mRNA levels in a tissue sample to determine the expression levels of genes that are expressed or transcribed from genomic DNA. Animal experiments in focally ischemic brain tissue have indicated that there are alterations in gene expression following a stroke (Stenzel-Poore et al., *Lancet* 362:1028-37, 2003; Lu et al., *J. Cereb. Blood Flow. Metab.* 23:786-810, 2003; Tang et al., *Eur J Neurosci* 15:1937-52, 2002; Tang et al., *Ann. Neurol.* 50:699-707, 2001; and Tang et al., *J Cereb Blood Flow Metab* 23:310-9, 2003). However, gene expression profiling has not yet been applied to clinical human stroke, primarily because brain tissue samples are inaccessible and rarely justified. Therefore, an assay that can allow one to determine the genetic expression profile of ischemic stroke without the need for brain tissue samples is needed.

Currently, there is no specific blood marker of acute stroke. Following a stroke, released brain antigens can be detected in the blood. Such antigens include S100B, neuron specific enolase (NSE), and glial fibrillary acid protein (GFAP), although S100B and GFAP are of low sensitivity for early stroke diagnosis, and NSE and myelin basic protein (MBP) MBP are non-specific (Lamers et al., *Brain. Res. Bull.* 61:2614, 2003). Four soluble factors that have demonstrated moderate sensitivity and specificity for the diagnosis of stroke include two markers of inflammation (matrix metalloproteinase-9 and vascular cell adhesion molecule), one marker of glial activation (S100beta) and one thrombosis marker (von Willebrand factor) (Lynch et al., *Stroke* 35:57-63, 2004). However, a panel of markers which allow one to diagnose and prognose ischemic stroke with high diagnostic sensitivity and specificity is still needed.

SUMMARY

Although stroke is one of the leading causes of morbidity and mortality in developed countries, methods for rapidly and accurately determining whether a subject has had a stroke are expensive and invasive. Therefore, new methods are needed for evaluating a stroke, for example for determining whether an ischemic stroke has occurred, for determining the severity of the stroke or the likely neurological recovery of the subject who had an ischemic stroke, or combinations thereof. In particular examples, the disclosed methods offer a potentially lower cost alternative to expensive imaging modalities (such as MRI and CT scans), can be used in instances where those imaging modalities are not available (such as in field hospitals), and can be more convenient than placing individuals in scanners (for example for subjects who can not be subjected to MRI, such as those having certain types of metallic implants in their bodies).

Using these methods, appropriate therapy protocols for subjects who have had an ischemic stroke can be identified and administered. For example, because the results of the disclosed methods are highly reliable predictors of the ischemic nature of the stroke, the results can also be used (alone or in combination with other clinical evidence and brain scans) to determine whether thrombolytic therapy designed to lyse a neurovascular occlusion such as a thrombus (for example by using tissue plasminogen activator or streptokinase) should be administered to the subject. In certain examples, thrombolytic therapy is given to the subject once the results of the differential expression assay are known if the assay provides an indication that the stroke is ischemic in nature.

The inventors have identified changes in gene expression in peripheral blood mononuclear cells (PBMCs) that allow one to evaluate a stroke, for example to determine whether a subject has had an ischemic stroke, to determine the severity of an ischemic stroke, to determine the likely neurological recovery of the subject, or combinations thereof. The disclosed methods allow one to screen many genes simultaneously and serially and only a relatively small amount of cell or tissue sample is needed. Changes in gene expression were observed in at least 22 genes, at least 82 genes, at least 190 genes, or even at least 637 genes depending on sensitivity and specificity used. In particular examples, subjects who had an ischemic stroke showed increased gene expression in CD163; hypothetical protein FLJ22662 Laminin A motif, bone marrow stromal cell antigen 1 (BST-1, also known as CD157); Fc fragment of IgG, high affinity Ia, receptor for (FcγRI, also known as CD64); baculoviral IAP repeat-containing protein 1 (also referred to in the literature as neuronal apoptosis inhibitory protein); or KIAA0146, or any combinations thereof, such as a change in expression in at least 1, at least 2, at least 3, at least 4, at least 5, or all 6 of these genes. In some examples, subjects who had an ischemic stroke showed increased gene expression in four classes of genes: genes involved in white blood cell activation and differentiation, genes related to hypoxia, genes involved in vascular repair, and genes related to a PBMC response to the altered cerebral microenvironment.

The disclosed gene expression fingerprint of ischemic stroke enables methods of evaluating a stroke, for example determining whether a subject had an ischemic stroke, determining the prognosis of a subject who had an ischemic stroke, as well as determining an appropriate treatment regimen for a subject who had an ischemic stroke. In some examples, the disclosed methods are at least 78% sensitive and at least 80% specific for identifying those subjects who have suffered an ischemic stroke, for example within the past 72 hours. In other examples, the disclosed methods are at least 80% sensitive (such as at least 85% sensitive or at least 90% sensitive) and at least 80% specific (such as at least 85% specific or at least 90% specific) for identifying those subjects who have suffered an ischemic stroke, for example within the past 72 hours. In particular examples, the disclosed methods are at least 80% sensitive for predicting the likelihood of neurological recovery of the subject.

In some examples, the method involves detecting patterns of increased protein expression, decreased protein expression, or both. Such patterns of expression can be detected either at the nucleic acid level (such as quantitation of mRNAs associated with protein expression) or the protein level (such as quantitative spectroscopic detection of proteins). Certain methods involve not only detection of patterns of expression, but detection of the magnitude of expression (increased, decreased, or both), wherein such patterns are associated with the subject having had an ischemic stroke, or is associated with predicted clinical sequelae, such as neurological recovery following an ischemic stroke.

The disclosed methods are the first that permit accurate diagnosis of an ischemic stroke using PBMCs with high sensitivity and specificity. PBMCs infiltrate the evolving cerebral infarct as part of the tissue remodeling process. Release of brain antigens from damaged neural cells may allow sensitization of PBMCs followed by changes in functional gene expression.

The disclosed methods can be performed on a subject who is suspected of having had a stroke, for example prior to radiographic investigation. In another example, the method is performed on a subject known to have had a stroke, as the disclosed assays permit early and accurate stratification of risk of long-lasting neurological impairment.

In one example, the method of evaluating a stroke includes determining whether a subject has changes in expression in four or more ischemic stroke-associated molecules that comprise, consist essentially of, or consist of, sequences (such as a DNA, RNA or protein sequence) involved in white blood cell activation and differentiation, sequences related to hypoxia, sequences involved in vascular repair, and sequences related to a PBMC response to the altered cerebral microenvironment, such as those listed in Table 5.

In other examples, ischemic stroke-associated molecules comprise, consist essentially of, or consist of, CD163; hypothetical protein FLJ22662 Laminin A motif; BST-1; FcγRI; baculoviral IAP repeat-containing protein 1; and KIAA0146, or any 1, 2, 3, 4, 5, or 6 of these molecules. For example, ischemic stroke-associated molecules can comprise, consist essentially of, or consist of, 4 or more, such as 5 or more, 10 or more, 20 or more, 22 or more, 50 or more, 75 or more, 80 or more, 82 or more, 100 or more, 150 or more, 190 or more, 200 or more, 300 or more, 500 or more, 600 or more, or 637 or more of the nucleic acid or protein sequences listed in Tables 2-5. Any of the identified sequences can be used in combination with such sets or subsets of sequences.

In a particular example, evaluating a stroke includes detecting differential expression in at least four ischemic stroke-related molecules of the subject, such as any combination of at least four genes (or the corresponding proteins) listed in any of Tables 2-5, wherein the presence of differential expression of at least four ischemic-stroke related molecules indicates that the subject has had an ischemic stroke. Therefore, such methods can be used to diagnose an ischemic stroke. In particular examples, the at least four ischemic-stroke related molecules include at least one of CD163; hypothetical protein FLJ22662 Laminin A motif; BST-1; FcγRI; baculoviral IAP repeat-containing protein 1; or KIAA0146, such as at least 2, at least 3, at least 4, at least 5 or at least 6 of such molecules. For example, the method can include determining if the subject has increased gene (or protein) expression of at least one of CD163; hypothetical protein FLJ22662 Laminin A motif; BST-1; FcγRI; baculoviral IAP repeat-containing protein 1; or KIAA0146, optionally in combination with determining if the subject has altered gene (or protein) expression of any other combination of other ischemic stroke-associated molecules, such as any combination of at least 3 other genes (for example any combination of at least 5, at least 10, at least 20, at least 50, at least 100, at least 200, or even at least 500 genes) listed in Tables 2-5.

In a particular example, differential expression is detected by determining if the subject has increased gene (or protein) expression of at least one of CD163; hypothetical protein FLJ22662 Laminin A motif; BST-1; FcγRI; baculoviral IAP repeat-containing protein 1; or KIAA0146, and determining if the subject has decreased gene (or protein) expression of at least one of intercellular adhesion molecule 2, protein kinase D2, GATA binding protein 3, hypothetical protein FLJ20257, or protein kinase C, theta. For example, differential expression can be detected by determining if the subject has increased gene (or protein) expression of CD163; hypothetical protein FLJ22662 Laminin A motif; BST-1; FcγRI; baculoviral IAP repeat-containing protein 1; and KIAA0146, and determining if the subject has decreased gene (or protein) expression of intercellular adhesion molecule 2, protein kinase D2, GATA binding protein 3, hypothetical protein FLJ20257, and protein kinase C, theta.

In one example, the method includes determining if the subject has an increase in gene expression in any combination of at least four of the genes listed in Table 5, for example an increase in at least 5, at least 10, at least 15, at least 20, or at least 22 of the genes listed in Table 5. An increase in expression in any combination of four or more of the genes listed in Table 5 (or the corresponding proteins), and particularly any combination of at least one gene (or protein) from each of the four classes of genes listed in Table 5 (such as any combination of at least 2 or at least 3 sequences from each of the four classes of genes listed in Table 5) indicates that the subject has had an ischemic stroke. Any one of the set of genes (or proteins) can be identified by a single one or the genes (or proteins) listed in Table 5. Any one of the genes (or proteins) in Table 5 can be combined with any other combination of the genes (or proteins) in Table 5 to produce a combination or subcombination of genes (or proteins).

In one example, the method of evaluating a stroke includes determining if the subject has a change in gene expression (such as an increase or decrease) in any combination of at least 150 of the 190 of the genes listed in Table 3, for example a change in expression in at least 160, at least 170, at least 175, at least 180, or at least 185 of the genes listed in Table 3. Any one of the set of genes can be identified by a single one or the genes listed in Table 3. Any one of the genes (or proteins) in Table 3 can be combined with any other combination of the genes (or proteins) in Table 3 to produce a combination or subcombination of genes. A change in expression in any combination of 150 or more of the genes listed in Table 3 (or the corresponding proteins) indicates that the subject has had an ischemic stroke.

In another example, the method of evaluating a stroke includes determining if the subject has a change in gene expression (such as an increase or decrease) in any combination of at least 510 of the 637 of the genes listed in Table 2, for example an increase or decrease in any combination of at least 510, at least 550, at least 575, at least 600, at least 620, or at least 630 of the genes listed in Table 2. Any one of the set of genes (or proteins) can be identified by a single one or the genes (or proteins) listed in Table 2. Any one of the genes (or proteins) in Table 2 can be combined with any other combination of the genes (or proteins) in Table 2 to produce a combination or subcombination of genes. A change in expression in any combination of 510 or more of the genes listed in Table 2 (or the corresponding proteins) indicates that the subject has had an ischemic stroke.

In some examples, the amount of gene (or protein) expression in the subject is compared to a control, such as the gene (or protein) expression of a subject who has not had an ischemic stroke, wherein an increase or decrease in expression in any combination of four or more ischemic stroke related genes listed in Tables 2-5 compared to the control indicates that the subject has experienced an ischemic stroke. For example, an increase in expression in any combination of four or more ischemic stroke related genes (or the corresponding proteins) listed in Table 5, such as at least one gene (or the corresponding protein) from each class listed in Table 5, compared to the control indicates that the subject has experienced an ischemic stroke.

In particular examples evaluating the stroke includes predicting a likelihood of severity of neurological sequelae of the ischemic stroke. In some examples, evaluating the stroke includes predicting a likelihood of neurological recovery of the subject. For example, if there is differential expression (such as increased expression) in at least the 22 ischemic-stroke related molecules listed in Table 5, indicates that the subject has a higher risk of long-term adverse neurological sequelae and therefore a lower likelihood of neurological recovery. In another example, detecting a change in expression in any combination of 150 or more of the genes listed in Table 2 or 3 (or the corresponding proteins) indicates that the subject has a higher risk of long-term adverse neurological sequelae and therefore a lower likelihood of neurological recovery. In yet another example, detecting a change in expression in any combination of at least 500 of the 637 of the genes listed in Table 2, for example an increase or decrease in any combination of at least 510, at least 550, at least 575, at least 600, at least 620, or at least 630 of the genes listed in Table 2 indicates that the subject has a higher risk of long-term adverse neurological sequelae and therefore a lower likelihood of neurological recovery. In some examples, differential expression in the subject is compared to differential expression of a subject who has not had an ischemic stroke, wherein a change in expression in at least the 22 ischemic-stroke related molecules listed in Table 5, such as any combination of 150 or more of the genes listed in Tables 2 or 3 (or the corresponding proteins) compared to the control indicates that the subject has a higher risk of long-term adverse neurological sequelae and therefore a lower likelihood of neurological recovery.

The disclosed methods can further include administering to a subject a treatment to avoid or reduce ischemic injury if the presence of differential expression indicates that the subject has had an ischemic stroke. For example, a change in expression in at least four ischemic stroke related molecules, such as a combination that includes at least four of the molecules listed in Tables 2-5, indicates that the subject has had an ischemic stroke (and not a hemorrhagic stroke) and is in need of thrombolytic therapy (such as t-PA or heparin), anticoagulant therapy (such as coumadin), or combinations thereof. Therefore, the disclosed methods differentiate ischemic from hemorrhagic stroke, and allow one to administer the appropriate therapy to the subject. In some examples, the amount of differential expression in the subject is compared to the expression of a subject who has not had an ischemic stroke, wherein a change in expression in at least four ischemic stroke related molecules listed in Table 2-5 (or the corresponding proteins), such as at least those 22 listed in Table 5, compared to the control indicates that the subject would benefit from thrombolytic therapy, anticoagulant therapy, or combinations thereof.

In some examples the presence of differential expression is evaluated by determining a t-statistic value that indicates whether a gene or protein is up- or down-regulated. For example, an absolute t-statistic value can be determined. In some examples, a negative t-statistic indicates that the gene or protein is downregulated, while a positive t-statistic indicates that the gene or protein is upregulated. In particular examples, a t-statistic less than −3 indicates that the gene or protein is downregulated, such as less than −3.5, less than −3.6, less than −3.7 or even less than −3.8, while a t-statistic of at least 3, such as at least 3.5, at least 3.7, or at least 3.8 indicates that the gene or protein is upregulated.

Differential expression can be detected at any time following the onset of clinical signs and symptoms that indicate a potential stroke, such as within 24 hours, within 7-14 days, or within 90 days of onset of clinical signs and symptoms that indicate a potential stroke. Examples of such signs and symptoms include, but are not limited to: headache, sensory loss (such as numbness, particularly confined to one side of the body or face), paralysis (such as hemiparesis), pupillary changes, blindness (including bilateral blindness), ataxia, memory impairment, dysarthria, somnolence, and other effects on the central nervous system recognized by those of skill in the art.

In particular examples, the disclosed methods include isolating nucleic acid molecules from PBMCs of a subject suspected of having had an ischemic stroke (or known to have had an ischemic stroke), such as mRNA molecules. The isolated nucleic acid molecules are contacted with or applied to an array, for example an array that includes oligonucleotide probes capable of hybridizing to ischemic stroke-associated genes. In another particular example, the disclosed methods include purifying proteins from PBMCs of a subject suspected of having had an ischemic stroke (or known to have had an ischemic stroke). The isolated proteins are contacted with or applied to an array, for example an array that includes antibody probes capable of hybridizing to ischemic stroke-associated proteins. In some examples, PBMCs are obtained within at least the previous 72 hours of a time when the stroke is suspected of occurring, such as within the previous 24 hours.

Also provided herein are arrays that include molecules that permit evaluation of a stroke. Such arrays in particular examples permit quantitation of ischemic stroke-related nucleic acid or protein sequences present in a sample, such as a sample that includes PBMC nucleic acid molecules or proteins.

In one example, the array includes oligonucleotide probes capable of hybridizing to nucleic acid molecules (such as gene, cDNA or mRNA sequences) involved in white blood cell activation and differentiation, nucleic acid molecules related to hypoxia, nucleic acid molecules involved in vascular repair, and nucleic acid molecules related to a PBMC response to the altered cerebral microenvironment, such as at least those listed in Table 5. Examples of particular genes are provided in Tables 2-5. In particular examples, the array includes probes that recognize any combination of at least 4 of the genes listed in any of Tables 2-5, for example at least 10, at least 20, at least 50, at least 100, at least 150, at least 160, at least 170, at least 175, at least 180, at least 185, at least 200, at least 400, at least 500, at least 510, at least 550, at least 575, at least 600, at least 620, or at least 630 of the genes listed in any of Tables 2-5. For example, the array can include oligonucleotide probes capable of hybridizing to a sequence that encodes at least CD163; hypothetical protein FLJ22662 Laminin A motif; BST-1; FcγRI; baculoviral IAP repeat-containing protein 1; and KIAA0146, or any one of these. In one example, the array includes oligonucleotide probes capable of hybridizing to a sequence that encodes one or more of CD163; hypothetical protein FLJ22662 Laminin A motif; BST-1; FcγRI; baculoviral IAP repeat-containing protein 1; or KIAA0146, such as at least 2, at least 3, at least 4, at least 5 or at least 6 of such molecules. In some examples, the array includes probes that recognize any combination of at least one gene from each of the four classes listed in Table 5, such as at least 2, at least 3, at least 5, or at least 10 genes from each class.

The isolated nucleic acid molecules are incubated with the array for a time sufficient to allow hybridization between the isolated nucleic acid molecules and oligonucleotide probes, thereby forming isolated nucleic acid molecules:oligonucleotide probe complexes. The isolated nucleic acid molecules: oligonucleotide probe complexes are then analyzed to determine if there are changes in gene expression (such as increases or decreases), for example changes in expression of any combination of four or more of the genes listed in Table 5, such as 20 or more of the genes listed in Tables 2-5, or such as 150 or more of the genes listed in Tables 24. In particular examples, changes in gene expression are quantitated. The presence of increased expression of four or more genes listed in Tables 2-5 with a positive t-statistic value, or decreased expression of four or more genes listed in Tables 24 with a negative t-statistic value (or any combination thereof, such as decreased expression of at least one gene and increased expression of at least 3 genes listed in Tables 24), after multiple comparison correction, indicates that the subject has had an ischemic stroke.

In another example, the method includes isolating proteins from PBMCs of a subject suspected of having had an ischemic stroke, or known to have had an ischemic stroke. In particular examples the assay is performed on substantially purified or isolated PBMCs that have been separated, for example, for other leukocytes in the blood. The isolated proteins are contacted with or applied to an array.

Arrays that can be used to detect and quantitate proteins for evaluating stroke are also provided. For examples, the array, such as a protein-binding array, can include probes (such as an oligonucleotide probes or antibodies) capable of hybridizing to ischemic-stroke related proteins, such as proteins involved in white blood cell activation and differentiation, proteins related to hypoxia, proteins involved in vascular repair, and proteins related to a PBMC response to the altered cerebral microenvironment. Examples of particular ischemic-stroke related proteins are provided in Tables 2-5. The isolated proteins are incubated with the array for a time sufficient to allow hybridization between the proteins and probes on the array, thereby forming protein:probe complexes.

The protein:probe complexes are then analyzed and in some examples quantitated to determine if there are changes in gene expression (such as increases or decreases) in any combination of four or more of the molecules listed in any of Tables 2-5, such as changes in expression of one or more of CD163; hypothetical protein FLJ22662 Laminin A motif; BST-1; FcγRI; baculoviral IAP repeat-containing protein 1; and KIAA0146, or 2, 3, 4, or 5 of these. In a specific example, protein:probe complexes are analyzed (for example quanti- tated) to determine if there are increases in expression in any combination of at least one protein from each of the four classes listed in Table 5, such as at least 2, at least 3, at least 5, or at least 10 genes from each of the classes listed in Table 5. The presence of increased or decreased expression of any combination of four or more proteins listed in Tables 24 (or increased expression of any combination of four or more proteins listed in Table 5), indicates that the subject has had an ischemic stroke.

In particular examples, the disclosed arrays are capable of evaluating a stroke, for example for determining whether a subject has had an ischemic stroke, determining the severity of the ischemic stroke, determining the likelihood of neurological recovery of a subject who had an ischemic stroke, determining how to treat a subject who had an ischemic stroke, or combinations thereof. Such arrays include oligonucleotides that are complementary to ischemic stroke-related genes, such as those involved in white blood cell activation and differentiation, genes related to hypoxia, genes involved in vascular repair, and genes related to a PBMC response to the altered cerebral microenvironment. Examples of particular genes are provided in Tables 2-5. Kits including such arrays are also disclosed.

In one example, proteins a biological sample are quantitated, for instance by quantitative mass spectroscopy, to determine whether proteins associated with ischemic stroke or prognosis of ischemic stroke are upregulated, downregulated, or both.

Also provided in the present disclosure are methods of identifying one or more agents that alter the activity (such as the expression) of an ischemic stroke-related molecule (for example a gene or protein), such as one or more of those listed in Tables 2-5. If desired, multiple test agents and multiple ischemic stroke-related molecules can be screened at the same time. In one example, the method is used to screen the effect of one test agent on multiple ischemic stroke-related molecules simultaneously (such as all of the ischemic stroke-related molecules listed in Table 2 or Table 3). In another example, the method is used to screen the effect of multiple test agents on one ischemic stroke-related molecule, such as one of the molecules listed in Tables 2-5. In particular examples, the identified agent alters the activity of an ischemic stroke-related molecule that is upregulated or downregulated following an ischemic stroke. For example, the agent can normalize activity of an ischemic stroke-related molecule that is upregulated or downregulated following an ischemic stroke, such as by increasing the activity of an ischemic stroke-related molecule that is downregulated following an ischemic stroke, or decreasing activity of an ischemic stroke-related molecule that is upregulated following an ischemic stroke. The disclosed methods can be performed in vitro (for example in a cell culture) or in vivo (such as in a mammal).

In one example, the test agent is an agent in pre-clinical or clinical trials or approved by a regulatory agency (such as the Food and Drug Administration, FDA), to treat ischemic stroke. For example, the method can be used to determine if the agent alters the activity of one or more ischemic stroke-related molecules that modifies response to treatment and can predict the best responders.

In another example, the method is used to identify a particular class of agents, such as those that are effective against hypoxia. For example, one or more test agents can be screened using the methods disclosed herein, and differential expression of the disclosed hypoxia-related genes (or proteins) measured. Test agents that alter the activity of one or more disclosed hypoxia-related molecules are candidates for treatment of hypoxia.

The disclosed methods can also be used in toxicogenomics, for example to identify genes or proteins whose expression is altered in response to medication-induced toxicity and side-effects. In one example, the disclosed ischemic stroke-related molecules are screened to identify those whose activity is altered in response to an agent. For example, the disclosed ischemic stroke-related molecules can be used determine if an agent promotes or induces ischemic stroke. Briefly, the test agent is contacted with a normal cell (such as a PBMC, endothelia, or neuronal cell), such as a cell that has not been exposed to conditions that mimic an ischemic stroke, and differential expression of one or more ischemic stroke molecules measured using the methods disclosed herein. If the agent promotes or induces differential expression of one or more, such as at least 4 of the disclosed ischemic stroke-related molecules (such as those listed in Tables 2-5) in an otherwise normal cell or mammal (for example as compared to a similar cell cultured in similar conditions without the test agent), this indicates that the agent may cause or promote an ischemic stroke in vivo. Such a result may indicate that further studies of the agent are needed. In another example, cells from a subject who is to receive a pharmaceutical agent are obtained (such as PBMCs), and the pharmaceutical agent incubated with the cells as described above, to determine if the pharmaceutical agent causes or promotes differential expression of one or more ischemic stroke-related molecules. Such a result would indicate that the subject may react adversely to the agent, or that a lower dose of the agent should be administered.

The disclosure also provides methods of generating a brain imaging tracer or white blood cell tracers for molecular imaging, such as imaging to determine if a subject has had an ischemic stroke. Briefly, a labeled antibody that recognizes an ischemic stroke-related molecule, such as those involved in white blood cell activation and differentiation, those involved in the response to altered cerebral microenvironment, or combinations thereof (see Table 5). In one example, the label is a fluorophore, radioisotope, or other compound that can be used in diagnostic imaging, such as a nuclear medicine radioisotope (for example $^{99m}$Technetium for use with single photon emission computed tomography, $^{18}$Fluorodeoxyglucose ($^{18}$FDG) for use with positron emission tomography, or a paramagnetic contrast agent for magnetic resonance imaging). The labeled antibody can be administered to the subject, for example intravenously, and the subject imaged using standard methods.

The foregoing and other features and advantages of the disclosure will become more apparent from the following detailed description of a several embodiments.

SEQUENCE LISTING

Figure 1:
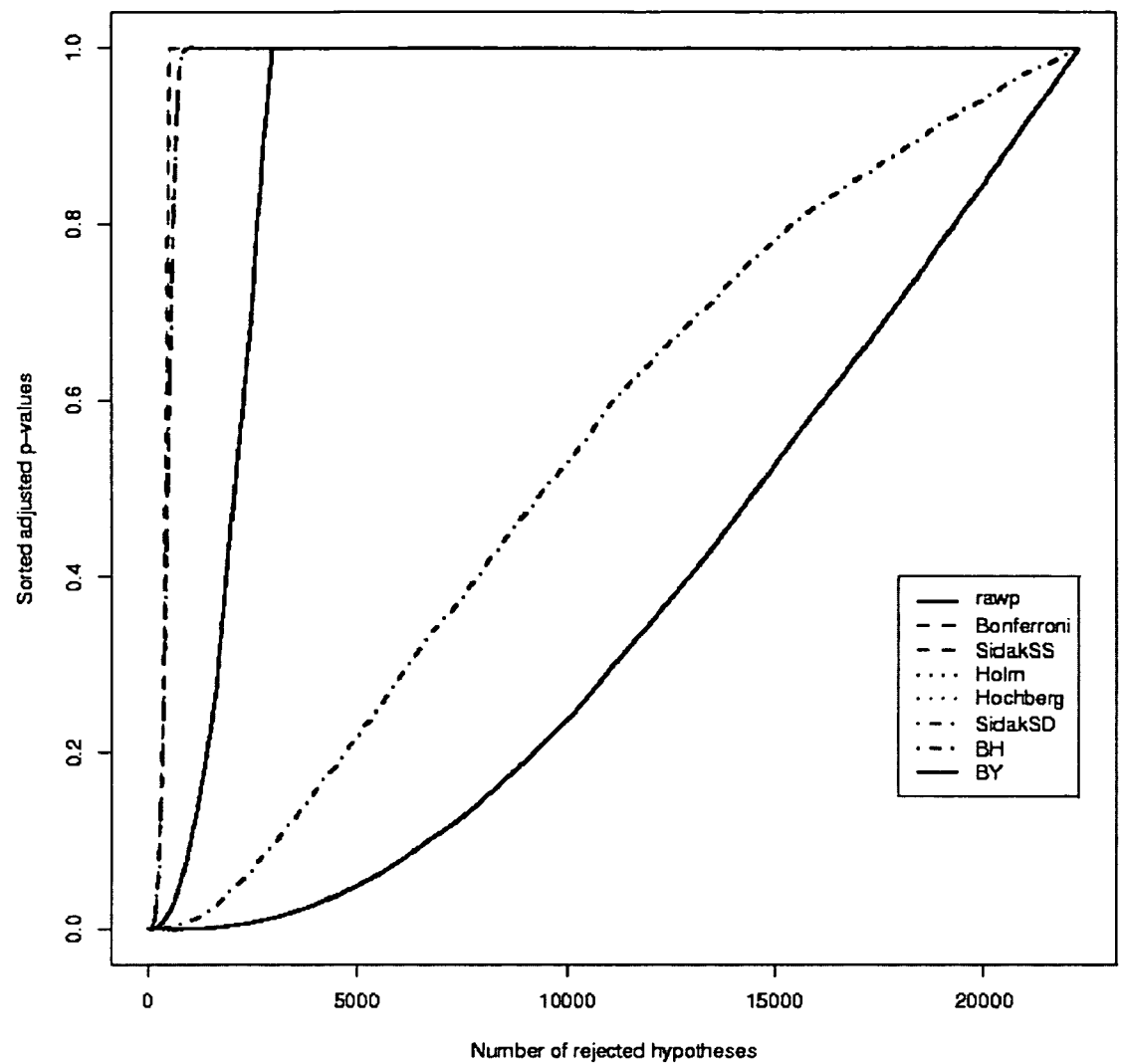
FIG. 1 is a graph showing the effects of various multiple comparison correction techniques on the ischemic stroke microarrays.

The nucleic acid sequences listed in the accompanying sequence listing are shown using standard letter abbreviations for nucleotide bases. Only one strand of each nucleic acid sequence is shown, but the complementary strand is understood as included by any reference to the displayed strand.

SEQ ID NOS: 1-2 are oligonucleotide sequences used to perform RT-PCR to determine expression levels of adrenomedullin.

SEQ ID NOS: 3-4 are oligonucleotide sequences used to perform RT-PCR to determine expression levels of CD14.

SEQ ID NOS: 5-6 are oligonucleotide sequences used to perform RT-PCR to determine expression levels of CD36.

SEQ ID NOS: 7-8 are oligonucleotide sequences used to perform RT-PCR to determine expression levels of caspase 1.

SEQ ID NOS: 9-10 are oligonucleotide sequences used to perform RT-PCR to determine expression levels of a-Catenin.

SEQ ID NOS: 11-12 are oligonucleotide sequences used to perform RT-PCR to determine expression levels of FcR2a.

SEQ ID NOS: 13-14 are oligonucleotide sequences used to perform RT-PCR to determine expression levels of FcER1a.

SEQ ID NOS: 15-16 are oligonucleotide sequences used to perform RT-PCR to determine expression levels of cathepsin B.

SEQ ID NOS: 17-18 are oligonucleotide sequences used to perform RT-PCR to determine expression levels of TRL2.

SEQ ID NOS: 19-20 are oligonucleotide sequences used to perform RT-PCR to determine expression levels of INFGR1.

SEQ ID NOS: 21-42 are nucleic acid sequences of probes used to detect the expression of CD163.

SEQ ID NOS: 43-53 are nucleic acid sequences of probes used to detect the expression of hypothetical protein FLJ22662 laminin A motif.

SEQ ID NOS: 54-86 are nucleic acid sequences of probes used to detect the expression of amyloid beta (A4) precursor-like protein 2.

SEQ ID NOS: 87-97 are nucleic acid sequences of probes used to detect the expression of N-acetylneuraminate pyruvate lyase.

SEQ ID NOS: 98-108 are nucleic acid sequences of probes used to detect the expression of v-fos FBJ murine osteosarcoma viral oncogene homolog.

SEQ ID NOS: 109-119 are nucleic acid sequences of probes used to detect the expression of toll-like receptor 2.

SEQ ID NOS: 120-174 are nucleic acid sequences of probes used to detect the expression of chondroitin sulfate proteoglycan 2 (versican).

SEQ ID NOS: 175-218 are nucleic acid sequences of probes used to detect the expression of interleukin 13 receptor, alpha 1.

SEQ ID NOS: 219-229 are nucleic acid sequences of probes used to detect the expression of CD14 antigen.

SEQ ID NOS: 230-240 are nucleic acid sequences of probes used to detect the expression of bone marrow stromal cell antigen 1/CD157.

SEQ ID NOS: 241-262 are nucleic acid sequences of probes used to detect the expression of complement component 1 q subcomponent, receptor 1.

SEQ ID NOS: 263-284 are nucleic acid sequences of probes used to detect the expression of paired immunoglobin-like type 2 receptor alpha.

SEQ ID NOS: 285-295 are nucleic acid sequences of probes used to detect the expression of Fc fragment of IgG, high affinity Ia, receptor for (CD64).

SEQ ID NOS: 296-328 are nucleic acid sequences of probes used to detect the expression of ectonucleoside triphosphate diphosphohydrolase 1.

SEQ ID NOS: 329-350 are nucleic acid sequences of probes used to detect the expression of CD36 antigen (collagen type I receptor, thrombospondin receptor).

SEQ ID NOS: 351-361 are nucleic acid sequences of probes used to detect the expression of adrenomedullin.

SEQ ID NOS: 362-383 are nucleic acid sequences of probes used to detect the expression of dual specificity phosphatase 1.

SEQ ID NOS: 384-394 are nucleic acid sequences of probes used to detect the expression of cytochrome b-245, beta polypeptide (chronic granulomatous disease).

SEQ ID NOS: 395-405 are nucleic acid sequences of probes used to detect the expression of leukotriene A4 hydrolase.

SEQ ID NOS: 406-427 are nucleic acid sequences of probes used to detect the expression of erythroblastosis virus E26 oncogene homolog 2 (avian).

SEQ ID NOS: 428-438 are nucleic acid sequences of probes used to detect the expression of neuronal apoptosis inhibitory protein: Homo sapiens transcribed sequence with strong similarity to protein sp:Q13075 (*H. sapiens*) BIR1_HUMAN Baculoviral IAP repeat-containing protein 1.

SEQ ID NOS: 439-460 are nucleic acid sequences of probes used to detect the expression of KIAA0146 protein.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

PBMC: peripheral blood mononuclear cell

Real time-PCR: real time polymerase chain reaction

Administration: To provide or give a subject an agent by any effective route. Exemplary routes of administration include, but are not limited to, oral, injection (such as subcutaneous, intramuscular, intradermal, intraperitoneal, and intravenous), sublingual, rectal, transdermal, intranasal, vaginal and inhalation routes.

Amplifying a nucleic acid molecule: To increase the number of copies of a nucleic acid molecule, such as a gene or fragment of a gene, for example a region of a ischemic stroke-associated gene. The resulting products are called amplification products.

An example of in vitro amplification is the polymerase chain reaction (PCR), in which a biological sample obtained from a subject (such as a sample containing PBMCs) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Quantitative real-time PCR is another form of in vitro amplifying nucleic acid molecules, enabled by Applied Biosystems (TaqMan PCR). Real-time quantitative TaqMan PCR has reduced the variability traditionally associated with quantitative PCR, thus allowing the routine and reliable quantification of PCR products to produce sensitive, accurate, and reproducible measurements of levels of gene expression. The 5' nuclease assay provides a real-time method for detecting only specific amplification products. During amplification, annealing of the probe to its target sequence generates a substrate that is cleaved by the 5' nuclease activity of Taq DNA polymerase when the enzyme extends from an upstream primer into the region of the probe. This dependence on polymerization ensures that cleavage of the probe occurs only if the target sequence is being amplified. The use of fluorogenic probes makes it possible to eliminate post-PCR processing for the analysis of probe degradation. The probe is an oligonucleotide with both a reporter fluorescent dye and a quencher dye attached. While the probe is intact, the proximity of the quencher greatly reduces the fluorescence emitted by the reporter dye by Förster resonance energy transfer (FRET) through space. Probe design and synthesis has been simplified by the finding that adequate quenching is observed for probes with the reporter at the 5' end and the quencher at the 3' end.

Anti-coagulants: Agents that decrease or prevent blood clotting. Anticoagulants can avoid the formation of new clots, and prevent existing clots from growing (extending), for example by decreasing or stopping the production of proteins necessary for blood to clot. Examples include, but are not limited to, aspirin, heparin, ximelagatran, and warfarin (Coumadin). Administration of anticoagulants is one treatment for ischemic stroke, for example to prevent further strokes. A particular type of anti-coagulant are anti-platelet agents, which can also be used to prevent further strokes from occurring and include aspirin, clopidogrel (Plavix), aspirin/dipyridamole combination (Aggrenox), and ticlopidine (Ticlid). Other agents used to prevent stroke recurrence are antihypertensive drugs and lipid-lowering agents such as statins.

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least four, to at least 10, at least 20, at least 30, at least 50, at least 75, at least 100, at least 150, at least 200, at least 300, at least 500, least 550, at least 600, at least 800, at least 1000, at least 10,000, or more. In particular examples, an array includes nucleic acid molecules, such as oligonucleotide sequences that are at least 15 nucleotides in length, such as about 15-40 nucleotides in length. In particular examples, an array includes oligonucleotide probes or primers which can be used to detect ischemia stroke-associated sequences, such as any combination of at least four of those listed in Table 5, such as at least 10, at least 20, at least 50, at least 100, at least 150, at least 160, at least 170, at least 175, at least 180, at least 185, at least 200, at least 400, at least 500, at least 510, at least 550, at least 575, at least 600, at least 620, or at least 630 of the sequences listed in any of Tables 2-5. In some examples, an array includes oligonucleotide probes or primers which can be used to detect at least one gene from each of the four classes of genes listed in Table 5, such as at least 2, at least 3, at least 5, or even at least 10 genes from each of the four classes of genes listed in Table 5.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to ischemic stroke-associated proteins, such as any combination of at least four of those listed in Table 5, such as at least 10, at least 20, at least 50, at least 100, at least 150, at least 160, at least 170, at least 175, at least 180, at least 185, at least 200, at least 400, at least 500, at least 510, at least 550, at least 575, at least 600, at least 620, or at least 630 of the sequences listed in any of Tables 2-5. In particular examples, an array includes antibodies or proteins that can detect at least one protein from each class listed in Table 5, such as at least 2, at least 3, at least 5, or even at least 10 genes from each class listed in Table 5.

Baculoviral IAP repeat-containing protein 1 (Birc1): A protein that includes one or more baculoviral IAP repeat (BIR) domains, which is capable of decreasing (an in some examples inhibiting) the biological activity of caspases, and in some examples thereby decreasing or inhibiting apoptosis. The term baculoviral IAP repeat-containing protein 1 includes any Birc1 gene, cDNA, mRNA, or protein from any organism and that is a Birc1 that can decrease or inhibit caspase biological activity. Also referred to in the literature as neuronal apoptosis inhibitory protein (Naip).

Birc1 sequences are publicly available. For example, GenBank Accession Nos: NM_004536 and NP_004527 disclose human Birc1 nucleic acid and protein sequences, respectively and GenBank Accession Nos: NM_010870 and NP_035000 disclose mouse Birc1 nucleic acid and proteins sequences, respectively.

In one example, a Birc1 sequence includes a full-length wild-type (or native) sequence, as well as Birc1 allelic variants, variants, fragments, homologs or fusion sequences that retain the ability to decrease or inhibit caspase biological activity. In certain examples, Birc1 has at least 80% sequence identity, for example at least 85%, 90%, 95%, or 98% sequence identity to a native Birc1. In other examples, Birc1 has a sequence that hybridizes under very high stringency conditions to a sequence set forth in GenBank Accession No. NM_010870 or NM_004536, and retains Birc1 activity.

Binding or stable binding: An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding.

Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate).

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Bone marrow stromal cell antigen 1 (BST-1): A glycosylphosphatidylinositol (GPI)-anchored protein involved in adhesion to extracellular matrix proteins and in chemotaxis induced in vitro by formyl-methionyl-leucyl-phenylalanine (fMLP), as well as activation of white blood cells. Also known in the art as CD157. The term bone marrow stromal cell antigen 1 (BST-1) includes any BST-1 gene, cDNA, mRNA, or protein from any organism and that is a BST-1 that has BST-1 biological activity. BST-1 sequences are publicly available. For example, GenBank Accession Nos: BT019502 and AAV38309 disclose human BST-1 nucleic acid and proteins sequences, respectively.

In one example, a BST-1 sequence includes a full-length wild-type (or native) sequence, as well as BST-1 allelic variants, variants, fragments, homologs or fusion sequences that retain the ability to function in adhesion and chemotaxis. In certain examples, BST-1 has at least 80% sequence identity, for example at least 85%, 90%, 95%, or 98% sequence identity to a native BST-1. In other examples, BST-1 has a sequence that hybridizes under very high stringency conditions to a sequence set forth in GenBank Accession No. BT019502, and retains BST-1 activity.

CD163: A hemoglobin scavenger receptor. The term CD163 includes any CD163 gene, cDNA, mRNA, or protein from any organism and that is a CD163 that can function as a hemoglobin scavenger receptor. CD163 sequences are publicly available. For example, GenBank Accession Nos: Y18388 and CAB45233 disclose human CD163 nucleic acid and protein sequences, respectively and GenBank Accession Nos: NM_053094 and NP_444324 disclose mouse CD163 nucleic acid and proteins sequences, respectively.

In one example, a CD163 sequence includes a full-length wild-type (or native) sequence, as well as CD163 allelic variants, variants, fragments, homologs or fusion sequences that retain the ability to function as a hemoglobin scavenger receptor. In certain examples, CD163 has at least 80% sequence identity, for example at least 85%, 90%, 95%, or 98% sequence identity to a native CD163. In other examples, CD163 has a sequence that hybridizes under very high stringency conditions to a sequence set forth in GenBank Accession No. Y18388 or NM_053094, and retains CD163 activity.

cDNA (complementary DNA): A piece of DNA lacking internal, non-coding segments (introns) and regulatory sequences which determine transcription. cDNA can be synthesized by reverse transcription from messenger RNA extracted from cells.

Clinical indications of stroke: One or more signs or symptoms that are associated with a subject having (or had) a stroke, such as an ischemic stroke. Particular examples include, but are not limited to: headache, sensory loss (such as numbness, particularly confined to one side of the body or face), paralysis (such as hemiparesis), pupillary changes, blindness (including bilateral blindness), ataxia, memory impairment, dysarthria, somnolence, and other effects on the central nervous system recognized by those of skill in the art.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence (such as an ischemic stroke-related sequence, for example any of the sequences listed in Tables 2-5) to achieve detectable binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol.* 100:266-285, 1983, and by Sambrook et al. (ed.), *Molecular Cloning: A Laboratory Manual*, 2nd ed., vol. 1-3, Cold Spring Harbor Laboratory Press, Cold Spring Harbor, N.Y., 1989.

DNA (deoxyribonucleic acid): A long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Deletion: The removal of one or more nucleotides from a nucleic acid sequence (or one or more amino acids from a protein sequence), the regions on either side of the removed sequence being joined together.

Differential expression: A difference, such as an increase or decrease, in the conversion of the information encoded in a gene (such as an ischemic stroke related gene) into messenger RNA, the conversion of mRNA to a protein, or both. In some examples, the difference is relative to a control or reference value, such as an amount of gene expression that is expected in a subject who has not had an ischemic stroke or an amount expected in a subject who has had an ischemic stroke. Detecting differential expression can include measuring a change in gene expression.

Downregulated or inactivation: When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell). In one example, a control is a relative amount of gene expression or protein expression in a PBMC in a subject who has not suffered an ischemic stroke.

Evaluating a stroke: To determine whether an ischemic stroke has occurred in a subject, to determine the severity of an ischemic stroke, to determine the likely neurological recovery of a subject who has had an ischemic stroke, or combinations thereof.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule can be altered relative to a normal (wild type) nucleic acid molecule. Alterations in gene expression, such as differential expression, includes but is not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who has not had an ischemic stroke) as well as laboratory values, even though possibly arbitrarily set, keeping in mind that such values can vary from laboratory to laboratory.

Laboratory standards and values may be set based on a known or determined population value and can be supplied in the format of a graph or table that permits comparison of measured, experimentally determined values.

Fc fragment of IgG, high affinity Ia, receptor for (high affinity immunoglobulin G receptor Fc gamma RI, FcγRI): One of three classes of receptors for the Fc fragment of IgG (FcγR) that participates in immune complex clearance. Binding of ligand to FcγRI initiates multiple immune activation events, such as phagocytosis, expression of proinflammatory cytokines, and cytotoxicity against Ig-coated target cells. Also known in the art as CD64. The term FcγRI includes any FcγRI gene, cDNA, mRNA, or protein from any organism and that is a FcγRI that can function in immune complex clearance. FcγRI sequences are publicly available. For example, GenBank Accession Nos: NM_000566 (nucleic acid) and CAI12557 (protein) and NP_000557 (protein) disclose human FcγRI sequences.

In one example, a FcγRI sequence includes a full-length wild-type (or native) sequence, as well as FcγRI allelic variants, variants, fragments, homologs or fusion sequences that retain the ability to function in immune complex clearance. In certain examples, FcγRI has at least 80% sequence identity, for example at least 85%, 90%, 95%, or 98% sequence identity to a native FcγRI. In other examples, FcγRI has a sequence that hybridizes under very high stringency conditions to a sequence set forth in GenBank Accession No. NM_000566 and retains FcγRI activity.

Gene expression profile (or fingerprint): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs; in some examples, as few as one or two genes provides a profile, but more genes can be used in a profile, for example at least 3, at least 4, at least 5, at least 10, at least 20, at least 25, at least 50, at least 80, at least 100, at least 190, at least 200, at least 300, at least 400, at least 500, at least 550, at least 600, or at least 630 or more. A gene expression profile (also referred to as a fingerprint) can be linked to a tissue or cell type (such as PBMCs), to a particular stage of normal tissue growth or disease progression (such as ischemic stroke), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who has not had an ischemic stroke). In one example, a gene expression profile in a subject is read on an array (such as a nucleic acid or protein array).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

| Very High Stringency (detects sequences that share 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

-continued

High Stringency (detects sequences that share 80% identity or greater)

Hybridization:     5x-6x SSC at 65° C.-70° C. for 16-20 hours
Wash twice:        2x SSC at RT for 5-20 minutes each
Wash twice:        1x SSC at 55° C.-70° C. for 30 minutes each Low Stringency (detects sequences that share greater than 50% identity)

Hybridization:     6x SSC at RT to 55° C. for 16-20 hours
Wash at least twice:  2x-3x SSC at RT to 55° C. for 20-30 minutes each.

Hypothetical protein FLJ22662 Laminin A motif: The term hypothetical protein FLJ22662 Laminin A motif sequence includes any hypothetical protein FLJ22662 Laminin A motif sequence gene, cDNA, mRNA, or protein from any organism and that is a hypothetical protein FLJ22662 Laminin A motif sequence. In particular examples, hypothetical protein FLJ22662 Laminin A motif is part of a basement membrane.

Hypothetical protein FLJ22662 Laminin A motif sequences are publicly available. For example, GenBank Accession Nos: BC063561 (nucleic acid), BC000909 (nucleic acid), AAH00909 (protein) and AAH63561 (protein) disclose human sequences. In one example, a hypothetical protein FLJ22662 Laminin A motif sequence includes a full-length wild-type (or native) sequence, as well as hypothetical protein FLJ22662 Laminin A motif allelic variants, variants, fragments, homologs or fusion sequences. In certain examples, CD163 has at least 80% sequence identity, for example at least 85%, 90%, 95%, or 98% sequence identity to a native hypothetical protein FLJ22662 Laminin A motif. In other examples, hypothetical protein FLJ22662 Laminin A motif has a sequence that hybridizes under very high stringency conditions to a sequence set forth in GenBank Accession No. BC063561 or BC000909, and retains FLJ22662 activity.

Insertion: The addition of one or more nucleotides to a nucleic acid sequence, or the addition of one or more amino acids to a protein sequence.

Ischemic stroke: An ischemic stroke occurs when a blood vessel that supplies blood to the brain is blocked or narrowed (as contrasted with a hemorrhagic stroke which develops when an artery in the brain leaks or ruptures and causes bleeding inside the brain tissue or near the surface of the brain). The blockage can be a blood clot that forms or lodges inside the blood vessel (thrombus) or an object (such as an air bubble or piece of tissue) that moves through the blood from another part of the body (embolus).

Ischemic Stroke-related (or associated) molecule: A molecule whose expression is affected by an ischemic stroke. Such molecules include, for instance, nucleic acid sequences (such as DNA, cDNA, or mRNAs) and proteins. Specific examples include those listed in Tables 2-5, as well as fragments of the full-length genes, cDNAs, or mRNAs (and proteins encoded thereby) whose expression is altered (such as upregulated or downregulated) in response to an ischemic stroke.

Examples of ischemic stroke-related molecules whose expression is upregulated following an ischemic stroke include sequences involved in white blood cell activation and differentiation, sequences related to hypoxia, sequences involved in vascular repair, and sequences related to a specific PBMC response to the altered cerebral microenvironment, such as those genes listed in Table 5. Specific examples of ischemic stroke-related molecules whose expression is upregulated following an ischemic stroke include CD163; hypothetical protein FLJ22662 Laminin A motif; bone marrow stromal cell antigen 1 (also known as CD157); Fc fragment of IgG, high affinity Ia, receptor for (CD64); baculoviral IAP repeat-containing protein 1 (also known as neuronal apoptosis inhibitory protein); and KIAA0146, or any one of these.

Ischemic stroke-related molecules can be involved in or influenced by an ischemic stroke in different ways, including causative (in that a change in an ischemic stroke-related molecule leads to development of or progression to an ischemic stroke) or resultive (in that development of or progression to an ischemic stroke causes or results in a change in the ischemic stroke-related molecule).

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. For example, an isolated cell, such as an isolated PBMC is one that is substantially separated from other cells, such as other blood cells.

KIAA0146: The term KIAA0146 includes any KIAA0146 gene, cDNA, mRNA, or protein from any organism and that is a KIAA0146 sequence. KIAA0146 sequences are publicly available. For example, GenBank Accession Nos: AAH15561 (protein), BAA09767 (protein), D63480 (nucleic acid), and BC015561 (nucleic acid) disclose human KIAA0146 sequences.

In one example, a KIAA0146 sequence includes a full-length wild-type (or native) sequence, as well as KIAA0146 allelic variants, variants, fragments, homologs or fusion sequences. In certain examples, KIAA0146 has at least 80% sequence identity, for example at least 85%, 90%, 95%, or 98% sequence identity to a native KIAA0146. In other examples, KIAA0146 has a sequence that hybridizes under very high stringency conditions to a sequence set forth in GenBank Accession No. D63480 or BC015561, and retains KIAA0146 activity.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, cofactors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Neurological sequelae: Any abnormality of the nervous system (such as the central nervous system) following or resulting from a disease or injury or treatment, for example following an ischemic stroke.

Nucleic acid array: An arrangement of nucleic acids (such as DNA or RNA) in assigned locations on a matrix, such as that found in cDNA arrays, or oligonucleotide arrays.

Nucleic acid molecules representing genes: Any nucleic acid, for example DNA (intron or exon or both), cDNA, or RNA (such as mRNA), of any length suitable for use as a probe or other indicator molecule, and that is informative about the corresponding gene.

Nucleic acid molecules: A deoxyribonucleotide or ribonucleotide polymer including, without limitation, cDNA, mRNA, genomic DNA, and synthetic (such as chemically synthesized) DNA. The nucleic acid molecule can be double-stranded or single-stranded. Where single-stranded, the nucleic acid molecule can be the sense strand or the antisense strand. In addition, nucleic acid molecule can be circular or linear.

The disclosure includes isolated nucleic acid molecules that include specified lengths of an ischemic stroke-related nucleotide sequence, for example those listed in Tables 2-5. Such molecules can include at least 10, at least 15, at least 20, at least 25, at least 30, at least 35, at least 40, at least 45 or at least 50 consecutive nucleotides of these sequences or more, and can be obtained from any region of an ischemic stroke-related nucleic acid molecule.

Nucleotide: Includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15 or 20 nucleotides.

Oligonucleotide probe: A short sequence of nucleotides, such as at least 8, at least 10, at least 15, at least 20, at least 21, at least 25, or at least 30 nucleotides in length, used to detect the presence of a complementary sequence by molecular hybridization. In particular examples, oligonucleotide probes include a label that permits detection of oligonucleotide probe:target sequence hybridization complexes.

Open reading frame (ORF): A series of nucleotide triplets (codons) coding for amino acids without any internal termination codons. These sequences are usually translatable into a peptide.

Peripheral blood mononuclear cells (PBMCs): Cells present in the blood that have one round nucleus. Examples include lymphocytes, monocytes, and natural killer cells. PBMCs do not include neutrophils, eosinophils or basophils.

Primers: Short nucleic acid molecules, for instance DNA oligonucleotides 10-100 nucleotides in length, such as about 15, 20, 25, 30 or 50 nucleotides or more in length. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, for example, a primer including 30 consecutive nucleotides of an ischemic stroke-related nucleotide molecule will anneal to a target sequence, such as another homolog of the designated ischemic stroke-related protein, with a higher specificity than a corresponding primer of only 15 nucleotides. Thus, in order to obtain greater specificity, primers can be selected that include at least 20, at least 25, at least 30, at least 35, at least 40, at least 45, at least 50 or more consecutive nucleotides of a ischemic stroke-related nucleotide sequence.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides. In addition, a purified cell, such as a purified PBMC, is one that is substantially separated from other cells, such as other blood cells. In one example, purified PBMCs are at least 90% pure, such as at least 95% pure, or even at least 99% pure.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Sample: A biological specimen containing genomic DNA, RNA (including mRNA), protein, or combinations thereof, obtained from a subject. Examples include, but are not limited to, peripheral blood, urine, saliva, tissue biopsy, surgical specimen, amniocentesis samples and autopsy material. In one example, a sample includes peripheral blood mononuclear cells (PBMCs).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.*

2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1 ; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1 -r 2.

To compare two amino acid sequences, the options of B12seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

```
                              1                   20
   Target Sequence:      AGGTCGTGTACTGTCAGTCA
                         |  ||  |||  ||||  ||||  |
   Identified Sequence:  ACGTGGTGAACTGCCAGTGA
```

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Sequences involved in (or related to) white blood cell activation and differentiation: Nucleic acid molecules (such as mRNA, cDNA, gene) and the corresponding protein, whose expression is altered (such as upregulated or downregulated) in connection with the specialization, mobilization, or proliferation of white blood cells, or combinations thereof, for example sequences that are differentially expressed to cause (or are differentially expressed as a result of) specialization, mobilization, and/or proliferation of white blood cells.

Exemplary sequences involved in white blood cell activation and differentiation include genes involved in cell adhesion, enzymes involved in the cell membrane remodeling allowing preparation for change to a more differentiated state, and genes related to cell-cell interactions. Particular examples include, but are not limited to, CD163; hypothetical protein FLJ22662 Laminin A motif; amyloid beta (A4) precursor-like protein 2; N-acetylneuraminate pyruvate lysase; v-fos FBJ murine osteosarcoma viral oncogene homolog; toll-like receptor 2; chondroitin sulfate proteoglycan 2 (versican); interleukin 13 receptor, alpha 1; CD14 antigen; bone marrow stromal cell antigen 1 (also known as CD157); complement component 1, q subcomponent, receptor 1; and paired immunoglobin-like type 2 receptor alpha; and Fc fragment of IgG, high affinity Ia, receptor for (CD64).

Sequences involved in (or related to) hypoxia: Nucleic acid molecules (such as mRNA, cDNA, gene) and the corresponding protein, whose expression is altered (such as upregulated or downregulated) in response to decreased available oxygen in the blood and tissues. For example, the brain is hypoxic following an ischemic stroke. Particular examples include, but are not limited to, adrenomedullin; dual specificity phosphatase 1; cytochrome b-245, beta polypeptide (chronic granulomatous disease); eukotriene A4 hydrolase; erythroblastosis virus E26 oncogene homolog 2 (avian); and neutrophil cytosolic factor 2 (65 kDa, chronic granulomatous disease, autosomal 2).

Sequences involved in (or related to) vascular repair: Nucleic acid molecules (such as mRNA, cDNA, gene) and the corresponding protein, whose expression is altered (such as upregulated or downregulated) in response to injury to a blood vessel. Particular examples include, but are not limited to, thrombomodulin; ectonucleoside triphosphate diphosphohydrolase 1; and CD36 antigen (collagen type I receptor, thrombospondin receptor).

Sequences involved in (or related to) a specific PBMC response to the altered cerebral microenvironment: Nucleic acid molecules (such as mRNA, cDNA, gene) and the corresponding protein, whose expression is altered (such as upregulated or downregulated) in PBMCs in response to changes in the brain microenvironment.

Examples include those potentially associated with enhanced neurotransmitter degradation (such as catechol-o-methyl transferase and glutamine ligase), those that permit increased modulation of $Ca^{2+}$ homeostasis in the cerebral environment, genes involved in the inhibition of neuronal apoptosis (such as the neuronal apoptosis inhibitory protein and Ets2), genes involved in proNGF-induced neuronal cell death (such as sortilin), genes involved in apoptotic cell death in the hippocampus after global cerebral ischemic injury (such as phospholipid scramblase 1), and genes involved in neurite growth in neuronal development (such as growth arrest-specific 7).

Particular examples include, but are not limited to, catechol-O-methyltransferase; glutamate-ammonia ligase (glutamine ligase); S100 calcium binding protein A8 (calgranulin A); neuronal apoptosis inhibitory protein: *Homo sapiens* transcribed sequence with strong similarity to protein sp:Q13075 (*H. sapiens*) BIR1_HUMAN Baculoviral IAP repeat-containing protein 1; sortilin; phospholipid scramblase 1; growth-arrest-specific 7; and GLI pathogenesis-related 1 (glioma).

Subject: Living multi-cellular vertebrate organisms, a category that includes human and non-human mammals.

Target sequence: A sequence of nucleotides located in a particular region in the human genome that corresponds to a desired sequence, such as ischemic stroke related sequence. The target can be for instance a coding sequence; it can also be the non-coding strand that corresponds to a coding sequence. Examples of target sequences include those sequences associated with ischemic stroke, such as any of those listed in Tables 2-5.

Test agent: Any substance, including, but not limited to, a protein (such as an antibody), nucleic acid molecule, organic compound, inorganic compound, or other molecule of interest. In particular examples, a test agent can permeate a cell membrane (alone or in the presence of a carrier).

Therapeutically effective amount: An amount of a pharmaceutical preparation that alone, or together with a pharmaceutically acceptable carrier or one or more additional therapeutic agents, induces the desired response. A therapeutic agent, such as an anticoagulant or a thrombolytic agent, is administered in therapeutically effective amounts.

Effective amounts a therapeutic agent can be determined in many different ways, such as assaying for a reduction in atherosclerotic disease or improvement of physiological condition of a subject having vascular disease. Effective amounts also can be determined through various in vitro, in vivo or in situ assays.

Therapeutic agents can be administered in a single dose, or in several doses, for example daily, during a course of treatment. However, the effective amount of can be dependent on the source applied, the subject being treated, the severity and type of the condition being treated, and the manner of administration.

In one example, it is an amount sufficient to partially or completely alleviate symptoms of ischemic stroke within a subject. Treatment can involve only slowing the progression of the ischemic stroke temporarily, but can also include halting or reversing the progression of the ischemic stroke permanently. For example, a pharmaceutical preparation can decrease one or more symptoms of ischemic stroke, for example decrease a symptom by at least 20%, at least 50%, at least 70%, at least 90%, at least 98%, or even at least 100%, as compared to an amount in the absence of the pharmaceutical preparation.

Thrombolytics: Agents that promote lysis of thrombi that occlude a cerebral vessel. Examples include, but are not limited to, tissue plasminogen activator (tPA), urokinase, and pro-urokinase. Administration of antithrombotics is one treatment for ischemic stroke, and is often a first line treatment for ischemic stroke. For example, intravenous t-PA can be administered within 3 hours of ischemic stroke onset. Intra-arterial thrombolytic therapy and mechanical clot-retrieval devices can be used to promote rapid lysis of thrombi.

Treating a disease: "Treatment" refers to a therapeutic intervention that ameliorates a sign or symptom of a disease or pathological condition, such a sign or symptom of vascular disease. Treatment can also induce remission or cure of a condition, such as an ischemic stroke. In particular examples, treatment includes preventing a disease, for example by inhibiting the full development of a disease, such as preventing development of a disease or disorder that results from an ischemic stroke. Prevention of a disease does not require a total absence of disease. For example, a decrease of at least 50% can be sufficient.

Under conditions sufficient for: A phrase that is used to describe any environment that permits the desired activity.

In one example, includes culturing cells (such as PBMCs) under conditions sufficient to mimic an ischemic stroke, such as culturing the cells under hypoxic conditions, hypoglycemic conditions, or both.

In another example, includes administering a test agent to a cell culture or a subject sufficient to allow the desired activity. In particular examples, the desired activity is altering the activity (such as the expression) of an ischemic stroke-related molecule.

Upregulated or activation: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product increases by at least 2-fold, for example at least 3-fold or at least 4-fold, as compared to a control (such an amount of gene expression in a normal cell). In one example, a control is a relative amount of gene expression in a PBMC in a subject who has not suffered an ischemic stroke.

Ischemic Stroke-Related Molecules

The inventors have identified 22-637 genes whose expression is altered (such as upregulated or downregulated) following an ischemic stroke. The number of genes identified depended on the specificity and sensitivity of the algorithm used. For example, using the PAM dataset 22 ischemic stroke related genes were identified (Table 5), using the Westfall and Young dataset 82 ischemic stroke related genes were identified (Table 4), using the Bonferroni correction set 190 ischemic stroke related genes were identified (Table 3), and using the Benjamini & Yekutieli set 637 ischemic stroke related genes were identified (Table 2). One skilled in the art will appreciate that changes in protein expression can be detected as an alternative to detecting gene expression.

Several genes not previously associated with ischemic stroke were identified, such as at least CD163; hypothetical protein FLJ22662 Laminin A motif; bone marrow stromal cell antigen 1 (BST-1, also referred to in the literature as CD157); Fc fragment of IgG, high affinity Ia, receptor for (FcγRI, also known as CD64); baculoviral IAP repeat-containing protein 1; and KIAA0146. In particular examples, all of these genes were upregulated following an ischemic stroke. In one example, four classes of genes whose expression was upregulated following an ischemic stroke were identified: sequences involved in activation and differentiation of white blood cells, sequences related to hypoxia, sequences involved in vascular repair, and sequences related to altered cerebral microenvironment. Particular examples of such genes (and their corresponding proteins) are provided in Table 5.

Based on the identification of these ischemic stroke-related molecules, methods were developed to evaluate a stroke. For example, the disclosed methods can be used to diagnose an ischemic stroke, determine the severity of an ischemic stroke, determine the likely neurological recovery of a subject who had an ischemic stroke, or combinations thereof. The method can further include determining an appropriate therapy for a subject found to have experienced an ischemic stroke using the disclosed assays.

The disclosed methods provide a rapid, straightforward, and accurate genetic screening method performed in one assay for evaluating ischemic stroke. It allows identification of subjects who may require anticoagulant therapy following an ischemic stroke. For example, by establishing that an individual has had an ischemic stroke, effective therapeutic measures, such as the emergent administration of a thrombolytic agent or of treatments to prevent stroke recurrence and extension, can be instituted.

Evaluation of an Ischemic Stroke

Provided herein are methods of evaluating a stroke. Particular examples of evaluating a stroke include determining whether a subject, such as an otherwise healthy subject, or a subject suspected or at risk of having an ischemic stroke, has had an ischemic stroke, assessing the severity of an ischemic stroke, predicting the likelihood of neurological recovery of a subject who has had an ischemic stroke, or combinations thereof. The identification of a subject who has had an ischemic stroke can help to evaluate other clinical data (such as neurological impairment or brain imaging information) to determine whether an ischemic stroke has occurred. In particular examples, the method can determine with a reasonable amount of sensitivity and specificity whether a subject has suffered an ischemic stroke within the previous 72 hours, such as within the previous 48 hours, previous 24 hours, or previous 12 hours. In some examples, isolated or purified PBMCs obtained from the subject are used to determine whether a subject has had an ischemic stroke.

In particular examples, the method also includes administering an appropriate treatment therapy for subjects who have had an ischemic stroke. For example, subjects identified or evaluated as having had an ischemic stroke can then be provided with appropriate treatments, such as anti-platelet agents (for example aspirin) that would be appropriate for a subject identified as having had an ischemic stroke but not as appropriate for a subject who has had a hemorrhagic stroke. It is helpful to be able to classify a subject as having had an ischemic stroke, because the treatments for ischemic stroke are often distinct from the treatments for hemorrhagic stroke. In fact, treating a hemorrhagic stroke with a therapy designed for an ischemic stroke (such as a thrombolytic agent) can have devastating clinical consequences. Hence using the results of the disclosed assays to help distinguish ischemic from hemorrhagic stroke offers a substantial clinical benefit, and allows subjects to be selected for treatments appropriate to ischemic stroke but not hemorrhagic stroke.

In particular examples, methods of evaluating a stroke involve detecting differential expression (such as an increase or decrease in gene or protein expression) in any combination of at least four ischemic stroke-related molecules of the subject, such as any combination of at least four of the genes (or proteins) listed in any of Tables 2-5. In one example, the method includes screening expression of one or more of CD163; hypothetical protein FLJ22662 Laminin A motif; BST-1; FcγRI; baculoviral IAP repeat-containing protein 1; or KIAA0146, or a combination of ischemic stroke-related molecules that includes at least 1, at least 2, at least 3, at least 4, at least 5 or at least 6 of these molecules. For example, the method can include screening expression of CD163, along with other ischemic stroke-related molecules (such as any combination that includes at least 3 additional molecules listed in Tables 2-5).

Differential expression can be represented by increased or decreased expression in the at least one ischemic stroke-related molecule (for instance, a nucleic acid or a protein). For example, differential expression includes, but is not limited to, an increase or decrease in an amount of a nucleic acid molecule or protein, the stability of a nucleic acid molecule or protein, the localization of a nucleic acid molecule or protein, or the biological activity of a nucleic acid molecule or protein. Specific examples include evaulative methods in which changes in gene expression in at least four ischemic stroke-related nucleic acid molecules (or corresponding protein) are detected (for example nucleic acids or proteins obtained from a subject thought to have had or known to have had an ischemic stroke), such as changes in gene (or protein) expression in any combination of at least 5, at least 10, at least 15, at least 20, at least 25, at least 50, at least 100, at least 150, at least 160, at least 170, at least 175, at least 180, at least 185, at least 200, at least 250, at least 300, at least 400, at least 500, at least 510, at least 550, at least 575, at least 600, at least 620, at least 630, or at least 637 ischemic stroke-related molecules. Exemplary ischemic stroke-related molecules are provided in Tables 2-5.

In particular examples a change in expression is detected in a subset of ischemic stroke-related molecules (such as nucleic acid sequences or protein sequences) that selectively evaluate a stroke, for example to determine if a subject has had an ischemic stroke. In a particular example, the subset of molecules can include a set of any combination of four ischemic stroke-related genes listed in Table 5, or a set of any combination of 22 ischemic stroke-related genes listed in Table 5. In a particular example, the subset of molecules includes any combination of at least one gene (or protein) from each class of the four classes listed in Table 5, such as at least 2, at least 3, at least 5, or at least 10 genes from each class listed in Table 5.

In a particular example, differential expression is detected in ischemic stroke-related molecules that are both upregulated and down regulated. For example, increased expression of one or more of CD163; hypothetical protein FLJ22662 Laminin A motif; BST-1; FcγRI; baculoviral IAP repeat-containing protein 1; or KIAA0146, and decreased gene (or protein) expression of one or more of intercellular adhesion molecule 2, protein kinase D2, GATA binding protein 3, hypothetical protein FLJ20257, or protein kinase C, theta, indicates that the subject has had a stroke, has had a severe stroke, has a lower likelihood of neurological recovery, or combinations thereof. For example, differential expression can be detected by determining if the subject has increased gene (or protein) expression of CD163; hypothetical protein FLJ22662 Laminin A motif; BST-1; FcγRI; baculoviral IAP repeat-containing protein 1; and KIAA0146, and determining if the subject has decreased gene (or protein) expression of intercellular adhesion molecule 2, protein kinase D2, GATA binding protein 3, hypothetical protein FLJ20257, and protein kinase C, theta.

In particular examples, the number of ischemic stroke-related genes screened is at least 5, at least 10, at least 15, at least 20, at least 25, at least 50, at least 100, at least 150, at least 160, at least 170, at least 175, at least 180, at least 185, at least 200, at least 250, at least 300, at least 400, at least 500, at least 510, at least 550, at least 575, at least 600, at least 620, at least 630, or at least 637 ischemic stroke-related molecules. In other examples, the methods employ screening no more than 637, no more than 630, no more than 620, no more than 600, no more than 575, no more than 550, no more than 510, no more than 500, no more than 400, no more than 300, no more than 250, no more than 200, no more than 185, no more than 180, no more than 175, no more than 170, no more than 160, no more than 150, no more than 100, no more than 50, no more than 25, no more than 20, no more than 15, no more than 10, no more than 5, or no more than 4 ischemic stroke-related genes. Examples of particular ischemic stroke-related genes are shown in Tables 2-5. In one example, the number of ischemic stroke-related genes screened includes at least one gene from each class listed in Table 5, such as at least 2, at least 3, at least 5, or at least 10 genes from each class listed in Table 5.

In certain methods, differential expression includes over- or under-expression of an ischemic stroke-related molecule. For instance, differential expression can include overexpression, for instance overexpression of any combination of at least 4 molecules (such at least 10 or at least 20 molecules) shown in Table 5, or any combination of at least 4 molecules in any of Tables 2-4 with a positive t-statistic value, such as a t-statistic value of at least 3, such as at least 3.5, at least 3.6 or even at least 3.7. In a particular example, differential expression includes overexpression of any combination of at least one gene from each class listed in Table 5, such as at least 2, at least 3, at least 5, or at least 10 genes from each of the classes listed in Table 5. In another example, differential expression includes underexpression, for instance underexpression of any combination of at least 5 molecules (such at least 50 or at least 150 molecules) shown in Tables 2-4 with a negative t-statistic value, such as a t-statistic value of less than −3, such as less than −3.5, less than −3.6 or even less than −3.7. In a specific example, differential expression includes any combination of underexpression or overexpression of at least 4 ischemic stroke-related molecules shown in Tables 2-4, such as overexpression of at least 3 ischemic stroke-related molecules shown in Tables 2-5 with a positive t-statistic value and underexpression of at least one ischemic stroke related molecule shown in Tables 2-4 with a negative t-statistic value, or for example overexpression of at least 4 ischemic stroke-related molecules shown in Tables 2-5 with a positive t-statistic value, or for example, overexpression of at least 2 ischemic stroke-related molecules shown in Tables 2-5 with a positive t-statistic value and underexpression of at least 2 ischemic stroke related molecules shown in Tables 2-4 with a negative t-statistic value.

In some examples, differential expression of proteins that are associated with ischemic stroke includes detecting patterns of such expression, such as detecting upregulation of CD163; hypothetical protein FLJ22662 Laminin A motif; BST-1; FcγRI; baculoviral IAP repeat-containing protein 1; or KIAA0146, detecting downregulation of intercellular adhesion molecule 2, protein kinase D2, GATA binding protein 3, hypothetical protein FLJ20257, or protein kinase C, theta, or combinations thereof. For example, detecting upregulation or downregulation can include a magnitude of change of at least 25%, at least 50%, at least 100%, or even at least 200%, such as a magnitude of change of at least 25% for CD163; at least 25% for hypothetical protein FLJ22662 Laminin A motif; at least 25% for BST-1; FcγRI; at least 25% for baculoviral IAP repeat-containing protein 1; at least 25% for KIAA0146; at least 25% for intercellular adhesion molecule 2; at least 25% for protein kinase D2; at least 25% for GATA binding protein 3; at least 25% for hypothetical protein FLJ20257; and at least 25% for protein kinase C, theta. Alternatively, upregulation is detected by a level having a t-value of at least 3 and downregulation is detected by a level having a t-value value of no more than −3.

In particular examples, the disclosed method of evaluating a stroke is at least 78% sensitive (such as at least 80% sensitive, at least 85% sensitive, at least 90% sensitive, or at least 95% sensitive) and at least 80% specific (such as at least 85% specific, at least 90% specific, at least 95% specific, or at least 98% specific) for determining whether a subject has had an ischemic stroke.

As used herein, the term "ischemic stroke-related molecule" includes ischemic stroke-related nucleic acid molecules (such as DNA, RNA, for example cDNA or mRNA) and ischemic stroke-related proteins. The term is not limited to those molecules listed in Tables 2-5 (and molecules that correspond to those listed), but also includes other nucleic acid molecules and proteins that are influenced (such as to level, activity, localization) by or during an ischemic stroke, including all of such molecules listed herein. Examples of particular ischemic stroke-related genes are listed in Tables 2-5, such as CD163; hypothetical protein FLJ22662 Laminin A motif; BST-1; FcγRI; baculoviral IAP repeat-containing protein 1; or KIAA0146. In examples where the ischemia-related molecule is an ischemia-related nucleic acid sequence, methods of detecting differential expression can include in vitro nucleic acid amplification, nucleic acid hybridization (which can include quantified hybridization), RT-PCR, real time PCR, or combinations thereof. In examples where the ischemia-related molecule is an ischemia-related protein sequence, methods of detecting differential expression can include in vitro hybridization (which can include quantified hybridization) such as hybridization to a protein-specific binding agent for example an antibody, quantitative spectroscopic methods (for example mass spectrometry, such as surface-enhanced laser desorption/ionization (SELDI)-based mass spectrometry) or combinations thereof.

In particular examples, methods of evaluating a subject who has had or is thought to have had an ischemic stroke includes determining a level of expression (for example in a PBMC) of any combination of at least 4 of the genes (or proteins) listed in Tables 2-5, such as at least 10, at least 15, at least 20, or at least 22 of the genes listed in Table 5, such as at least 150, at least 180, or at least 185 of the gene listed in Table 3, or any combination of at least 500, at least 600, or at least 630 of the genes listed in Table 2. In one example, the method includes determining a level of expression of at least CD163; hypothetical protein FLJ22662 Laminin A motif, BST-1; FcγRI; baculoviral IAP repeat-containing protein 1; or KIAA0146, or any combination of ischemic stroke related molecules that includes 1, 2, 3, 4, 5, or 6 of these molecules. In one example, the method includes determining a level of expression of at least one gene from each class listed in Table 5, such as at least 2, at least 3, at least 5, or at least 10 genes from each class.

Methods of evaluating a stroke can include diagnosing a stroke, stratifying the seriousness of a cerebral ischemic event, and predicting neurological recovery. Similarly, methods of evaluating a stroke can include determining the severity of a stroke, predicting neurological recovery, or combinations thereof. For example, a change in expression in any combination of at least 4 of the genes listed in Tables 2-5 indicates that the subject has had an ischemic stroke. For example, an increase in expression in one or more of CD163; hypothetical protein FLJ22662 Laminin A motif; BST-1; FcγRI; baculoviral IAP repeat-containing protein 1; or KIAA0146 in particular examples indicates that the subject has had an ischemic stroke.

Determining the level of expression can involve measuring an amount of the ischemia-related molecules in a sample derived from the subject, such as a purified PBMC sample. Such an amount can be compared to that present in a control sample (such as a sample derived from a subject who has not had an ischemic stroke or a standard ischemic stroke-related molecule level in analogous samples from a subject not having ischemia or not having a predisposition developing ischemia), wherein a difference (such as an increase or a decrease reflecting an upregulation or downregulation, respectively) in the level of any combination of at least 4 ischemia-related molecules listed in Tables 2-5, such as any combination of at least 4 ischemia-related molecules listed in Table 5, in the subject relative to the control sample is diagnostic for ischemic stroke.

In other examples, the method includes determining a level of expression of any combination of at least four sequences listed in Table 5, such as at least 10, or at least 22 of the sequences listed in Table 5, for example at least 150 of the genes listed in Table 3, such as at least 160, at least 170, at least 175, at least 180, or at least 185 of the genes listed in Table 3, or at least 500 of the ischemic stroke-related molecules listed in Table 2, such as at least 600 of the ischemic stroke-related molecules listed in Table 2. A change in expression in at least four genes listed in Table 5 (or the corresponding proteins), such as at least 22 of the genes (or the corresponding proteins) listed in Table 5, such as 150 or more of the genes listed in Table 3 (or the corresponding proteins), such as 500 or more of the genes listed in Table 2 (or the corresponding proteins, indicates that the subject has had a more severe stroke, has a higher risk of long term adverse neurological sequelae, or combinations thereof, than a subject having a change in expression in less than 500 of the molecules listed in Table 3, less than 150 of the molecules listed in Table 3 or less than 22 (or less than four) of the molecules listed in Table 5. Determining the level of expression can involve measuring an amount of the ischemia-related molecules in a sample derived from the subject. Such an amount can be compared to that present in a control sample (such as a sample derived from a subject who has not had an ischemic stroke or a sample derived from the subject at an earlier time), wherein a difference (such as an increase or a decrease reflecting an upregulation or downregulation, respectively) in the level of at least 4 or at least 22 of the ischemia-related molecules listed in Table 5 (such as at least 150 of the ischemia-related molecules listed in Table 3 or such as at least 500 of the ischemia-related molecules listed in Table 2) in the subject relative to the control sample indicates that the subject has had a more severe stroke, has a higher risk of long term adverse neurological sequelae, or both.

The disclosed methods can further include administering to the subject an appropriate treatment to avoid or reduce ischemic injury, if the presence of differential expression indicates that the subject has had an ischemic stroke. Since the results of the disclosed assays are reliable predictors of the ischemic nature of the stroke, the results of the assay can be used (alone or in combination with other clinical evidence and brain scans) to determine whether thrombolytic therapy designed to lyse a neurovascular occlusion such as a thrombus (for example by using tissue plasminogen activator or streptokinase) should be administered to the subject. In certain example, thrombolytic therapy is given to the subject once the results of the differential gene assay are known if the assay provides an indication that the stroke is ischemic in nature. Such methods can reduce brain damage following an ischemic stroke.

In particular examples, the method includes determining if there is an alteration in the expression of at least four sequences listed in Table 5, such as at least 10, or at least 22 of the sequences listed in Table 5, for example at least 150 of the genes listed in Table 3, such as at least 160, at least 170, at least 175, at least 180, or at least 185 of the genes listed in Table 3, or at least 500 of the ischemic stroke-related molecules listed in Table 2, such as at least 600 of the ischemic stroke-related molecules listed in Table 2. In some examples, detecting differential expression of at least 4 ischemic stroke-related molecules involves quantitatively or qualitatively analyzing a DNA, mRNA, cDNA, protein, or combinations thereof.

If differential expression is detected in at least four, at least 22, at least 150, or at least 500 ischemic stroke-related molecules is identified, this indicates that the subject has experienced an ischemic stroke (and not a hemorrhagic stroke), and a treatment is selected to prevent or reduce brain damage or to provide protection from the onset of brain damage. Examples of such treatment include administration of an anticoagulant, an antithrombotic, or combinations thereof. A particular example includes administration of a thrombolytic agent such as t-PA to lyse the blood clot, alone or in combination with one or more agents that prevent further strokes, such as anticoagulants (such as antiplatelet agents), antihypertensive agents, or lipid lowering agents. In particular examples, the level of expression of a protein in a subject can be appropriately increased or decreased by expressing in the subject a recombinant genetic construct that includes a promoter operably linked to a nucleic acid molecule, wherein the nucleic acid molecule includes at least 10 consecutive nucleotides of an ischemic stroke-related nucleic acid sequence (such as any of the sequences listed in Tables 2-5). Expression of the nucleic acid molecule will change expression of the ischemic stroke-related protein. The nucleic acid molecule can be in an antisense orientation relative to the promoter or in sense orientation relative to the promoter. In some examples, the recombinant genetic construct expresses an ssRNA corresponding to an ischemic stroke-related nucleic acid sequence.

In examples of the methods described herein, detecting differential expression of at least four ischemic stroke-related molecules involves determining whether a gene expression profile from the subject indicates development or progression of brain injury.

In particular examples, the disclosed methods are performed following the onset of signs and symptoms associated with ischemic stroke. Examples of such symptoms include, but are not limited to headache, sensory loss (such as numbness, particularly confined to one side of the body or face), paralysis (such as hemiparesis), pupillary changes, blindness (including bilateral blindness), ataxia, memory impairment, dysarthria, somnolence, and other effects on the central nervous system recognized by those of skill in the art. In particular examples, the method of evaluating a stroke is performed after a sufficient period of time for the differential regulation of the genes (or proteins) to occur, for example at least 24 hours after onset of the symptom or constellation of symptoms that have indicated a potential cerebral ischemic event. In other examples, the method is performed prior to performing any diagnostics imaging tests (such as those that can find anatomic evidence of ischemic stroke). For example, it can be difficult for imaging modalities (such as CT and MRI) to detect acute ischemic strokes, at least until brain changes (such as edema) have taken place in response to the ischemia. Hence the assay described herein is able to detect the stroke even before definitive brain imaging evidence of the stroke is known.

The neurological sequelae of an ischemic event in the central nervous system can have consequences that range from the insignificant to devastating, and the disclosed assays permit early and accurate stratification of risk of long-lasting neurological impairment. For example, a test performed as early as within the first 24 hours of onset of signs and symptoms of a stroke, and even as late as 7-14 days or even as late as 90 days or more after the event can provide clinical data that is highly predictive of the eventual care needs of the subject.

The disclosed assay is also able to identify subjects who have had an ischemic stroke in the past, for example more than 2 weeks ago, or even more than 90 days ago. The identification of such subjects helps evaluate other clinical data (such as neurological impairment or brain imaging information) to determine whether an ischemic stroke has occurred.

In particular examples, the disclosed methods provide a lower cost alternative to expensive imaging modalities (such as MRI and CT scans), can be used in instances where those imaging modalities are not available (such as in field hospitals), can be more convenient than placing people in scanners (especially considering that some people are not able to fit in the scanner, or can not be subjected to MRI if they have certain types of metallic implants in their bodies), or combinations thereof.

Clinical Specimens

Appropriate specimens for use with the current disclosure in diagnosing and prognosing ischemic stroke include any conventional clinical samples, for instance blood or blood-fractions (such as serum). Techniques for acquisition of such samples are well known in the art (for example see Schluger et al. *J. Exp. Med.* 176:1327-33, 1992, for the collection of serum samples). Serum or other blood fractions can be prepared in the conventional manner. For example, about 200 µL of serum can be used for the extraction of DNA for use in amplification reactions. However, if DNA is not amplified, larger amounts of blood can be collected. For example, if at least 5 µg of mRNA is desired, about 20-30 mls of blood can be collected.

In one example, PBMCs are used as a source of isolated nucleic acid molecules or proteins. The inflammatory response from peripheral blood borne white blood cells, in particular monocytes, are also a component of the evolving ischemic lesion (Kochanek et al., *Stroke* 23:1367-79, 1992). One advantage of using blood (for example instead of brain tissue) is that it is easily available can be drawn serially.

Once a sample has been obtained, the sample can be used directly, concentrated (for example by centrifugation or filtration), purified, amplified, or combinations thereof. For example, rapid DNA preparation can be performed using a commercially available kit (such as the InstaGene Matrix, BioRad, Hercules, Calif.; the NucliSens isolation kit, Organon Teknika, Netherlands. In one example, the DNA preparation method yields a nucleotide preparation that is accessible to, and amenable to, nucleic acid amplification. Similarly, RNA can be prepared using a commercially available kit (such as the RNeasy Mini Kit, Qiagen, Valencia, Calif.).

Arrays for Detecting Nucleic Acid and Protein Sequences

In particular examples, methods for detecting a change in expression in the disclosed ischemic stroke-related genes listed in Tables 2-5 use the arrays disclosed herein. Arrays can be used to detect the presence of sequences whose expression is upregulated or downregulated in response to an ischemic stroke, such as sequences listed in Tables 2-5, for example using specific oligonucleotide probes or antibody probes. The arrays herein termed "ischemic stroke detection arrays," are used to evaluate a stroke, for example to determine whether a subject has had an ischemic stroke, determine the severity of the stroke, predict the likelihood of neurological recovery of a subject who has had an ischemic stroke, to identify an appropriate therapy for a subject who has had an ischemic stroke, or combinations thereof. In particular examples, the disclosed arrays can include nucleic acid molecules, such as DNA or RNA molecules, or antibodies.

Nucleic Acid Arrays

In one example, the array includes nucleic acid oligonucleotide probes that can hybridize to any combination of at least four of the ischemic stroke-related gene sequences listed in Table 5, at least 150 of the ischemic stroke-related gene sequences listed in Table 3, or at least 500 of the ischemic stroke-related gene sequences listed in Table 2. In particular examples, an array includes oligonucleotides that can recognize all 22 ischemic stroke-associated genes listed in Table 5, all 82 of the ischemic stroke-related gene sequences listed in Table 4, all 190 of the ischemic stroke-related gene sequences listed in Table 3, or all 637 of the ischemic stroke-related gene sequences listed in Table 2. Certain of such arrays (as well as the methods described herein) can include ischemic stroke-related molecules that are not listed in Tables 2-5.

In a specific example, an array includes oligonucleotide probes that can recognize at least CD163; hypothetical protein FLJ22662 Laminin A motif; BST-1; FcγRI; baculoviral IAP repeat-containing protein 1; and KIAA0146, or a probe that can recognize any one of these molecules. For example, the array can include oligonucleotide probes that can recognize at least 1, at least 2, at least 3, at least 4, at least 5 or at least 6 of the following, CD163; hypothetical protein FLJ22662 Laminin A motif; BST-1; FcγRI; baculoviral IAP repeat-containing protein 1; and KIAA0146. In another example, the array includes an oligonucleotide probe that can recognize at least CD163, for example in combination with other oligonucleotide probes that recognize other ischemic stroke related molecules (such as any combination of at least 3 of those listed in Tables 2-5).

In another specific example, an array includes oligonucleotide probes that can recognize at least one white blood cell activation and differentiation gene, at least one gene related to hypoxia, at least one gene involved in vascular repair, and at least one gene related to a specific PBMC response to the altered cerebral microenvironment, or at least 2, at least 3, at least 5, or at least 10 genes from each of these families.

In one example, a set of oligonucleotide probes is attached to the surface of a solid support for use in detection of ischemic stroke-associated sequences, such as those nucleic acid sequences (such as cDNA or mRNA) obtained from the subject. Additionally, if an internal control nucleic acid sequence is used (such as a nucleic acid sequence obtained from a PBMC from a subject who has not had an ischemic stroke) an oligonucleotide probe can be included to detect the presence of this control nucleic acid molecule.

The oligonucleotide probes bound to the array can specifically bind sequences obtained from the subject, or amplified from the subject (such as under high stringency conditions). Thus, sequences of use with the method are oligonucleotide probes that recognize ischemic stroke-related sequences, such as gene sequences (or corresponding proteins) listed in Tables 2-5. Such sequences can be determined by examining the sequences of the different species, and choosing oligonucleotide sequences that specifically anneal to a particular ischemic stroke-related sequence (such as those listed in Tables 2-5 or represented by those listed in Tables 2-5), but not others. One of skill in the art can identify other ischemic stroke-associated oligonucleotide molecules that can be attached to the surface of a solid support for the detection of other ischemic stroke-associated nucleic acid sequences.

The methods and apparatus in accordance with the present disclosure takes advantage of the fact that under appropriate conditions oligonucleotides form base-paired duplexes with nucleic acid molecules that have a complementary base sequence. The stability of the duplex is dependent on a number of factors, including the length of the oligonucleotides, the base composition, and the composition of the solution in which hybridization is effected. The effects of base composition on duplex stability can be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target sequences and the oligonucleotides bound to the array, the rate of formation of mismatched duplexes may be substantially reduced.

The length of each oligonucleotide sequence employed in the array can be selected to optimize binding of target ischemic stroke-associated nucleic acid sequences. An optimum length for use with a particular ischemic stroke-associated nucleic acid sequence under specific screening conditions can be determined empirically. Thus, the length for each individual element of the set of oligonucleotide sequences including in the array can be optimized for screening. In one example, oligonucleotide probes are from about 20 to about 35 nucleotides in length or about 25 to about 40 nucleotides in length.

The oligonucleotide probe sequences forming the array can be directly linked to the support. Alternatively, the oligonucleotide probes can be attached to the support by non-ischemic stroke-associated sequences such as oligonucleotides or other molecules that serve as spacers or linkers to the solid support.

Protein Arrays

In another example, an array includes protein sequences (or a fragment of such proteins, or antibodies specific to such proteins or protein fragments), which include at least four of the ischemic stroke-related protein sequences listed in Table 5, at least 150 of the ischemic stroke-related protein sequences listed in Table 3, or at least 500 of the ischemic stroke-related protein sequences listed in Table 2. In particular examples, an array includes proteins that can recognize all 22 ischemic stroke-associated proteins listed in Table 5, all 82 of the ischemic stroke-related protein sequences listed in Table 4, all 190 of the ischemic stroke-related proteins listed in Table 3, or all 637 of the ischemic stroke-related proteins listed in Table 2. Such arrays can also contain any particular subset of the sequences listed in Tables 2-5. For example, an array can include probes that can recognize at least one white blood cell activation and differentiation protein, at least one protein related to hypoxia, at least one protein involved in vascular repair, and at least one protein related to a specific PBMC response to the altered cerebral microenvironment, or at least 2, at least 3, at least 5, or at least 10 proteins from each of these families. In another specific example, the array includes probes that recognize one or more of CD163; hypothetical protein FLJ22662 Laminin A motif, BST-1; FcγRI; baculoviral IAP repeat-containing protein 1; or KIAA0146. For example, the array can include a probe that recognizes CD163 and additional probes that recognize other ischemic stroke related proteins (such as any combination of at least 3 or at least 22 of those listed in Tables 2-5).

The proteins or antibodies forming the array can be directly linked to the support. Alternatively, the proteins or antibodies can be attached to the support by spacers or linkers to the solid support.

Changes in expression of ischemic stroke-related proteins can be detected using, for instance, an ischemic stroke protein-specific binding agent, which in some instances is labeled with an agent that can be detected. In certain examples, detecting a change in protein expression includes contacting a protein sample obtained from the PBMCs of a subject with an ischemic stroke protein-specific binding agent (which can be for example present on an array); and detecting whether the binding agent is bound by the sample and thereby measuring the levels of the ischemic stroke-related protein present in the sample. A difference in the level of an ischemic stroke-related protein in the sample, relative to the level of an ischemic stroke-related protein found an analogous sample from a subject who has not had an ischemic stroke, in particular examples indicates that the subject has suffered an ischemic stroke.

Array Substrate

The solid support can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567, herein incorporated by reference).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185, herein incorporated by reference). In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Particularly disclosed for preparation of arrays at this time are biaxially oriented polypropylene (BOPP) films; in addition to their durability, BOPP films exhibit a low background fluorescence.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789, herein incorporated by reference). In another example, sequences are synthesized directly onto the support to provide the desired array (see U.S. Pat. No. 5,554,501, herein incorporated by reference). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217:306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501, herein incorporated by reference).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

Detection of Nucleic Acid and Protein Molecules

The nucleic acid molecules and proteins obtained from the subject (for example from a PBMC) can contain altered levels of one or more genes associated with ischemic stroke, such as those listed in Tables 2-5. Changes in expression can be detected to evaluate a stroke, or example to determine if the subject has had an ischemic stroke, to determine the severity of the stroke, to determine the likelihood of neurological recovery of a subject who has had an ischemic stroke, to determine the appropriate therapy for a subject who has had an ischemic stroke, or combinations thereof. The present disclosure is not limited to particular methods of detection. Any method of detecting a nucleic acid molecule or protein can be used, such as physical or functional assays. For example, the level of gene activation can be quantitated utilizing methods well known in the art and those disclosed herein, such as Northern-Blots, RNase protection assays, nucleic acid or antibody probe arrays, quantitative PCR (such as TaqMan assays), dot blot assays, in-situ hybridization, or combinations thereof. In addition, proteins can be quantitated using antibody probe arrays, quantitative spectroscopic methods (for example mass spectrometry, such as surface-enhanced laser desorption/ionization (SELDI)-based mass spectrometry), or combinations thereof.

Methods for labeling nucleic acid molecules and proteins so that they can be detected are well known. Examples of such labels include non-radiolabels and radiolabels. Non-radiolabels include, but are not limited to enzymes, chemiluminescent compounds, fluorophores, metal complexes, haptens, colorimetric agents, dyes, or combinations thereof. Radiolabels include, but are not limited to, $^{125}$I and $^{35}$S. Radioactive and fluorescent labeling methods, as well as other methods known in the art, are suitable for use with the present disclosure. In one example, the primers used to amplify the subject's nucleic acids are labeled (such as with biotin, a radiolabel, or a fluorophore). In another example, the amplified nucleic acid samples are end-labeled to form labeled amplified material. For example, amplified nucleic acid molecules can be labeled by including labeled nucleotides in the amplification reactions. In another example, nucleic acid molecules obtained from a subject are labeled, and applied to an array containing oligonucleotides. In a particular example, proteins obtained from a subject are labeled and subsequently analyzed, for example by applying them to an array.

The nucleic acid molecules obtained from the subject that are associated with ischemic stroke are applied to an ischemic stroke detection array under suitable hybridization conditions to form a hybridization complex. In particular examples, the nucleic acid molecules include a label. In one example, a pre-treatment solution of organic compounds, solutions that include organic compounds, or hot water, can be applied before hybridization (see U.S. Pat. No. 5,985,567, herein incorporated by reference).

Hybridization conditions for a given combination of array and target material can be optimized routinely in an empirical manner close to the $T_m$ of the expected duplexes, thereby maximizing the discriminating power of the method. Identification of the location in the array, such as a cell, in which binding occurs, permits a rapid and accurate identification of sequences associated with ischemic stroke present in the amplified material (see below).

The hybridization conditions are selected to permit discrimination between matched and mismatched oligonucleotides. Hybridization conditions can be chosen to correspond to those known to be suitable in standard procedures for hybridization to filters and then optimized for use with the arrays of the disclosure. For example, conditions suitable for hybridization of one type of target would be adjusted for the use of other targets for the array. In particular, temperature is controlled to substantially eliminate formation of duplexes between sequences other than exactly complementary ischemic stroke-associated wild-type of mutant sequences. A variety of known hybridization solvents can be employed, the choice being dependent on considerations known to one of skill in the art (see U.S. Pat. No. 5,981,185, herein incorporated by reference).

Once the nucleic acid molecules associated with ischemic stroke from the subject have been hybridized with the oligonucleotides present in the ischemic stroke detection array, the presence of the hybridization complex can be analyzed, for example by detecting the complexes.

Detecting a hybridized complex in an array of oligonucleotide probes has been previously described (see U.S. Pat. No. 5,985,567, herein incorporated by reference). In one example, detection includes detecting one or more labels present on the oligonucleotides, the sequences obtained from the subject, or both. In particular examples, developing includes applying a buffer. In one example, the buffer is sodium saline citrate, sodium saline phosphate, tetramethylammonium chloride, sodium saline citrate in ethylenediaminetetra-acetic, sodium saline citrate in sodium dodecyl sulfate, sodium saline phosphate in ethylenediaminetetraacetic, sodium saline phosphate in sodium dodecyl sulfate, tetramethylammonium chloride in ethylenediaminetetra-acetic, tetramethylammonium chloride in sodium dodecyl sulfate, or combinations thereof. However, other suitable buffer solutions can also be used.

Detection can further include treating the hybridized complex with a conjugating solution to effect conjugation or coupling of the hybridized complex with the detection label, and treating the conjugated, hybridized complex with a detection reagent. In one example, the conjugating solution includes streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one example, the detection reagent includes enzyme-labeled fluorescence reagents or calorimetric reagents. In one specific non-limiting example, the detection reagent is enzyme-labeled fluorescence reagent (ELF) from Molecular Probes, Inc. (Eugene, Oreg.). The hybridized complex can then be placed on a detection device, such as an ultraviolet (UV) transilluminator (manufactured by UVP, Inc. of Upland, Calif.). The signal is developed and the increased signal intensity can be recorded with a recording device, such as a charge coupled device (CCD) camera (manufactured by Photometrics, Inc. of Tucson, Ariz.). In particular examples, these steps are not performed when fluorophores or radiolabels are used.

In particular examples, the method further includes quantification, for instance by determining the amount of hybridization.

Kits

The present disclosure provides for kits that can be used to evaluate a stroke, for example to determine if a subject has had an ischemic stroke, to determine the severity of the stroke, to determine the likelihood of neurological recovery of a subject who has had an ischemic stroke, to determine the appropriate therapy for a subject who has had an ischemic stroke, or combinations thereof. Such kits allow one to determine if a subject has a differential expression in ischemic stroke-related genes, such as any combination of four or more of those listed in Table 5, any combination of 150 or more of those listed in Table 3, or any combination of 500 or more of those listed in Table 2, for example any combination of at least one gene from each class of genes listed in Table 5 (such as at least 2 or at least 3 genes from each of the four classes of genes listed in Table 5).

The disclosed kits include a binding molecule, such as an oligonucleotide probe that selectively hybridizes to an ischemic stroke-related molecule that is the target of the kit. In particular examples, the oligonucleotides probes are attached to an array. In one example, the kit includes oligonucleotide probes or primers (or antibodies) that recognize any combination of at least four of the molecules in Table 5, such as at least 5, at least 10, at least 15, at least 20, or at least 22 of the ischemic stroke-related molecules listed in Table 5, such as any combination of at least 150 of the molecules in Table 3, such as at least 160, at least 170, at least 175, at least 180, at least 185, or at least 190 of the sequences listed in Table 3, such as any combination of at least 500 of the molecules in Table 2, such as at least 525, at least 550, at least 575, at least 600, at least 610, or at least 637 of the sequences listed in Table 2. In particular examples, the kit includes oligonucleotide probes or primers (or antibodies) that recognize at least one gene (or protein) from each class listed in Table 5, such as at least 2, at least 3, at least 5, or at least 10 genes from each class.

In one particular example, the kit includes oligonucleotide probes or primers (or antibodies) that recognize at least CD163; hypothetical protein FLJ22662 Laminin A motif; BST-1; FcγRI; baculoviral IAP repeat-containing protein 1; and KIAA0146. In one particular example, the kit includes oligonucleotide probes or primers (or antibodies) that recognize at least 1, at least 2, at least 3, at least 4, at least 5 or at least 6 of CD163; hypothetical protein FLJ22662 Laminin A motif; BST-1; FcγRI; baculoviral IAP repeat-containing protein 1; or KIAA0146. In another particular example, the kit includes oligonucleotide probes or primers (or antibodies) that recognize CD163, for example in combination with oligonucleotide probes or primers (or antibodies) that recognize any combination of at least three ischemic stroke related molecules listed in Tables 2-5.

In a particular example, kits include antibodies capable of binding to ischemic stroke-related proteins. Such antibodies can be present on an array.

The kit can further include one or more of a buffer solution, a conjugating solution for developing the signal of interest, or a detection reagent for detecting the signal of interest, each in separate packaging, such as a container. In another example, the kit includes a plurality of ischemic stroke-related target nucleic acid sequences for hybridization with an ischemic stroke detection array to serve as positive control. The target nucleic acid sequences can include oligonucleotides such as DNA, RNA, and peptide-nucleic acid, or can include PCR fragments.

Ischemic Stroke Therapy

The present disclosure also provides methods of reducing brain injury in a subject determined to have suffered an ischemic stroke. For example, if using the assays described above a change in expression in at least 4 of the ischemic stroke-related molecules listed in Table 5 is detected in the subject, for example at least 22 of the ischemic stroke-related molecules listed in Table 5 is detected in the subject, a treatment is selected to avoid or reduce brain injury or to delay the onset of brain injury. In another example, if using the screening methods described above a change in expression in at least 500 of the ischemic stroke-related molecules listed in Table 2 is detected in the subject, a treatment is selected to avoid or reduce brain injury or to delay the onset of brain injury. The subject then can be treated in accordance with this selection, for example by administration of one or more anticoagulant agents. In some examples, the treatment selected is specific and tailored for the subject, based on the analysis of that subject's profile for one or more ischemic stroke-related molecules.

Screening Test Agents

Based on the identification of multiple ischemic stroke-related molecules whose expression is altered following an ischemic stroke (such as those listed in Tables 2-5), the disclosure provides methods for identifying agents that can enhance, normalize, or reverse these effects. For example, the method permits identification of agents that normalize activity of an ischemic stroke-related molecule, such as a gene (or its corresponding protein) involved in vascular repair, response to hypoxia, response to altered cerebral microenvironment, or combinations thereof (see Table 5). Normalizing activity (such as the expression) of an ischemic stroke-related molecule can include decreasing activity of an ischemic stroke-related molecule whose activity is increased following an ischemic stroke, or increasing activity of an ischemic stroke-related molecule whose activity is decreased following an ischemic stroke. In another example, the method permits identification of agents that enhance the activity of an ischemic stroke-related molecule, such as an ischemic stroke-related molecule whose activity provides a protective effect to the subject following an ischemic stroke. For example, the method permits identification of agonists. In yet another example, the method permits identification of agents that decrease the activity of an ischemic stroke-related molecule, such as an ischemic stroke-related molecule whose activity results in one or more negative symptoms of ischemic stroke. For example, the method permits identification of antagonists.

In particular examples the identified agents can be used to treat a subject who has had an ischemic stroke, for example to alleviate or prevent one or more symptoms of an ischemic stroke, such as paralysis or memory loss.

The disclosed methods can be performed in vitro, for example by adding the test agent to cells in culture, or in vivo, for example by administering the test agent to a mammal (such as a human or a laboratory animal, for example a mouse, rat, dog, or rabbit). In particular examples, the method includes exposing the cell or mammal to conditions sufficient for mimicking an ischemic stroke. The one or more test agents are added to the cell culture or administered to the mammal under conditions sufficient to alter the activity of an ischemic stroke-related molecule, such as at least one of the molecules listed in Tables 2-5. Subsequently, the activity of the ischemic stroke-related molecule is determined, for example by measuring expression of one or more ischemic stroke-related molecules or by measuring an amount of biological activity of one or more ischemic stroke-related proteins. A change in the activity one or more ischemic stroke-related molecule indicates that the test agent alters the activity of an ischemic stroke-related molecule listed in Tables 2-5. In particular examples, the change in activity is determined by a comparison to a standard, such as an amount of activity present when no ischemic stroke has occurred, or an amount of activity present when an ischemic stroke has occurred, or to a control.

Any suitable compound or composition can be used as a test agent, such as organic or inorganic chemicals, including aromatics, fatty acids, and carbohydrates; peptides, including monoclonal antibodies, polyclonal antibodies, and other specific binding agents; phosphopeptides; or nucleic acid molecules. In a particular example, the test agent includes a random peptide library (for example see Lam et al., *Nature* 354:824, 1991), random or partially degenerate, directed phosphopeptide libraries (for example see Songyang et al., *Cell* 72:767-78, 1993). A test agent can also include a complex mixture or "cocktail" of molecules.

Therapeutic agents identified with the disclosed approaches can be used as lead compounds to identify other agents having even greater desired activity. In addition, chemical analogs of identified chemical entities, or variants, fragments, or fusions of peptide test agents, can be tested for their ability to alter activity of an ischemic stroke-related molecule using the disclosed assays. Candidate agents can be tested for safety in animals and then used for clinical trials in animals or humans.

In one example, the method is an in vitro assay. For example, cells, such as cells that can provide a model of what happens in vivo following an ischemic stroke, are cultured under conditions sufficient for mimicking an ischemic stroke, such as hypoxia, hypoglycemia, or combinations thereof. Simultaneously or at a time thereafter, one or more test agents are incubated with the cells under conditions sufficient for the test agent to have the desired effect on the cell, for example to alter (such as normalize) the activity of a ischemic stroke-related molecule. In particular examples, the test agent has the desired effect on more than one ischemic stroke-related molecule.

Examples of cells that can be used include, but are not limited to: PBMCs, endothelial cells, neuronal cells, or combinations thereof. Methods of isolating PBMCs from a subject are disclosed herein. Neuronal cells and endothelial cells can also be obtained from a subject, such as a mammal, and grown as a primary culture using standard methods. For example, endothelial cells can be obtained from umbilical cord tissue (for example see Ulrich-Merzenich et al., *In Vitro Cellular & Developmental Biology-Animal*, 38: 265-72, 2002); coronary arteries (Dame et al., *In Vitro Cellular & Developmental Biology-Animal*, 39:402-6, 2003); or lung tissue (for example see Dong et al., *Arteriosclerosis, Thrombosis, and Vascular Biology*, 17:1599-604, 1997). For example, neuronal cells can be obtained from mammalian brain tissue (for example see Shevtsova et al., *Exp. Physiol.* 90:53-9, 2005 and Buse et al., *Brain Res.* 283:221-34, 1983). In one example, established neuronal or endothelial tissue culture cell lines are used, such as those available from American Type Culture Collection (ATCC) and other commercial sources. For example, rat PC12 pheochromocytoma neurosecretory cell line (ATCC No. CRL-1721), human neuronal HCN-2 cells (ATCC No. CRL-10742), the rat neuronal RSC96 cell line (CRL-2765), human HAAE-2 endothelial cells (ATCC No. CRL-2473), human HPAE-26 endothelial cells (ATCC No. CRL-2598), human aortic endothelial cells (Clonetics), and bovine FBHE endothelial cells (ATCC No. CRL-1395) are particular examples of cell lines that can be used. However one skilled in the art will appreciate that other cell lines can be used.

Methods of providing conditions sufficient for mimicking an ischemic stroke in vitro are known in the art. For example, cells can be exposed to hypoxic conditions (low oxygen) by culturing the cells in an atmosphere controlled-culture chamber (for example a chamber from Bellco Glass [Vineland, N.J.]; a modular hypoxia chamber [Billups-Rothenberg]; an Espec [Grand Rapids, Mich.]; or BIO-LABO [Juji Field, Tokyo, Japan]. A particular example of hypoxic conditions is a chamber containing a gas mixture of 94% $N_2$, 5% $CO_2$, and 1% $O_2$. Cells are generally grown at 37° C. The amount of time the cells are exposed to hypoxic conditions can vary. In particular examples, cells are exposed to hypoxic conditions for at least 10 minutes, such as at least 30 minutes, at least 1 hour, at least 6 hours, at least 12 hours, or even at least 24 hours. In one example, hypoxic conditions are used to identify free radical scavenger agents.

Another method that can be used to mimic an ischemic stroke is to expose the cells to hypoglycemic conditions (low glucose). Hypoglycemia (such as <30 mg glucose/dl) can result from ischemia (for example using the conditions described above), or can be induced by culturing cells in growth medium that does not contain added glucose. Cells are generally grown at 37° C. The amount of time the cells are exposed to hypoglycemic conditions (deprived of glucose) can vary. In particular examples, cells are exposed to hypoglycemic conditions for at least 1 hour, such as at least 4 hours, at least 6 hours, at least 12 hours, at least 24 hours, at least 48 hours, or even at least 72 hours. In some examples, the hypoglycemic conditions are combined with hypoxic conditions.

One or more test agents are incubated with the cells under conditions sufficient for the test agent to have the desired effect on the cell. The agent can be added at a time subsequent to mimicking an ischemic stroke, or at substantially the same time as mimicking an ischemic stroke. In one example, the agent is added at least 30 minutes after mimicking an ischemic stroke, such as at least 1 hour, at least 2 hours, at least 6 hours, at least 24 hours, at least 72 hours, at least 7 days, at least 14 days, at least 30 days, at least 60 days or even at least 90 days after mimicking an ischemic stroke.

In another example, the method is an in vivo assay. For example, agents identified as candidates in the in vitro assay can be tested in vivo for their ability to alter (such as normalize) the activity of a ischemic stroke-related molecule (such as one or more of those listed in Tables 2-5). In particular examples, the mammal has had an ischemic stroke or has been exposed to conditions that induce an ischemic stroke. Simultaneously or at a time thereafter, one or more test agents are administered to the subject under conditions sufficient for the test agent to have the desired effect on the subject, for example to alter (such as normalize) the activity of an ischemic stroke-related molecule or a pattern of ischemic stroke-related molecules. In particular examples, the test agent has the desired effect on more than one ischemic stroke-related molecule.

Methods of providing conditions sufficient for inducing an ischemic stroke in vivo are known in the art. For example, ischemic stroke can be induced in a mammal by occlusion of the middle cerebral artery (MCA) under anesthesia. Ischemic stroke can also be induced in a mammal (such as a rat), for example by three-vessel (bilateral vertebral and unilateral common carotid artery) occlusion (3-VO) to induce unilaterally accentuated brain hypoperfusion under anesthesia (for example using the method described in Busch et al., *J. Cereb. Blood Flow Metab.* 23:621-8, 2003) or by the four-vessel occlusion (4-VO) method to induce transient forebrain ischemia. In another example, the subject is exposed hypoxic conditions. For example, a mammal can be exposed to sublethal hypoxia conditions, such as 11% oxygen for 2 hours. In another example, the right carotid artery is ligated and mammal exposed to 8% oxygen for 2 hours.

One or more test agents are administered to the subject under conditions sufficient for the test agent to have the desired effect on the subject. Any appropriate method of administration can be used, such as intravenous, intramuscular, or transdermal. The agent can be administered at a time subsequent to the ischemic stroke, or at substantially the same time as the ischemic stroke. In one example, the agent is added at least 30 minutes after the ischemic stroke, such as at least 1 hour, at least 2 hours, at least 6 hours, at least 24 hours, at least 72 hours, at least 7 days, at least 14 days, at least 30 days, at least 60 days or even at least 90 days after the ischemic stroke.

The effect on the one or more test agents on the activity of one or more ischemic stroke-related molecules can be determined using methods known in the art. For example, the effect on expression of one or more ischemic stroke-related genes can be determined using the arrays and methods disclosed herein. For example, RNA can be isolated from the cultured cells exposed to the test agent, or from cells obtained from a subject (such as PBMCs) administered the test agent. The isolated RNA can be labeled and exposed to an array containing one or more nucleic acid molecules (such as a primer or probe) that can specifically hybridize to one or more pre-selected ischemic stroke-related genes, such at least 1, at least 2, or at least 3 of those listed in Tables 2-5, or to a pre-selected pattern of such genes that is associated with ischemic stroke. In a particular example, the one or more pre-selected ischemic stroke-related genes include at least one gene involved in vascular repair, at least one response to hypoxia gene, at least one response to altered cerebral microenvironment gene, or combinations thereof (for example see Table 5). In another example, proteins are isolated from the cultured cells exposed to the test agent, or from cells obtained from a subject (such as PBMCs) administered the test agent. The isolated proteins can be analyzed to determine amounts of expression or biological activity of one or more ischemic stroke-related proteins, such at least 1, at least 2, or at least 3 of those listed in Tables 2-5, or a pattern of upregulation or downregulation of pre-identified or pre-selected proteins. In a particular example, the one or more pre-selected ischemic stroke-related proteins include at least one protein involved in vascular repair, at least one response to hypoxia protein, at least one response to altered cerebral microenvironment protein, or combinations thereof (for example see Table 5). In a particular example, mass spectrometry is used to analyze the proteins.

In particular examples, differential expression of an ischemic stroke-related molecule is compared to a standard or a control. One example of a control includes the amount of activity of an ischemic stroke-related molecule present or expected in a subject who has not had an ischemic stroke, wherein an increase or decrease in activity in a test sample of an ischemic stroke-related molecule (such as those listed in Tables 2-5) compared to the control indicates that the test agent alters the activity of at least one ischemic stroke-related molecule. Another example of a control includes the amount of activity of an ischemic stroke-related molecule present or expected in a subject who has had an ischemic stroke, wherein an increase or decrease in activity in a test sample (such as gene expression, amount of protein, or biological activity of a protein) of an ischemic stroke-related molecule (such as those listed in Tables 2-5) compared to the control indicates that the test agent alters the activity of at least one ischemic stroke-related molecule. Detecting differential expression can include measuring a change in gene expression, measuring an amount of protein, or determining an amount of the biological activity of a protein present.

In particular examples, test agents that altered the activity of an ischemic stroke-related molecule are selected.

The disclosure is further illustrated by the following non-limiting Examples.

Example 1

Isolation of Samples

This example describes methods used to obtain RNA from control subjects (subjects who had not previously had a stroke) and subjects who suffered an ischemic stroke within the previous 72 hours.

A cohort of elderly volunteers was obtained and their stroke risk factors recorded, including a history of hypertension, smoking, diabetes mellitus and heart disease. Approximately 30 milliliters of blood was drawn into four yellow top ACD A tubes (ACD Acid Citrate Dextrose A, 22.0 g/L Trisodium Citrate, 8.0 g/L Citric Acid, 24.5 g/L Dextrose, BD Franklin Lakes, N.J.) by aseptic antecubital fossa venipuncture. PBMC isolation was completed within two hours.

Acute stroke patients admitted to the National Institutes of Health Stroke Program at Suburban Hospital in Bethesda, Md. underwent aseptic antebrachial venipuncture followed by withdrawal of 30 ml of blood as described above. Blood samples were drawn within 72 hours of stroke onset. The blood samples were processed for RNA within two hours of collection.

Table 1 lists the demographic features of the patients and controls in the index cohort (n=38) and the patients and controls in the validation (test) cohort (n=19). The two index groups are reasonably comparable in terms of age sex and pre-morbid risk factors consistent with a community based stroke population.

TABLE 1

Demographics of Patients and Controls

| Factor | | Index Cohort | | Test Cohort | |
|---|---|---|---|---|---|
| | | Patients | Controls | Patients | Controls |
| Number | | 19 | 19 | 9 | 10 |
| Age (years) | | 75.7 ± 15.1 | 66.0 ± 11.5 | 79.6 ± 8.1 | 67.6 ± 16.1 |
| Sex | Female | 7 (37) | 13 (68) | 4 (44) | 6 (60) |
| Race | Caucasian | 18 (95) | 13 (68) | 8 (89) | 7 (70) |
| | African American | 1 (5) | 5 (26) | 1 (11) | 2 (20) |
| | Asian | 0 (0) | 1 (5) | 0 (0) | 1 (10) |
| Risk Factors | Hypertension | 12 (63) | 5 (26) | 5 (56) | 4 (40) |
| | Diabetes | 1 (5) | 0 (0) | 1 (11) | 1 (10) |
| | Smoking | 7 (37) | 7 (37) | 5 (56) | 2 (20) |
| | Coronary artery disease | 4 (21) | 1 (5) | 3 (33) | 1 (10) |
| | Framingham risk score | 16.2 ± 7.4 | 9.8 ± 5.6 | 18.6 ± 2.5 | 12.2 ± 8.4 |
| Stroke-Related | NIHSS score* | 3.7 ± 5.1 | | 5.9 ± 6.2 | |
| | Time to blood draw (hours) | 32.4 ± 17.8 | | 53.3 ± 39.7 | |

Figures are numbers (%) for groups and mean ± SD for continuous factors.
*NIHSS - National Institutes of Health Stroke Scale.

Acute stroke was confirmed by magnetic resonance imaging studies including diffusion weighted imaging (DWI) and perfusion imaging. Stroke risk factors were recorded on each patient and volunteer according to the Framingham risk profile (see Wolf et al., Stroke 22:312-8, 1991). Stroke severity was determined by serial neurological examination and by the National Institutes of Health Stroke Scale (NIHSS) score (see Brott et al., Stroke 20:871-5, 1989).

RNA was isolated from PBMCs as follows. Total RNA (5-15 μg) was extracted from PBMCs separated from whole blood using a Density Gradient tube (Uni-Sep, Novamed, Jerusalem, Israel) as follows: 20-30 ml ACD anti-coagulated blood was diluted with an equal volume of phosphate buffered saline (PBS) and added to the density gradient tube, followed by centrifugation at 1000 g for 30 minutes. After centrifugation, the PBMC layer was removed.

RNA was extracted using RNeasy Mini Kit (Qiagen Cat. # 75162, Valencia, Calif.), as per the manufacturer's protocol. Briefly, harvested PBMCs are diluted 1:1 with PBS and centrifuged for 10 minutes at 4000 rpm. The resulting supernatant was discarded and the pellet resuspended in 600 μl RLT buffer (1 ml buffer+10 μl 2-β-mercaptoethanol). The sample was homogenized by passing the lysate 5-10 times through 20-G (French) needle fitted to a syringe. Cells were resuspended in 600 μl of DEPC-H$_2$O diluted in 70% EtOH and was loaded onto an RNeasy mini spin column fitted with a 2-ml collection tube. The sample was twice centrifuged at 14,000 rpm for 15 seconds. The RNeasy column was transferred to a new 2 ml collection tube and 500 μl of RPE buffer added followed by centrifugation at 14,000 rpm for 15 seconds. RPE buffer (500 μl) was added and the sample centrifuged at 10,000 rpm for 2 minutes. The RNeasy column was then transferred into a new 1.5 ml collection tube and RNA free water (30 μl) directly added to the RNase membrane followed by further centrifugation at 10,000 rpm for 1 minute. This was repeated and the extracted RNA stored at −80° C.

Example 2

RNA Labeling

This example describes methods used to label the RNA obtained in Example 1. However, one skilled in the art will appreciate that other labels and methods can be used.

RNA obtained from PBMCs was biotin-labeled and cleaned according to Affymetrix guidelines for Human Genome 133A arrays. Briefly, the Enzo BioArray HighYield RNA Transcript Labeling Kit3 (Affymetrix, P/N 900182) was used for generating labeled cRNA target. Template cDNA and the other reaction components were added to RNase-free microfuge tubes. To avoid precipitation of DTT, reactions were at room temperature while additions were made. After adding all reagents, the tube was incubated are a 37° C. for 4 to 5 hours, gently mixing the contents of the tube every 3045 minutes during the incubation.

To ensure the quality of the initial isolated total RNA, DNase was used to remove contaminant DNA from the sample. In addition, Northern blot followed by optical density analysis was used to determine the concentration of the RNA band.

If the total RNA concentration was >5 μg, the RNA was used for subsequent gene chip hybridization as per the manufacturer's protocol.

Example 3

Microarray Hybridization and Statistical Analysis

Coded mRNA samples were analyzed using the Affymetrix GeneChipR Human Genome U133A chips that include 22,283 gene probes (around 19,000 genes) of the best characterized human genes. Microarrays were scanned (Axon scanner, Axon Instruments Inc, CA), and images were analyzed using GenePix image analysis software (Axon Instruments Inc, CA) allowing for gene spot fluorescent quantification following subtraction of the surrounding background fluorescent signal within the Affymetrix MASS gene chip analysis suite with production of .CEL, and .DAT output files. The .CDF file or annotation file for the Affymetrix HU133A chip and the .CEL files, containing the scanned gene expression information, were the only data files used in all subsequent analyses.

For the data analysis, .CEL files of 19 patients and 19 controls were used following exclusion from analysis of one chip in each of the index patient and control groups due to unsatisfactory hybridization (see Irizarry et al., The Analysis of Gene Expression Data. New York: Springer, 2003). The analysis was completed using the Bioconductor applications of the R programming language and implemented on a 64-bit operating system (SGI Octane 14000 MIPS 600 MHz CPU running Irix 6.5.15) due to the large dataset for analysis (Moore et al, 32 bit architecture—a severe bio-informatics limitation. NHLBI Symposium From Genome to Disease. 2003, Bethesda, Md.: 64). Sample RNA degradation during processing was tightly distributed and uniform across all chips.

Quantile normalization was performed simultaneously on the .CEL dataset (stroke patients, n=19, controls, n=19).

Following normalization, expression levels for each gene were calculated using the perfect match array probes and a robust median polish technique after background correction and $\log_2$ transformation (Irizarry et al., *The Analysis of Gene Expression Data*. New York: Springer, 2003). The resulting expression set was compared in a univariate manner between the stroke patients and control group using parametric testing (t-test). The uncorrected p-value were assigned a cutoff threshold value of significance of <0.05. Subsequent multiple comparison correction was performed using Bonferroni and false discovery techniques (Benjamini and Yekutieli, *The Annals of statistics* 29:1165-88, 2001). The effects of various multiple comparison correction techniques are shown in FIG. 1.

The uncorrected significant gene expression set was further analyzed using permutation analysis of Westfall and Young (*Resampling-based multiple testing: Examples and methods for p-value adjustment*. New York: John Wiley & Sons, 1993). Hierarchical cluster analysis was performed on the gene subset found to be significantly different between stroke patients and controls using the method of Eisen et al. where each gene was pair-wise correlated by calculation of a distance matrix using a Euclidean metric (*Proc. Natl. Acad. Sci.* 95:14863-8, 1998). The distance matrix then formed the basis for hierarchical clustering. Gene annotation and ontology were determined using the Affymetrix on-line NetAffix suite together with subsequent literature searches, allowing categorization of a gene listing into molecular function, cellular function and biological function.

Using the PAM algorithm (Prediction Analysis for Microarrays) the ability of the index set to separate prospectively obtained samples from ten stroke patients and ten controls was examined (Tibshirani et al., *Proc. Natl. Acad. Sci.* 90:6567-72, 2002). The arrays of 9 patients and 10 controls were used. In one stroke case, the hybridization was not of sufficient quality to be included.

Without multiple comparison correction, 5060 genes were significantly different in the dataset. The Benjamini and Yekutieli correction resulted in 771 significant gene probes (Table 2), which represent 637 genes. This approach seeks to limit the false discovery rate (the proportion of non-differentiated genes among all those genes declared significantly different) to 5%. As shown in Table 2, several genes were upregulated (positive T-statistic, such as a value that is at least 3.77) or downregulated (negative t-statistic, such as a value that is less than −3.76, such as less than −3.77) following an ischemic stroke. In addition, several genes not previously associated with ischemic stroke, such as CD163; hypothetical protein FLJ22662 Laminin A motif; bone marrow stromal cell antigen 1/CD157; Fc fragment of IgG, high affinity Ia, receptor for (CD64); baculoviral IAP repeat-containing protein 1; and KIAA0146, were identified. The probe sequences associated with the Affymetrix ID Nos. are herein incorporated by reference.

TABLE 2

Ischemic stroke related-genes using Benjamini and Yekutieli correction.

| Affy ID No. | t-statistic* | Gene Name | UniGene ID No. |
|---|---|---|---|
| 218454_at | 7.89390463 | hypothetical protein FLJ22662 | 178470 |
| 215049_x_at | 7.86959913 | CD163 antigen | 74076 |
| 203645_s_at | 7.79274287 | CD163 antigen | 74076 |
| 211404_s_at | 7.61929825 | amyloid beta (A4) precursor-like protein 2 | 279518 |
| 206120_at | 7.61303715 | CD33 antigen (gp67) | 83731 |
| 208771_s_at | 7.4480951 | leukotriene A4 hydrolase | 81118 |
| 210872_x_at | 7.29576739 | growth arrest-specific 7 | 226133 |
| 201328_at | 7.19607698 | v-ets erythroblastosis virus E26 oncogene homolog 2 (avian) | 292477 |
| 222173_s_at | 7.01811369 | TBC1 domain family, member 2 | 371016 |
| 211612_s_at | 6.71007614 | interleukin 13 receptor, alpha 1 | 285115 |
| 211067_s_at | 6.66328089 | growth arrest-specific 7 | 226133 |
| 211368_s_at | 6.65646046 | caspase 1, apoptosis-related cysteine protease (interleukin 1, beta, convertase) | 2490 |
| 219788_at | 6.6357632 | paired immunoglobin-like type 2 receptor alpha | 122591 |
| 202896_s_at | 6.63433745 | protein tyrosine phosphatase, non-receptor type substrate 1 | 156114 |
| 221210_s_at | 6.63079363 | N-acetylneuraminate pyruvate lyase (dihydrodipicolinate synthase) | 64896 |
| 204924_at | 6.60026287 | toll-like receptor 2 | 439608 |
| 206488_s_at | 6.54747468 | CD36 antigen (collagen type I receptor, thrombospondin receptor) | 443120 |
| 208146_s_at | 6.53595206 | carboxypeptidase, vitellogenic-like | 95594 |
| 213006_at | 6.50588342 | KIAA0146 protein | 381058 |
| 208923_at | 6.46904449 | cytoplasmic FMR1 interacting protein 1 | 26704 |
| 208702_x_at | 6.46198549 | amyloid beta (A4) precursor-like protein 2 | 279518 |
| 204452_s_at | 6.45273495 | frizzled homolog 1 (*Drosophila*) | 94234 |
| 205715_at | 6.43160146 | bone marrow stromal cell antigen 1 | 169998 |
| 216942_s_at | 6.42353873 | CD58 antigen, (lymphocyte function-associated antigen 3) | 75626 |
| 218217_at | 6.41930598 | likely homolog of rat and mouse retinoid-inducible serine carboxypeptidase | 431107 |
| 212192_at | 6.41402934 | hypothetical protein BC013764 | 109438 |

TABLE 2-continued

Ischemic stroke related-genes using Benjamini and Yekutieli correction.

| Affy ID No. | t-statistic* | Gene Name | UniGene ID No. |
|---|---|---|---|
| 200868_s_at | 6.39211608 | zinc finger protein 313 | 144949 |
| 202912_at | 6.38896329 | adrenomedullin | 441047 |
| 207691_x_at | 6.37169995 | ectonucleoside triphosphate diphosphohydrolase 1 | 444105 |
| 209124_at | 6.322399 | myeloid differentiation primary response gene (88) | 82116 |
| 204620_s_at | 6.31071007 | chondroitin sulfate proteoglycan 2 (versican) | 434488 |
| 203535_at | 6.29981025 | S100 calcium binding protein A9 (calgranulin B) | 112405 |
| 202878_s_at | 6.29001183 | complement component 1, q subcomponent, receptor 1 | 97199 |
| 204249_s_at | 6.28630536 | LIM domain only 2 (rhombotin-like 1) | 283063 |
| 208872_s_at | 6.26653125 | polyposis locus protein 1 | 173119 |
| 205603_s_at | 6.25337908 | diaphanous homolog 2 (*Drosophila*) | 226483 |
| 208818_s_at | 6.20310945 | catechol-O-methyltransferase | 240013 |
| 205158_at | 6.20094021 | ribonuclease, RNase A family, 4 | 283749 |
| 200765_x_at | 6.19288966 | catenin (cadherin-associated protein), alpha 1, 102 kDa | 254321 |
| 220615_s_at | 6.13260793 | hypothetical protein FLJ10462 | 134497 |
| 202897_at | 6.1313157 | protein tyrosine phosphatase, non-receptor type substrate 1 | 156114 |
| 204222_s_at | 6.12453094 | GLI pathogenesis-related 1 (glioma) | 511765 |
| 201743_at | 6.11554977 | CD14 antigen | 75627 |
| 211744_s_at | 6.05217577 | CD58 antigen, (lymphocyte function-associated antigen 3) | 75626 |
| 207168_s_at | 6.04197964 | H2A histone family, member Y | 75258 |
| 220034_at | 6.04155844 | interleukin-1 receptor-associated kinase 3 | 268552 |
| 204099_at | 6.02751709 | SWI/SNF related, matrix associated, actin dependent regulator of chromatin, subfamily d, member 3 | 444445 |
| 212335_at | 6.01677891 | glucosamine (N-acetyl)-6-sulfatase (Sanfilippo disease IIID) | 334534 |
| 211135_x_at | 6.01231784 | leukocyte immunoglobulin-like receptor, subfamily B (with TM and ITIM domains), member 3 | 511766 |
| 203127_s_at | 5.98628713 | serine palmitoyltransferase, long chain base subunit 2 | 59403 |
| 201041_s_at | 5.97525939 | dual specificity phosphatase 1 | 171695 |
| 209949_at | 5.97496326 | neutrophil cytosolic factor 2 (65 kDa, chronic granulomatous disease, autosomal 2) | 949 |
| 203922_s_at | 5.95791758 | cytochrome b-245, beta polypeptide (chronic granulomatous disease) | 88974 |
| 200838_at | 5.95626946 | cathepsin B | 135226 |
| 210844_x_at | 5.93419339 | catenin (cadherin-associated protein), alpha 1, 102 kDa | 254321 |
| 200886_s_at | 5.905732 | phosphoglycerate mutase 1 (brain) | 447492 |
| 208949_s_at | 5.88800393 | lectin, galactoside-binding, soluble, 3 (galectin 3) | 411701 |
| 211284_s_at | 5.87237505 | granulin | 180577 |
| 210992_x_at | 5.78142217 | Fc fragment of IgG, low affinity IIa, receptor for (CD32) | 352642 |
| 204860_s_at | 5.76755994 | *Homo sapiens* transcribed sequence with strong similarity to protein sp: Q13075 (*H. sapiens*) BIR1_HUMAN Baculoviral IAP repeat-containing protein 1 (Neuronal apoptosis inhibitory protein) | 508565 |
| 212788_x_at | 5.75081118 | ferritin, light polypeptide | 433670 |
| 211776_s_at | 5.7448982 | erythrocyte membrane protein band 4.1-like 3 | 103839 |
| 221731_x_at | 5.74075036 | chondroitin sulfate proteoglycan 2 (versican) | 434488 |
| 210225_x_at | 5.74059556 | leukocyte immunoglobulin-like receptor, subfamily B (with TM and ITIM domains), member 3 | 511766 |
| 218404_at | 5.73126746 | sorting nexin 10 | 418132 |
| 214511_x_at | 5.7139856 | Fc fragment of IgG, high affinity Ia, receptor for (CD64) | 77424 |
| 200764_s_at | 5.67242227 | catenin (cadherin-associated protein), alpha 1, 102 kDa | 254321 |
| 210904_s_at | 5.66794891 | interleukin 13 receptor, alpha 1 | 285115 |
| 201200_at | 5.64946077 | cellular repressor of E1A-stimulated genes | 5710 |
| 209189_at | 5.64912247 | v-fos FBJ murine osteosarcoma viral oncogene homolog | 25647 |
| 202943_s_at | 5.6217726 | N-acetylgalactosaminidase, alpha- | 75372 |
| 201329_s_at | 5.60980712 | v-ets erythroblastosis virus E26 oncogene homolog 2 (avian) | 292477 |
| 200678_x_at | 5.59206951 | granulin | 180577 |
| 200839_s_at | 5.59110282 | cathepsin B | 135226 |
| 204053_x_at | 5.58890981 | phosphatase and tensin homolog (mutated in multiple advanced cancers 1) | 253309 |
| 204759_at | 5.57510891 | chromosome condensation 1-like | 27007 |
| 217897_at | 5.56972714 | FXYD domain containing ion transport regulator 6 | 410748 |
| 203973_s_at | 5.56911715 | KIAA0146 protein | 381058 |
| 210951_x_at | 5.54846557 | RAB27A, member RAS oncogene family | 298530 |

TABLE 2-continued

Ischemic stroke related-genes using Benjamini and Yekutieli correction.

| Affy ID No. | t-statistic* | Gene Name | UniGene ID No. |
|---|---|---|---|
| 216041_x_at | 5.5475628 | granulin | 180577 |
| 208454_s_at | 5.54191982 | plasma glutamate carboxypeptidase | 197335 |
| 209970_x_at | 5.52920792 | caspase 1, apoptosis-related cysteine protease (interleukin 1, beta, convertase) | 2490 |
| 204646_at | 5.50217863 | dihydropyrimidine dehydrogenase | 1602 |
| 202990_at | 5.49766192 | phosphorylase, glycogen; liver (Hers disease, glycogen storage disease type VI) | 282417 |
| 218606_at | 5.4924926 | zinc finger, DHHC domain containing 7 | 9725 |
| 219316_s_at | 5.47793995 | chromosome 14 open reading frame 58 | 267566 |
| 207574_s_at | 5.47094508 | growth arrest and DNA-damage-inducible, beta | 110571 |
| 212807_s_at | 5.46295198 | sortilin 1 | 394609 |
| 214875_x_at | 5.46291913 | amyloid beta (A4) precursor-like protein 2 | 279518 |
| 202446_s_at | 5.45795408 | phospholipid scramblase 1 | 348478 |
| 210784_x_at | 5.416225 | leukocyte immunoglobulin-like receptor, subfamily B (with TM and ITIM domains), member 3 | 511766 |
| 203561_at | 5.4154987 | Fc fragment of IgG, low affinity IIa, receptor for (CD32) | 352642 |
| 210152_at | 5.40888799 | leukocyte immunoglobulin-like receptor, subfamily B (with TM and ITIM domains), member 4 | 67846 |
| 210427_x_at | 5.374221 | annexin A2 | 462864 |
| 212830_at | 5.37395389 | EGF-like-domain, multiple 5 | 236216 |
| 204169_at | 5.36588724 | IMP (inosine monophosphate) dehydrogenase 1 | 317095 |
| 209500_x_at | 5.34575265 | tumor necrosis factor (ligand) superfamily, member 13 | 54673 |
| 201432_at | 5.33693741 | catalase | 395771 |
| 215646_s_at | 5.33373927 | chondroitin sulfate proteoglycan 2 (versican) | 434488 |
| 201422_at | 5.33217618 | interferon, gamma-inducible protein 30 | 14623 |
| 204112_s_at | 5.33018103 | histamine N-methyltransferase | 42151 |
| 214318_s_at | 5.32431367 | hypothetical protein CG003 | 390874 |
| 204588_s_at | 5.32319243 | solute carrier family 7 (cationic amino acid transporter, y+ system), member 7 | 194693 |
| 211366_x_at | 5.32286549 | caspase 1, apoptosis-related cysteine protease (interleukin 1, beta, convertase) | 2490 |
| 217865_at | 5.27748545 | ring finger protein 130 | 155718 |
| 211133_x_at | 5.26677423 | leukocyte immunoglobulin-like receptor, subfamily B (with TM and ITIM domains), member 3 | 511766 |
| 209091_s_at | 5.26607942 | SH3-domain GRB2-like endophilin B1 | 136309 |
| 209474_s_at | 5.2656896 | ectonucleoside triphosphate diphosphohydrolase 1 | 444105 |
| 209514_s_at | 5.25717561 | RAB27A, member RAS oncogene family | 298530 |
| 211571_s_at | 5.25409403 | chondroitin sulfate proteoglycan 2 (versican) | 434488 |
| 201426_s_at | 5.25332759 | vimentin | 435800 |
| 209069_s_at | 5.23594128 | H3 histone, family 3B (H3.3B) | 180877 |
| 208130_s_at | 5.23289975 | thromboxane A synthase 1 (platelet, cytochrome P450, family 5, subfamily A) | 444510 |
| 220990_s_at | 5.22930546 | likely ortholog of rat vacuole membrane protein 1 | 166254 |
| 210314_x_at | 5.22262249 | tumor necrosis factor (ligand) superfamily, member 13 | 54673 |
| 203140_at | 5.21224928 | B-cell CLL/lymphoma 6 (zinc finger protein 51) | 155024 |
| 205147_x_at | 5.20456789 | neutrophil cytosolic factor 4, 40 kDa | 196352 |
| 210101_x_at | 5.19857938 | SH3-domain GRB2-like endophilin B1 | 136309 |
| 205896_at | 5.19850838 | solute carrier family 22 (organic cation transporter), member 4 | 441130 |
| 206130_s_at | 5.19713599 | asialoglycoprotein receptor 2 | 1259 |
| 211367_s_at | 5.18249106 | caspase 1, apoptosis-related cysteine protease (interleukin 1, beta, convertase) | 2490 |
| 217521_at | 5.1760536 | histidine ammonia-lyase | 190783 |
| 212501_at | 5.16612621 | CCAAT/enhancer binding protein (C/EBP), beta | 99029 |
| 218013_x_at | 5.16025276 | dynactin 4 (p62) | 328865 |
| 209188_x_at | 5.1523164 | down-regulator of transcription 1, TBP-binding (negative cofactor 2) | 348418 |
| 202670_at | 5.15097523 | mitogen-activated protein kinase kinase 1 | 132311 |
| 217492_s_at | 5.14879874 | phosphatase and tensin homolog (mutated in multiple advanced cancers 1), pseudogene 1 | 493716 |
| 206600_s_at | 5.14522932 | solute carrier family 16 (monocarboxylic acid transporters), member 5 | 90911 |
| 208959_s_at | 5.13849248 | thioredoxin domain containing 4 (endoplasmic reticulum) | 154023 |
| 209073_s_at | 5.1251219 | numb homolog (*Drosophila*) | 445301 |
| 206237_s_at | 5.11823604 | neuregulin 1 | 172816 |
| 209185_s_at | 5.11676697 | insulin receptor substrate 2 | 143648 |
| 211702_s_at | 5.09810016 | ubiquitin specific protease 32 | 436133 |
| 200742_s_at | 5.09255723 | ceroid-lipofuscinosis, neuronal 2, late infantile (Jansky-Bielschowsky disease) | 429658 |
| 214449_s_at | 5.08839258 | ras homolog gene family, member Q | 442989 |

TABLE 2-continued

Ischemic stroke related-genes using Benjamini and Yekutieli correction.

| Affy ID No. | t-statistic* | Gene Name | UniGene ID No. |
|---|---|---|---|
| 204834_at | 5.07009362 | fibrinogen-like 2 | 351808 |
| 204619_s_at | 5.06774454 | chondroitin sulfate proteoglycan 2 (versican) | 434488 |
| 208926_at | 5.06247837 | sialidase 1 (lysosomal sialidase) | 118721 |
| 201944_at | 5.0610548 | hexosaminidase B (beta polypeptide) | 69293 |
| 202727_s_at | 5.05203162 | interferon gamma receptor 1 | 180866 |
| 211676_s_at | 5.0386297 | interferon gamma receptor 1 | 180866 |
| 204493_at | 5.03178215 | BH3 interacting domain death agonist | 300825 |
| 219015_s_at | 5.03010765 | uncharacterized hematopoietic stem/progenitor cells protein MDS031 | 110853 |
| 209397_at | 5.03002491 | malic enzyme 2, NAD(+)-dependent, mitochondrial | 75342 |
| 217741_s_at | 5.02535951 | zinc finger protein 216 | 406096 |
| 201044_x_at | 5.01624832 | dual specificity phosphatase 1 | 171695 |
| 219694_at | 5.013375 | hypothetical protein FLJ11127 | 155085 |
| 201127_s_at | 5.00643448 | ATP citrate lyase | 387567 |
| 209304_x_at | 5.00154395 | growth arrest and DNA-damage-inducible, beta | 110571 |
| 211395_x_at | 4.99850312 | Fc fragment of IgG, low affinity IIb, receptor for (CD32) | 126384 |
| 205786_s_at | 4.99689814 | integrin, alpha M (complement component receptor 3, alpha; also known as CD11b (p170), macrophage antigen alpha polypeptide) | 172631 |
| 212268_at | 4.99395229 | seine (or cysteine) proteinase inhibitor, clade B (ovalbumin), member 1 | 381167 |
| 202787_s_at | 4.99061446 | mitogen-activated protein kinase-activated protein kinase 3 | 234521 |
| 203888_at | 4.98963325 | thrombomodulin | 2030 |
| 221841_s_at | 4.98297365 | Kruppel-like factor 4 (gut) | 376206 |
| 201888_s_at | 4.97738085 | interleukin 13 receptor, alpha 1 | 285115 |
| 200785_s_at | 4.95578962 | low density lipoprotein-related protein 1 (alpha-2-macroglobulin receptor) | 162757 |
| 203167_at | 4.9520306 | tissue inhibitor of metalloproteinase 2 | 6441 |
| 201193_at | 4.94983228 | isocitrate dehydrogenase 1 (NADP+), soluble | 11223 |
| 208018_s_at | 4.94368736 | hemopoietic cell kinase | 89555 |
| 216202_s_at | 4.91295079 | serine palmitoyltransferase, long chain base subunit 2 | 59403 |
| 212820_at | 4.91065301 | rabconnectin-3 | 200828 |
| 218092_s_at | 4.91053386 | HIV-1 Rev binding protein | 352962 |
| 207654_x_at | 4.89959607 | down-regulator of transcription 1, TBP-binding (negative cofactor 2) | 348418 |
| 203746_s_at | 4.89297035 | holocytochrome c synthase (cytochrome c heme-lyase) | 211571 |
| 207704_s_at | 4.89274931 | growth arrest-specific 7 | 226133 |
| 222218_s_at | 4.89264688 | paired immunoglobin-like type 2 receptor alpha | 122591 |
| 207980_s_at | 4.88126247 | Cbp/p300-interacting transactivator, with Glu/Asp-rich carboxy-terminal domain, 2 | 82071 |
| 202917_s_at | 4.87438447 | S100 calcium binding protein A8 (calgranulin A) | 416073 |
| 207791_s_at | 4.86793585 | RAB1A, member RAS oncogene family | 227327 |
| 222148_s_at | 4.85805606 | ras homolog gene family, member T1 | 14202 |
| 207275_s_at | 4.85293013 | fatty-acid-Coenzyme A ligase, long-chain 2 | 511920 |
| 202803_s_at | 4.84922223 | integrin, beta 2 (antigen CD18 (p95), lymphocyte function-associated antigen 1; macrophage antigen 1 (mac-1) beta subunit) | 375957 |
| 211100_x_at | 4.84737438 | leukocyte immunoglobulin-like receptor, subfamily B (with TM and ITIM domains), member 1 | 149924 |
| 208817_at | 4.84504478 | catechol-O-methyltransferase | 240013 |
| 203767_s_at | 4.83050164 | steroid sulfatase (microsomal), arylsulfatase C, isozyme S | 79876 |
| 212606_at | 4.82536301 | WD repeat and FYVE domain containing 3 | 105340 |
| 205174_s_at | 4.82195934 | glutaminyl-peptide cyclotransferase (glutaminyl cyclase) | 79033 |
| 204714_s_at | 4.81879712 | coagulation factor V (proaccelerin, labile factor) | 30054 |
| 221060_s_at | 4.81814747 | toll-like receptor 4 | 174312 |
| 211999_at | 4.81797645 | H3 histone, family 3B (H3.3B) | 180877 |
| 211102_s_at | 4.81093803 | leukocyte immunoglobulin-like receptor, subfamily B (with TM and ITIM domains), member 1 | 149924 |
| 216243_s_at | 4.80291726 | interleukin 1 receptor antagonist | 81134 |
| 203126_at | 4.79908699 | inositol(myo)-1(or 4)-monophosphatase 2 | 5753 |
| 210785_s_at | 4.79694283 | chromosome 1 open reading frame 38 | 10649 |
| 204232_at | 4.78915713 | Fc fragment of IgE, high affinity I, receptor for; gamma polypeptide | 433300 |
| 200648_s_at | 4.78637919 | glutamate-ammonia ligase (glutamine synthase) | 442669 |
| 218627_at | 4.77005668 | hypothetical protein FLJ11259 | 416393 |
| 209555_s_at | 4.76938604 | CD36 antigen (collagen type I receptor, thrombospondin receptor) | 443120 |
| 206034_at | 4.76674446 | serine (or cysteine) proteinase inhibitor, clade B (ovalbumin), member 8 | 368077 |

TABLE 2-continued

Ischemic stroke related-genes using Benjamini and Yekutieli correction.

| Affy ID No. | t-statistic* | Gene Name | UniGene ID No. |
|---|---|---|---|
| 221581_s_at | 4.75435645 | Williams-Beuren syndrome chromosome region 5 | 56607 |
| 203799_at | 4.73734337 | type I transmembrane C-type lectin receptor DCL-1 | 2441 |
| 203041_s_at | 4.73458725 | lysosomal-associated membrane protein 2 | 232432 |
| 209004_s_at | 4.73446496 | F-box and leucine-rich repeat protein 5 | 5548 |
| 217995_at | 4.72584361 | sulfide quinone reductase-like (yeast) | 435468 |
| 220326_s_at | 4.72372372 | hypothetical protein FLJ10357 | 22451 |
| 207104_x_at | 4.72227406 | leukocyte immunoglobulin-like receptor, subfamily B (with TM and ITIM domains), member 1 | 149924 |
| 217889_s_at | 4.71506397 | cytochrome b reductase 1 | 31297 |
| 215001_s_at | 4.71118486 | glutamate-ammonia ligase (glutamine synthase) | 442669 |
| 207761_s_at | 4.71005806 | DKFZP586A0522 protein | 288771 |
| 205726_at | 4.70850268 | diaphanous homolog 2 (*Drosophila*) | 226483 |
| 208704_x_at | 4.70631847 | amyloid beta (A4) precursor-like protein 2 | 279518 |
| 206674_at | 4.70459455 | fms-related tyrosine kinase 3 | 385 |
| 219582_at | 4.70387413 | hypothetical protein FLJ21079 | 16512 |
| 207872_s_at | 4.70179932 | leukocyte immunoglobulin-like receptor, subfamily B (with TM and ITIM domains), member 1 | 149924 |
| 200782_at | 4.69959007 | annexin A5 | 145741 |
| 201301_s_at | 4.6939926 | annexin A4 | 422986 |
| 202895_s_at | 4.68690449 | protein tyrosine phosphatase, non-receptor type substrate 1 | 156114 |
| 209835_x_at | 4.67551042 | CD44 antigen (homing function and Indian blood group system) | 306278 |
| 201887_at | 4.67403802 | interleukin 13 receptor, alpha 1 | 285115 |
| 205329_s_at | 4.67285443 | sorting nexin 4 | 267812 |
| 205863_at | 4.64921037 | S100 calcium binding protein A12 (calgranulin C) | 19413 |
| 202902_s_at | 4.64873073 | cathepsin S | 181301 |
| 205640_at | 4.64661387 | aldehyde dehydrogenase 3 family, member B1 | 274235 |
| 204900_x_at | 4.64331607 | sin3-associated polypeptide, 30 kDa | 512813 |
| 208908_s_at | 4.63754102 | calpastatin | 440961 |
| 217868_s_at | 4.63345426 | DORA reverse strand protein 1 | 279583 |
| 203360_s_at | 4.62883239 | c-myc binding protein | 78221 |
| 207677_s_at | 4.62647264 | neutrophil cytosolic factor 4, 40 kDa | 196352 |
| 206111_at | 4.60837517 | ribonuclease, RNase A family, 2 (liver, eosinophil-derived neurotoxin) | 728 |
| 210153_s_at | 4.59360403 | malic enzyme 2, NAD(+)-dependent, mitochondrial | 75342 |
| 222231_s_at | 4.58618625 | hypothetical protein PRO1855 | 370927 |
| 201537_s_at | 4.57925877 | dual specificity phosphatase 3 (vaccinia virus phosphatase VH1-related) | 181046 |
| 202201_at | 4.57781605 | biliverdin reductase B (flavin reductase (NADPH)) | 76289 |
| 203591_s_at | 4.5770407 | colony stimulating factor 3 receptor (granulocyte) | 381027 |
| 214366_s_at | 4.5700119 | arachidonate 5-lipoxygenase | 89499 |
| 217977_at | 4.56856597 | selenoprotein X, 1 | 279623 |
| 212527_at | 4.55396497 | DNA segment, Chr 15, Wayne State University 75, expressed | 511996 |
| 211286_x_at | 4.54820757 | colony stimulating factor 2 receptor, alpha, low-affinity (granulocyte-macrophage) | 520937 |
| 222303_at | 4.54612275 | v-ets erythroblastosis virus E26 oncogene homolog 2 (avian) | 292477 |
| 216652_s_at | 4.54389883 | down-regulator of transcription 1, TBP-binding (negative cofactor 2) | 348418 |
| 210660_at | 4.53820668 | leukocyte immunoglobulin-like receptor, subfamily B (with TM and ITIM domains), member 1 | 149924 |
| 202867_s_at | 4.53800788 | DnaJ (Hsp40) homolog, subfamily B, member 12 | 7960 |
| 218559_s_at | 4.53299564 | v-maf musculoaponeurotic fibrosarcoma oncogene homolog B (avian) | 169487 |
| 216950_s_at | 4.53084661 | Fc fragment of IgG, high affinity Ia, receptor for (CD64) | 77424 |
| 213503_x_at | 4.52978946 | annexin A2 | 462864 |
| 214084_x_at | 4.52713467 | *Homo sapiens* similar to neutrophil cytosolic factor 1 (47 kD, chronic granulomatous disease, autosomal 1) (LOC220830), mRNA | 397369 |
| 201298_s_at | 4.52689504 | chromosome 2 open reading frame 6 | 196437 |
| 201940_at | 4.52465759 | carboxypeptidase D | 5057 |
| 220266_s_at | 4.51798181 | Kruppel-like factor 4 (gut) | 376206 |
| 58780_s_at | 4.51518692 | hypothetical protein FLJ10357 | 22451 |
| 211791_s_at | 4.51444942 | potassium voltage-gated channel, shaker-related subfamily, beta member 2 | 440497 |
| 31826_at | 4.51322023 | KIAA0674 protein | 522351 |
| 206643_at | 4.51089381 | histidine ammonia-lyase | 190783 |
| 204227_s_at | 4.50226383 | thymidine kinase 2, mitochondrial | 274701 |
| 201590_x_at | 4.50092732 | annexin A2 | 462864 |
| 207674_at | 4.49675798 | Fc fragment of IgA, receptor for | 193122 |
| 210569_s_at | 4.49584084 | sialic acid binding Ig-like lectin 9 | 245828 |

TABLE 2-continued

Ischemic stroke related-genes using Benjamini and Yekutieli correction.

| Affy ID No. | t-statistic* | Gene Name | UniGene ID No. |
|---|---|---|---|
| 200889_s_at | 4.49074615 | signal sequence receptor, alpha (translocon-associated protein alpha) | 250773 |
| 207697_x_at | 4.48374293 | leukocyte immunoglobulin-like receptor, subfamily B (with TM and ITIM domains), member 2 | 306230 |
| 212117_at | 4.47875698 | ras homolog gene family, member Q | 442989 |
| 213385_at | 4.47853745 | chimerin (chimaerin) 2 | 407520 |
| 212112_s_at | 4.46538788 | syntaxin 12 | 433838 |
| 201943_s_at | 4.46470107 | carboxypeptidase D | 5057 |
| 210235_s_at | 4.45960765 | protein tyrosine phosphatase, receptor type, f polypeptide (PTPRF), interacting protein (liprin), alpha 1 | 128312 |
| 211336_x_at | 4.4529126 | leukocyte immunoglobulin-like receptor, subfamily B (with TM and ITIM domains), member 1 | 149924 |
| 211509_s_at | 4.45275311 | reticulon 4 | 436349 |
| 202349_at | 4.44313773 | dystonia 1, torsion (autosomal dominant; torsin A) | 19261 |
| 212625_at | 4.4411393 | syntaxin 10 | 43812 |
| 211101_x_at | 4.44083795 | leukocyte immunoglobulin-like receptor, subfamily B (with TM and ITIM domains), member 1 | 149924 |
| 217764_s_at | 4.43853195 | RAB31, member RAS oncogene family | 223025 |
| 212602_at | 4.43444968 | WD repeat and FYVE domain containing 3 | 105340 |
| 220088_at | 4.42977252 | complement component 5 receptor 1 (C5a ligand) | 2161 |
| 204445_s_at | 4.42874496 | arachidonate 5-lipoxygenase | 89499 |
| 202593_s_at | 4.4273484 | membrane interacting protein of RGS16 | 512607 |
| 201235_s_at | 4.42419251 | BTG family, member 2 | 75462 |
| 217473_x_at | 4.42406639 | — | — |
| 212271_at | 4.42248213 | mitogen-activated protein kinase 1 | 324473 |
| 204861_s_at | 4.42112414 | baculoviral IAP repeat-containing 1 | 79019 |
| 204502_at | 4.41495415 | SAM domain and HD domain 1 | 371264 |
| 212663_at | 4.41324534 | KIAA0674 protein | 522351 |
| 202295_s_at | 4.40282943 | cathepsin H | 114931 |
| 207571_x_at | 4.40054035 | chromosome 1 open reading frame 38 | 10649 |
| 219974_x_at | 4.39530706 | uncharacterized hypothalamus protein HCDASE | 437091 |
| 201444_s_at | 4.38865234 | ATPase, H+ transporting, lysosomal accessory protein 2 | 183434 |
| 204043_at | 4.38432768 | transcobalamin II; macrocytic anemia | 417948 |
| 201963_at | 4.37921369 | fatty-acid-Coenzyme A ligase, long-chain 2 | 511920 |
| 205071_x_at | 4.37300052 | X-ray repair complementing defective repair in Chinese hamster cells 4 | 150930 |
| 205173_x_at | 4.36642735 | CD58 antigen, (lymphocyte function-associated antigen 3) | 75626 |
| 200615_s_at | 4.36556565 | adaptor-related protein complex 2, beta 1 subunit | 370123 |
| 211419_s_at | 4.36300495 | chimerin (chimaerin) 2 | 407520 |
| 205789_at | 4.36189551 | CD1D antigen, d polypeptide | 1799 |
| 212124_at | 4.35711838 | retinoic acid induced 17 | 438767 |
| 202436_s_at | 4.35300568 | cytochrome P450, family 1, subfamily B, polypeptide 1 | 154654 |
| 203971_at | 4.34868301 | solute carrier family 31 (copper transporters), member 1 | 414471 |
| 219892_at | 4.34634755 | transmembrane 6 superfamily member 1 | 151155 |
| 208594_x_at | 4.34443555 | leukocyte immunoglobulin-like receptor, subfamily B (with TM and ITIM domains), member 3 | 511766 |
| 202877_s_at | 4.33642974 | complement component 1, q subcomponent, receptor 1 | 97199 |
| 214501_s_at | 4.33619357 | H2A histone family, member Y | 75258 |
| 201425_at | 4.33199642 | aldehyde dehydrogenase 2 family (mitochondrial) | 331141 |
| 203066_at | 4.32776894 | B cell RAG associated protein | 523379 |
| 202484_s_at | 4.32503279 | methyl-CpG binding domain protein 2 | 25674 |
| 211296_x_at | 4.31941158 | ubiquitin C | 183704 |
| 213590_at | 4.31821109 | solute carrier family 16 (monocarboxylic acid transporters), member 5 | 90911 |
| 215990_s_at | 4.31739177 | B-cell CLL/lymphoma 6 (zinc finger protein 51) | 155024 |
| 208653_s_at | 4.30983843 | CD164 antigen, sialomucin | 43910 |
| 208734_x_at | 4.30135956 | RAB2, member RAS oncogene family | 78305 |
| 209005_at | 4.29969708 | F-box and leucine-rich repeat protein 5 | 5548 |
| 218739_at | 4.29917434 | abhydrolase domain containing 5 | 19385 |
| 208248_x_at | 4.29909709 | amyloid beta (A4) precursor-like protein 2 | 279518 |
| 208934_s_at | 4.29599303 | lectin, galactoside-binding, soluble, 8 (galectin 8) | 4082 |
| 202820_at | 4.28937583 | aryl hydrocarbon receptor | 170087 |
| 210154_at | 4.28524889 | malic enzyme 2, NAD(+)-dependent, mitochondrial | 75342 |
| 201311_s_at | 4.28104152 | SH3 domain binding glutamic acid-rich protein like | 14368 |
| 210732_s_at | 4.27689192 | lectin, galactoside-binding, soluble, 8 (galectin 8) | 4082 |
| 200942_s_at | 4.27633661 | heat shock factor binding protein 1 | 250899 |
| 201538_s_at | 4.27183553 | dual specificity phosphatase 3 (vaccinia virus phosphatase VH1-related) | 181046 |

TABLE 2-continued

Ischemic stroke related-genes using Benjamini and Yekutieli correction.

| Affy ID No. | t-statistic* | Gene Name | UniGene ID No. |
|---|---|---|---|
| 201179_s_at | 4.27082196 | guanine nucleotide binding protein (G protein), alpha inhibiting activity polypeptide 3 | 73799 |
| 205418_at | 4.2619161 | feline sarcoma oncogene | 7636 |
| 209297_at | 4.25619908 | intersectin 1 (SH3 domain protein) | 66392 |
| 206934_at | 4.25371303 | signal-regulatory protein beta 1 | 194784 |
| 219889_at | 4.24708622 | frequently rearranged in advanced T-cell lymphomas | 126057 |
| 212657_s_at | 4.24239023 | interleukin 1 receptor antagonist | 81134 |
| 209305_s_at | 4.24071078 | growth arrest and DNA-damage-inducible, beta | 110571 |
| 201720_s_at | 4.23720249 | Lysosomal-associated multispanning membrane protein-5 | 436200 |
| 202100_at | 4.23631606 | v-ral simian leukemia viral oncogene homolog B (ras related; GTP binding protein) | 348024 |
| 210422_x_at | 4.23603224 | solute carrier family 11 (proton-coupled divalent metal ion transporters), member 1 | 135163 |
| 203574_at | 4.2315199 | nuclear factor, interleukin 3 regulated | 79334 |
| 209616_s_at | 4.22891755 | carboxylesterase 1 (monocyte/macrophage serine esterase 1) | 278997 |
| 203185_at | 4.2285949 | Ras association (RalGDS/AF-6) domain family 2 | 80905 |
| 212681_at | 4.22845394 | erythrocyte membrane protein band 4.1-like 3 | 103839 |
| 221675_s_at | 4.22714814 | choline phosphotransferase 1 | 225567 |
| 209499_x_at | 4.22636014 | tumor necrosis factor (ligand) superfamily, member 13 | 54673 |
| 204959_at | 4.22614064 | myeloid cell nuclear differentiation antigen | 153837 |
| 204277_s_at | 4.22513355 | thymidine kinase 2, mitochondrial | 274701 |
| 204393_s_at | 4.22305118 | acid phosphatase, prostate | 388677 |
| 216899_s_at | 4.22228511 | src family associated phosphoprotein 2 | 410745 |
| 205627_at | 4.21755984 | cytidine deaminase | 72924 |
| 220001_at | 4.21439779 | peptidyl arginine deiminase, type IV | 397050 |
| 211864_s_at | 4.21257919 | fer-1-like 3, myoferlin (C. elegans) | 362731 |
| 213241_at | 4.21206935 | plexin C1 | 286229 |
| 215708_s_at | 4.21183314 | Homo sapiens transcribed sequence with strong similarity to protein sp: P49643 (H. sapiens) PRI2_HUMAN DNA primase large subunit (DNA primase 58 kDa subunit) (P58) | 356530 |
| 205568_at | 4.2078814 | aquaporin 9 | 104624 |
| 201900_s_at | 4.20012284 | aldo-keto reductase family 1, member A1 (aldehyde reductase) | 372170 |
| 216015_s_at | 4.19778183 | cold autoinflammatory syndrome 1 | 159483 |
| 204908_s_at | 4.19238275 | B-cell CLL/lymphoma 3 | 31210 |
| 206420_at | 4.19184626 | immunoglobulin superfamily, member 6 | 135194 |
| 206359_at | 4.18559959 | suppressor of cytokine signaling 3 | 436943 |
| 216905_s_at | 4.18538303 | suppression of tumorigenicity 14 (colon carcinoma, matriptase, epithin) | 56937 |
| 218439_s_at | 4.18516434 | PTD002 protein | 151458 |
| 211816_x_at | 4.18499309 | Fc fragment of IgA, receptor for | 193122 |
| 204336_s_at | 4.18093971 | regulator of G-protein signalling 19 | 422336 |
| 201647_s_at | 4.17905107 | scavenger receptor class B, member 2 | 323567 |
| 219872_at | 4.17884427 | hypothetical protein DKFZp434L142 | 323583 |
| 211527_x_at | 4.17650619 | vascular endothelial growth factor | 73793 |
| 211749_s_at | 4.17531793 | vesicle-associated membrane protein 3 (cellubrevin) | 66708 |
| 219666_at | 4.17515543 | membrane-spanning 4-domains, subfamily A, member 6A | 371612 |
| 221858_at | 4.17028941 | KIAA0608 protein | 100960 |
| 208351_s_at | 4.16464496 | mitogen-activated protein kinase 1 | 324473 |
| 218035_s_at | 4.1625156 | RNA-binding protein | 95549 |
| 209276_s_at | 4.16115658 | glutaredoxin (thioltransferase) | 28988 |
| 202497_x_at | 4.16041756 | solute carrier family 2 (facilitated glucose transporter), member 3 | 419240 |
| 213988_s_at | 4.15957906 | spermidine/spermine N1-acetyltransferase | 28491 |
| 202381_at | 4.14084013 | a disintegrin and metalloproteinase domain 9 (meltrin gamma) | 2442 |
| 205936_s_at | 4.13559524 | hexokinase 3 (white cell) | 411695 |
| 209287_s_at | 4.13557674 | CDC42 effector protein (Rho GTPase binding) 3 | 352554 |
| 221194_s_at | 4.13485757 | PTD016 protein | 30154 |
| 210648_x_at | 4.13480197 | sorting nexin 3 | 12102 |
| 205237_at | 4.1324867 | ficolin (collagen/fibrinogen domain containing) 1 | 440898 |
| 204899_s_at | 4.12933139 | sin3-associated polypeptide, 30 kDa | 512813 |
| 207085_x_at | 4.12207721 | colony stimulating factor 2 receptor, alpha, low-affinity (granulocyte-macrophage) | 520937 |
| 207266_x_at | 4.12058364 | RNA binding motif, single stranded interacting protein 1 | 241567 |
| 221492_s_at | 4.12038439 | autophagy Apg3p/Aut1p-like | 26367 |
| 207387_s_at | 4.11738071 | glycerol kinase | 1466 |

TABLE 2-continued

Ischemic stroke related-genes using Benjamini and Yekutieli correction.

| Affy ID No. | t-statistic* | Gene Name | UniGene ID No. |
|---|---|---|---|
| 204122_at | 4.11663505 | TYRO protein tyrosine kinase binding protein | 9963 |
| 207671_s_at | 4.11610597 | vitelliform macular dystrophy (Best disease, bestrophin) | 167344 |
| 207857_at | 4.10927392 | leukocyte immunoglobulin-like receptor, subfamily B (with TM and ITIM domains), member 1 | 149924 |
| 201850_at | 4.10860435 | capping protein (actin filament), gelsolin-like | 82422 |
| 202934_at | 4.10351746 | hexokinase 2 | 406266 |
| 206335_at | 4.10242677 | galactosamine (N-acetyl)-6-sulfate sulfatase (Morquio syndrome, mucopolysaccharidosis type IVA) | 159479 |
| 221078_s_at | 4.09863405 | hypothetical protein FLJ10392 | 292925 |
| 201337_s_at | 4.09676745 | vesicle-associated membrane protein 3 (cellubrevin) | 66708 |
| 203005_at | 4.0932063 | lymphotoxin beta receptor (TNFR superfamily, member 3) | 1116 |
| 203676_at | 4.09251365 | glucosamine (N-acetyl)-6-sulfatase (Sanfilippo disease IIID) | 334534 |
| 205401_at | 4.09190279 | alkylglycerone phosphate synthase | 407933 |
| 218865_at | 4.08907346 | hypothetical protein FLJ22390 | 195345 |
| 201473_at | 4.08893087 | jun B proto-oncogene | 400124 |
| 220000_at | 4.08612321 | sialic acid binding Ig-like lectin 5 | 117005 |
| 208983_s_at | 4.0855044 | platelet/endothelial cell adhesion molecule (CD31 antigen) | 78146 |
| 218424_s_at | 4.08296857 | dudulin 2 | 57655 |
| 201186_at | 4.08234245 | low density lipoprotein receptor-related protein associated protein 1 | 75140 |
| 210959_s_at | 4.08090496 | steroid-5-alpha-reductase, alpha polypeptide 1 (3-oxo-5 alpha-steroid delta 4-dehydrogenase alpha 1) | 552 |
| 213160_at | 4.07719887 | dedicator of cyto-kinesis 2 | 17211 |
| 201463_s_at | 4.07608806 | transaldolase 1 | 438678 |
| 200078_s_at | 4.07300443 | ATPase, H+ transporting, lysosomal 21 kDa, V0 subunit c" | 7476 |
| 201506_at | 4.07150831 | transforming growth factor, beta-induced, 68 kDa | 421496 |
| 217826_s_at | 4.07137819 | ubiquitin-conjugating enzyme E2, J1 (UBC6 homolog, yeast) | 184325 |
| 38487_at | 4.06946114 | stabilin 1 | 301989 |
| 217827_s_at | 4.06896229 | acid cluster protein 33 | 242458 |
| 201642_at | 4.06630731 | interferon gamma receptor 2 (interferon gamma transducer 1) | 409200 |
| 211997_x_at | 4.06180968 | H3 histone, family 3B (H3.3B) | 180877 |
| 211540_s_at | 4.06076677 | retinoblastoma 1 (including osteosarcoma) | 408528 |
| 221036_s_at | 4.05925589 | anterior pharynx defective 1B-like | 42954 |
| 208097_s_at | 4.049855 | thioredoxin domain containing | 125221 |
| 201828_x_at | 4.04673957 | CAAX box 1 | 250708 |
| 217853_at | 4.04364724 | tensin-like SH2 domain-containing 1 | 12210 |
| 207270_x_at | 4.04254236 | CMRF35 leukocyte immunoglobulin-like receptor | 2605 |
| 217159_x_at | 4.04053417 | sialic acid binding Ig-like lectin 7 | 274470 |
| 209901_x_at | 4.03786304 | allograft inflammatory factor 1 | 76364 |
| 216236_s_at | 4.03358432 | solute carrier family 2 (facilitated glucose transporter), member 14 | 401274 |
| 204961_s_at | 4.03301863 | neutrophil cytosolic factor 1 (47 kDa, chronic granulomatous disease, autosomal 1) | 458275 |
| 202101_s_at | 4.03192448 | v-ral simian leukemia viral oncogene homolog B (ras related; GTP binding protein) | 348024 |
| 208189_s_at | 4.03164659 | myosin VIIA (Usher syndrome 1B (autosomal recessive, severe)) | 370421 |
| 201554_x_at | 4.03078928 | glycogenin | 174071 |
| 219505_at | 4.03062109 | cat eye syndrome chromosome region, candidate 1 | 170310 |
| 202445_s_at | 4.02993448 | Notch homolog 2 (Drosophila) | 8121 |
| 208071_s_at | 4.02784691 | leukocyte-associated Ig-like receptor 1 | 407964 |
| 220832_at | 4.02284364 | toll-like receptor 8 | 272410 |
| 212419_at | 4.02284151 | hypothetical protein FLJ90798 | 28264 |
| 203857_s_at | 4.02278318 | for protein disulfide isomerase-related | 76901 |
| 202122_s_at | 4.02240203 | cargo selection protein (mannose 6 phosphate receptor binding protein) | 140452 |
| 208936_x_at | 4.02052401 | lectin, galactoside-binding, soluble, 8 (galectin 8) | 4082 |
| 219806_s_at | 4.01642219 | FN5 protein | 416456 |
| 205922_at | 4.01615381 | vanin 2 | 293130 |
| 209311_at | 4.01610957 | BCL2-like 2 | 410026 |
| 210340_s_at | 4.01506832 | colony stimulating factor 2 receptor, alpha, low-affinity (granulocyte-macrophage) | 520937 |
| 216346_at | 4.01350716 | SEC14-like 3 (S. cerevisiae) | 434140 |
| 202944_at | 4.00826135 | N-acetylgalactosaminidase, alpha- | 75372 |
| 206877_at | 4.00750632 | MAX dimerization protein 1 | 379930 |
| 209473_at | 4.00302974 | ectonucleoside triphosphate diphosphohydrolase 1 | 444105 |

TABLE 2-continued

Ischemic stroke related-genes using Benjamini and Yekutieli correction.

| Affy ID No. | t-statistic* | Gene Name | UniGene ID No. |
|---|---|---|---|
| 208785_s_at | 3.99946577 | Homo sapiens transcribed sequence with strong similarity to protein ref: NP_073729.1 (H. sapiens) microtubule-associated proteins 1A/1B light chain 3 [Homo sapiens] | 419777 |
| 202108_at | 3.99887308 | peptidase D | 444207 |
| 201926_s_at | 3.99380381 | decay accelerating factor for complement (CD55, Cromer blood group system) | 408864 |
| 201413_at | 3.990689 | hydroxysteroid (17-beta) dehydrogenase 4 | 356894 |
| 210190_at | 3.99016278 | syntaxin 11 | 118958 |
| 215842_s_at | 3.98910601 | ATPase, Class VI, type 11A | 29189 |
| 204361_s_at | 3.98317434 | src family associated phosphoprotein 2 | 410745 |
| 202826_at | 3.97921395 | serine protease inhibitor, Kunitz type 1 | 233950 |
| 200798_x_at | 3.97812485 | myeloid cell leukemia sequence 1 (BCL2-related) | 86386 |
| 203471_s_at | 3.97445343 | pleckstrin | 77436 |
| 213532_at | 3.97420929 | hypothetical protein LOC285148 | 509314 |
| 206710_s_at | 3.97151204 | erythrocyte membrane protein band 4.1-like 3 | 103839 |
| 221879_at | 3.97046064 | ceroid-lipofuscinosis, neuronal 6, late infantile, variant | 43654 |
| 204446_s_at | 3.97025459 | arachidonate 5-lipoxygenase | 89499 |
| 200677_at | 3.96789671 | pituitary tumor-transforming 1 interacting protein | 369026 |
| 201118_at | 3.96505944 | phosphogluconate dehydrogenase | 392837 |
| 205868_s_at | 3.96375543 | protein tyrosine phosphatase, non-receptor type 11 (Noonan syndrome 1) | 83572 |
| 212252_at | 3.96319972 | calcium/calmodulin-dependent protein kinase kinase 2, beta | 297343 |
| 203887_s_at | 3.96298525 | thrombomodulin | 2030 |
| 202192_s_at | 3.96240466 | growth arrest-specific 7 | 226133 |
| 201096_s_at | 3.95648407 | ADP-ribosylation factor 4 | 435639 |
| 219911_s_at | 3.94841313 | solute carrier family 21 (organic anion transporter), member 12 | 235782 |
| 200796_s_at | 3.94807209 | myeloid cell leukemia sequence 1 (BCL2-related) | 86386 |
| 219890_at | 3.94731168 | C-type (calcium dependent, carbohydrate-recognition domain) lectin, superfamily member 5 | 126355 |
| 208724_s_at | 3.94528806 | RAB1A, member RAS oncogene family | 227327 |
| 212374_at | 3.94463692 | fem-1 homolog b (C. elegans) | 362733 |
| 219104_at | 3.94384785 | ring finger protein 141 | 44685 |
| 203748_x_at | 3.94217815 | RNA binding motif, single stranded interacting protein 1 | 241567 |
| 210773_s_at | 3.94043935 | formyl peptide receptor-like 1 | 99855 |
| 219607_s_at | 3.93984379 | membrane-spanning 4-domains, subfamily A, member 4 | 325960 |
| 206348_s_at | 3.9380531 | pyruvate dehydrogenase kinase, isoenzyme 3 | 193124 |
| 215856_at | 3.93781449 | hypothetical protein LOC284266 | 287692 |
| 200737_at | 3.93283779 | phosphoglycerate kinase 1 | 78771 |
| 218831_s_at | 3.93205147 | Fc fragment of IgG, receptor, transporter, alpha | 111903 |
| 202437_s_at | 3.92627151 | cytochrome P450, family 1, subfamily B, polypeptide 1 | 154654 |
| 201942_s_at | 3.92566977 | carboxypeptidase D | 5057 |
| 219859_at | 3.92247489 | C-type (calcium dependent, carbohydrate-recognition domain) lectin, superfamily member 9 | 236516 |
| 212054_x_at | 3.91644887 | KIAA0676 protein | 155829 |
| 208540_x_at | 3.91561327 | — | 506947 |
| 213119_at | 3.91488544 | solute carrier family 36 (proton/amino acid symporter), member 1 | 409314 |
| 205119_s_at | 3.91440214 | formyl peptide receptor 1 | 753 |
| 201576_s_at | 3.91382693 | galactosidase, beta 1 | 445183 |
| 212014_x_at | 3.9085234 | CD44 antigen (homing function and Indian blood group system) | 306278 |
| 210156_s_at | 3.90785487 | protein-L-isoaspartate (D-aspartate) O-methyltransferase | 79137 |
| 205540_s_at | 3.90407281 | Ras-related GTP binding B | 50282 |
| 212598_at | 3.90198488 | WD repeat and FYVE domain containing 3 | 105340 |
| 221724_s_at | 3.89891636 | C-type (calcium dependent, carbohydrate-recognition domain) lectin, superfamily member 6 | 115515 |
| 208952_s_at | 3.89761036 | KIAA0217 protein | 192881 |
| 200738_s_at | 3.89752042 | phosphoglycerate kinase 1 | 78771 |
| 206380_s_at | 3.89281079 | properdin P factor, complement | 53155 |
| 211287_x_at | 3.89139509 | colony stimulating factor 2 receptor, alpha, low-affinity (granulocyte-macrophage) | 520937 |
| 210953_at | 3.89109344 | KIAA0669 gene product | 52526 |
| 201798_s_at | 3.88996697 | fer-1-like 3, myoferlin (C. elegans) | 362731 |
| 208885_at | 3.88981825 | lymphocyte cytosolic protein 1 (L-plastin) | 381099 |
| 202671_s_at | 3.88812247 | pyridoxal (pyridoxine, vitamin B6) kinase | 284491 |
| 202433_at | 3.88667317 | solute carrier family 35, member B1 | 154073 |

TABLE 2-continued

Ischemic stroke related-genes using Benjamini and Yekutieli correction.

| Affy ID No. | t-statistic* | Gene Name | UniGene ID No. |
|---|---|---|---|
| 220775_s_at | 3.88608806 | ubiquitin-conjugating enzyme E2-like | 407991 |
| 202030_at | 3.88474448 | branched chain alpha-ketoacid dehydrogenase kinase | 20644 |
| 205639_at | 3.88308443 | acyloxyacyl hydrolase (neutrophil) | 82542 |
| 202096_s_at | 3.88275079 | benzodiazapine receptor (peripheral) | 202 |
| 202241_at | 3.87918071 | phosphoprotein regulated by mitogenic pathways | 444947 |
| 200958_s_at | 3.8722837 | syndecan binding protein (syntenin) | 164067 |
| 211689_s_at | 3.87053754 | transmembrane protease, serine 2 | 439309 |
| 207157_s_at | 3.86989748 | guanine nucleotide binding protein (G protein), gamma 5 | 436765 |
| 210186_s_at | 3.86911308 | FK506 binding protein 1A, 12 kDa | 374638 |
| 200987_x_at | 3.86682174 | proteasome (prosome, macropain) activator subunit 3 (PA28 gamma; Ki) | 152978 |
| 208853_s_at | 3.8665582 | calnexin | 155560 |
| 212026_s_at | 3.86220136 | likely ortholog of mouse exocyst component protein 70 kDa homolog (*S. cerevisiae*) Exo70: exocyst component protein 70 kDa homolog (*S. cerevisiae*) | 511946 |
| 201898_s_at | 3.861804 | ubiquitin-conjugating enzyme E2A (RAD6 homolog) | 379466 |
| 209615_s_at | 3.85852692 | p21/Cdc42/Rac1-activated kinase 1 (STE20 homolog, yeast) | 64056 |
| 208488_s_at | 3.85497758 | complement component (3b/4b) receptor 1, including Knops blood group system | 334019 |
| 203853_s_at | 3.85414745 | GRB2-associated binding protein 2 | 30687 |
| 209131_s_at | 3.85261742 | synaptosomal-associated protein, 23 kDa | 202308 |
| 204150_at | 3.85178342 | stabilin 1 | 301989 |
| 212188_at | 3.85075667 | hypothetical protein BC013764 | 109438 |
| 211087_x_at | 3.85069595 | mitogen-activated protein kinase 14 | 79107 |
| 205920_at | 3.8477849 | solute carrier family 6 (neurotransmitter transporter, taurine), member 6 | 1194 |
| 219079_at | 3.84686335 | NADPH cytochrome B5 oxidoreductase | 5741 |
| 201619_at | 3.84148866 | peroxiredoxin 3 | 397062 |
| 214438_at | 3.84078431 | H2.0-like homeo box 1 (*Drosophila*) | 74870 |
| 211507_s_at | 3.83656731 | myotubularin related protein 3 | 412833 |
| 217835_x_at | 3.83446552 | chromosome 20 open reading frame 24 | 184062 |
| 217825_s_at | 3.82162344 | ubiquitin-conjugating enzyme E2, J1 (UBC6 homolog, yeast) | 184325 |
| 205681_at | 3.81769723 | BCL2-related protein A1 | 227817 |
| 200827_at | 3.81766405 | procollagen-lysine, 2-oxoglutarate 5-dioxygenase (lysine hydroxylase, Ehlers-Danlos syndrome type VI) | 75093 |
| 211797_s_at | 3.8151505 | nuclear transcription factor Y, gamma | 285133 |
| 204194_at | 3.81135547 | BTB and CNC homology 1, basic leucine zipper transcription factor 1 | 154276 |
| 201078_at | 3.81097664 | transmembrane 9 superfamily member 2 | 298272 |
| 206343_s_at | 3.81055509 | neuregulin 1 | 172816 |
| 218091_at | 3.80590961 | HIV-1 Rev binding protein | 352962 |
| 205468_s_at | 3.80336547 | interferon regulatory factor 5 | 334450 |
| 200929_at | 3.79657368 | transmembrane trafficking protein | 74137 |
| 206881_s_at | 3.79242916 | leukocyte immunoglobulin-like receptor, subfamily A (without TM domain), member 3 | 113277 |
| 209404_s_at | 3.79062874 | CGI-109 protein | 278391 |
| 207549_x_at | 3.79036164 | membrane cofactor protein (CD46, trophoblast-lymphocyte cross-reactive antigen) | 83532 |
| 219646_at | 3.78787522 | hypothetical protein FLJ20186 | 62771 |
| 219991_at | 3.78398642 | solute carrier family 2 (facilitated glucose transporter), member 9 | 95497 |
| 211922_s_at | 3.78374234 | catalase | 395771 |
| 210275_s_at | 3.78115446 | zinc finger protein 216 | 406096 |
| 216883_x_at | 3.77914282 | phosphodiesterase 6D, cGMP-specific, rod, delta | 48291 |
| 202833_s_at | 3.77713205 | serine (or cysteine) proteinase inhibitor, clade A (alpha-1 antiproteinase, antitrypsin), member 1 | 297681 |
| 217124_at | 3.77620277 | KIAA1023 protein | 446063 |
| 209062_x_at | 3.77508965 | nuclear receptor coactivator 3 | 382168 |
| 208310_s_at | 3.77468002 | follistatin-like 1 | 433622 |
| 212041_at | 3.77461664 | ATPase, H+ transporting, lysosomal 38 kDa, V0 subunit d isoform 1 | 106876 |
| 214500_at | 3.77290459 | H2A histone family, member Y | 75258 |
| 217746_s_at | 3.77075614 | programmed cell death 6 interacting protein | 9663 |
| 218754_at | −3.7702453 | hypothetical protein FLJ23323 | 59425 |
| 214749_s_at | −3.7716173 | hypothetical protein FLJ20811 | 83530 |
| 203094_at | −3.7722118 | MAD2L1 binding protein | 122346 |
| 221230_s_at | −3.7758096 | retinoblastoma binding protein 1-like 1 | 17428 |
| 212912_at | −3.7760375 | ribosomal protein S6 kinase, 90 kDa, polypeptide 2 | 301664 |

TABLE 2-continued

Ischemic stroke related-genes using Benjamini and Yekutieli correction.

| Affy ID No. | t-statistic* | Gene Name | UniGene ID No. |
|---|---|---|---|
| 205004_at | −3.7765763 | NF-kappa B-repressing factor | 437084 |
| 205775_at | −3.7769304 | DNA segment on chromosome 6(unique) 2654 expressed sequence | 140944 |
| 219007_at | −3.7819237 | nucleoporin 43 kDa | 53263 |
| 206082_at | −3.7826255 | HLA complex P5 | 511759 |
| 214022_s_at | −3.7838188 | interferon induced transmembrane protein 1 (9-27) | 458414 |
| 210243_s_at | −3.7882423 | UDP-Gal: betaGlcNAc beta 1,4-galactosyltransferase, polypeptide 3 | 321231 |
| 204228_at | −3.7929943 | peptidyl prolyl isomerase H (cyclophilin H) | 9880 |
| 204411_at | −3.793944 | KIAA0449 protein | 511940 |
| 213388_at | −3.7946632 | Homo sapiens mRNA; cDNA DKFZp586I1823 (from clone DKFZp586I1823) | 448231 |
| 205963_s_at | −3.7953901 | DnaJ (Hsp40) homolog, subfamily A, member 3 | 6216 |
| 221535_at | −3.8112387 | hypothetical protein FLJ11301 | 436471 |
| 209302_at | −3.811649 | polymerase (RNA) II (DNA directed) polypeptide H | 432574 |
| 221867_at | −3.8131693 | hypothetical protein FLJ31821 | 511839 |
| 213028_at | −3.8138531 | Homo sapiens cDNA FLJ44314 fis, clone TRACH2025932 | 419777 |
| 209870_s_at | −3.8147819 | amyloid beta (A4) precursor protein-binding, family A, member 2 (X11-like) | 26468 |
| 210847_x_at | −3.8164631 | tumor necrosis factor receptor superfamily, member 25 | 299558 |
| 218955_at | −3.8194881 | BRF2, subunit of RNA polymerase III transcription initiation factor, BRF1-like | 274136 |
| 64418_at | −3.8220874 | AP1 gamma subunit binding protein 1 | 404215 |
| 36888_at | −3.8320679 | KIAA0841 protein | 7426 |
| 219971_at | −3.8331453 | interleukin 21 receptor | 210546 |
| 221963_x_at | −3.836647 | Homo sapiens transcribed sequence with strong similarity to protein pir: TSHUP1 (H. sapiens) TSHUP1 thrombospondin 1 precursor - human | — |
| 200045_at | −3.8367612 | ATP-binding cassette, sub-family F (GCN20), member 1 | 9573 |
| 221135_s_at | −3.8379739 | HT001 protein | 254124 |
| 221940_at | −3.8380758 | C18B11 homolog (44.9 kD) | 173311 |
| 203386_at | −3.8411936 | TBC1 domain family, member 4 | 173802 |
| 212660_at | −3.8431641 | PHD finger protein 15 | 397990 |
| 206240_s_at | −3.8440853 | zinc finger protein 136 (clone pHZ-20) | 479874 |
| 204461_x_at | −3.8452 | RAD1 homolog (S. pombe) | 7179 |
| 49329_at | −3.8471735 | hypothetical protein FLJ14360 | 351563 |
| 201763_s_at | −3.8485837 | death-associated protein 6 | 336916 |
| 218601_at | −3.8507869 | up-regulated gene 4 | 5131 |
| 216309_x_at | −3.8522271 | jerky homolog (mouse) | 142296 |
| 213742_at | −3.8525732 | splicing factor, arginine/serine-rich 11 | 443458 |
| 205255_x_at | −3.8532902 | transcription factor 7 (T-cell specific, HMG-box) | 169294 |
| 219123_at | −3.8535773 | zinc finger protein 232 | 279914 |
| 39248_at | −3.8602222 | aquaporin 3 | 234642 |
| 214351_x_at | −3.8603602 | ribosomal protein L13 | 410817 |
| 213360_s_at | −3.8667261 | similar to Nuclear envelope pore membrane protein POM 121 (Pore membrane protein of 121 kDa) (P145) | 450237 |
| 210031_at | −3.8668203 | CD3Z antigen, zeta polypeptide (TiT3 complex) | 97087 |
| 204484_at | −3.8676808 | phosphoinositide-3-kinase, class 2, beta polypeptide | 343329 |
| 217798_at | −3.8703856 | CCR4-NOT transcription complex, subunit 2 | 165725 |
| 200957_s_at | −3.8715464 | structure specific recognition protein 1 | 79162 |
| 206188_at | −3.8905582 | KIAA0628 gene product | 43133 |
| 221518_s_at | −3.8970401 | ubiquitin specific protease 47 | 441028 |
| 221978_at | −3.8977136 | major histocompatibility complex, class I, F | 411958 |
| 218500_at | −3.9056647 | mesenchymal stem cell protein DSCD75 | 25237 |
| 219765_at | −3.9104452 | hypothetical protein FLJ12586 | 458377 |
| 207339_s_at | −3.9120005 | lymphotoxin beta (TNF superfamily, member 3) | 376208 |
| 218496_at | −3.9220606 | ribonuclease H1 | 511960 |
| 204891_s_at | −3.9250376 | lymphocyte-specific protein tyrosine kinase | 1765 |
| 203611_at | −3.9251415 | telomeric repeat binding factor 2 | 63335 |
| 213689_x_at | −3.9253484 | ribosomal protein L5 | 469653 |
| 38398_at | −3.9258197 | MAP-kinase activating death domain | 82548 |
| 46256_at | −3.9261723 | SPRY domain-containing SOCS box protein SSB-3 | 7247 |
| 214692_s_at | −3.9264268 | jerky homolog (mouse) | 142296 |
| 40446_at | −3.9318725 | PHD finger protein 1 | 166204 |
| 217802_s_at | −3.9322297 | nuclear ubiquitous casein kinase and cyclin-dependent kinase substrate | 510265 |
| 218573_at | −3.9379843 | APR-1 protein | 279819 |
| 221277_s_at | −3.9418985 | hypothetical protein FKSG32 | 98682 |
| 204182_s_at | −3.9459862 | zinc finger protein 297B | 355581 |
| 212653_s_at | −3.94854 | KIAA0903 protein | 16218 |

TABLE 2-continued

Ischemic stroke related-genes using Benjamini and Yekutieli correction.

| Affy ID No. | t-statistic* | Gene Name | UniGene ID No. |
|---|---|---|---|
| 201717_at | −3.9504943 | mitochondrial ribosomal protein L49 | 75859 |
| 218700_s_at | −3.9516027 | RAB7, member RAS oncogene family-like 1 | 115325 |
| 217950_at | −3.9535594 | nitric oxide synthase interacting protein | 7236 |
| 208758_at | −3.9548631 | 5-aminoimidazole-4-carboxamide ribonucleotide formyltransferase/IMP cyclohydrolase | 90280 |
| 202617_s_at | −3.9570199 | methyl CpG binding protein 2 (Rett syndrome) | 3239 |
| 212935_at | −3.9602659 | MCF.2 cell line derived transforming sequence-like | 436905 |
| 222077_s_at | −3.9734422 | Rac GTPase activating protein 1 | 23900 |
| 221087_s_at | −3.9735482 | apolipoprotein L, 3 | 241535 |
| 202330_s_at | −3.9749735 | uracil-DNA glycosylase | 78853 |
| 206545_at | −3.9833463 | CD28 antigen (Tp44) | 1987 |
| 218414_s_at | −3.9863793 | nudE nuclear distribution gene E homolog 1 (A. nidulans) | 263925 |
| 209440_at | −3.9905647 | phosphoribosyl pyrophosphate synthetase 1 | 56 |
| 219966_x_at | −3.9987967 | BTG3 associated nuclear protein | 448828 |
| 215359_x_at | −4.0024233 | zinc finger protein 44 (KOX 7) | 501604 |
| 215012_at | −4.0067262 | zinc finger protein 451 | 188662 |
| 205192_at | −4.0075631 | mitogen-activated protein kinase kinase kinase 14 | 440315 |
| 206118_at | −4.0108593 | signal transducer and activator of transcription 4 | 80642 |
| 213574_s_at | −4.011904 | karyopherin (importin) beta 1 | 439683 |
| 200644_at | −4.015547 | MARCKS-like protein | 75061 |
| 218274_s_at | −4.0156737 | hypothetical protein FLJ10415 | 437647 |
| 212037_at | −4.0191262 | pinin, desmosome associated protein | 409965 |
| 203723_at | −4.0201929 | inositol 1,4,5-trisphosphate 3-kinase B | 78877 |
| 202970_at | −4.03346 | dual-specificity tyrosine-(Y)-phosphorylation regulated kinase 2 | 173135 |
| 219169_s_at | −4.0376252 | transcription factor B1, mitochondrial | 279908 |
| 202562_s_at | −4.0376994 | chromosome 14 open reading frame 1 | 15106 |
| 213648_at | −4.0401386 | KIAA0116 protein | 254717 |
| 205442_at | −4.0500447 | KIAA0626 gene product | 178121 |
| 219658_at | −4.0522935 | hypothetical protein FLJ12598 | 126906 |
| 217627_at | −4.0526775 | hypothetical protein FLJ30921 | 290703 |
| 202968_s_at | −4.0534127 | dual-specificity tyrosine-(Y)-phosphorylation regulated kinase 2 | 173135 |
| 204008_at | −4.0615836 | dynein, axonemal, light polypeptide 4 | 258203 |
| 203450_at | −4.065337 | chromosome 22 open reading frame 2 | 334911 |
| 219812_at | −4.0673436 | stromal antigen 3 | 323634 |
| 219109_at | −4.0689872 | PF20 | 6783 |
| 213473_at | −4.0764661 | ankyrin repeat domain 13 | 122764 |
| 40016_g_at | −4.0768183 | KIAA0303 protein | 212787 |
| 203556_at | −4.079399 | transcription factor ZHX2 | 30209 |
| 209798_at | −4.0837583 | nuclear protein, ataxia-telangiectasia locus | 89385 |
| 219635_at | −4.0865204 | hypothetical protein FLJ14260 | 287629 |
| 212589_at | −4.0884147 | related RAS viral (r-ras) oncogene homolog 2 | 206097 |
| 204327_s_at | −4.0891305 | zinc finger protein 202 | 112556 |
| 216262_s_at | −4.0902501 | TGFB-induced factor 2 (TALE family homeobox) | 94785 |
| 222348_at | −4.0911661 | KIAA0303 protein | 212787 |
| 220035_at | −4.101629 | nucleoporin 210 | 292119 |
| 213039_at | −4.1044199 | Rho-specific guanine nucleotide exchange factor p114 | 6150 |
| 208858_s_at | −4.1054066 | likely ortholog of mouse membrane bound C2 domain containing protein | 8309 |
| 218805_at | −4.1065589 | immune associated nucleotide 4 like 1 (mouse) | 412331 |
| 209558_s_at | −4.108666 | huntingtin interacting protein-1-related | 96731 |
| 207394_at | −4.1102265 | zinc finger protein 137 (clone pHZ-30) | 373648 |
| 220418_at | −4.1185695 | ubiquitin associated and SH3 domain containing, A | 183924 |
| 219155_at | −4.1208338 | phosphatidylinositol transfer protein, cytoplasmic 1 | 405933 |
| 222266_at | −4.121441 | chromosome 19 open reading frame 2 | 7943 |
| 214739_at | −4.1236762 | hypothetical protein MGC4126 | 334483 |
| 219006_at | −4.1353669 | chromosome 6 open reading frame 66 | 512144 |
| 209657_s_at | −4.14338 | heat shock transcription factor 2 | 158195 |
| 64064_at | −4.1445869 | immune associated nucleotide 4 like 1 (mouse) | 412331 |
| 205964_at | −4.147438 | zinc finger protein 426 | 324978 |
| 204635_at | −4.1496187 | ribosomal protein S6 kinase, 90 kDa, polypeptide 5 | 109058 |
| 212320_at | −4.151357 | beta 5-tubulin | 356729 |
| 208094_s_at | −4.1580744 | hypothetical protein MGC10471 | 24998 |
| 48117_at | −4.1689003 | hypothetical protein BC011981 | 110407 |
| 218492_s_at | −4.1719389 | THAP domain containing 7 | 512756 |
| 219045_at | −4.1781811 | ras homolog gene family, member F (in filopodia) | 512618 |
| 217152_at | −4.1800035 | nuclear receptor co-repressor 1 | 144904 |
| 203159_at | −4.1901598 | glutaminase | 128410 |
| 219700_at | −4.1962225 | plexin domain containing 1 | 125036 |
| 213958_at | −4.2016236 | CD6 antigen | 436949 |
| 210763_x_at | −4.2056306 | natural cytotoxicity triggering receptor 3 | 509513 |
| 209586_s_at | −4.2061369 | TcD37 homolog | 78524 |

TABLE 2-continued

Ischemic stroke related-genes using Benjamini and Yekutieli correction.

| Affy ID No. | t-statistic* | Gene Name | UniGene ID No. |
|---|---|---|---|
| 202931_x_at | −4.2107515 | bridging integrator 1 | 193163 |
| 202741_at | −4.2145218 | protein kinase, cAMP-dependent, catalytic, beta | 156324 |
| 218259_at | −4.2150435 | myocardin-related transcription factor B | 151076 |
| 202724_s_at | −4.2194658 | forkhead box O1A (rhabdomyosarcoma) | 170133 |
| 217912_at | −4.2238457 | PP3111 protein | 351484 |
| 220969_s_at | −4.2271761 | — | — |
| 220367_s_at | −4.2316067 | mSin3A-associated protein 130 | 133523 |
| 219315_s_at | −4.2333807 | hypothetical protein FLJ20898 | 25549 |
| 218510_x_at | −4.237976 | hypothetical protein FLJ20152 | 82273 |
| 216983_s_at | −4.2380619 | zinc finger protein 224 | 279855 |
| 218735_s_at | −4.2447866 | zinc finger protein | 438994 |
| 213179_at | −4.2560283 | RCD1 required for cell differentiation1 homolog (*S. pombe*) | 148767 |
| 204020_at | −4.2566815 | purine-rich element binding protein A | 29117 |
| 204630_s_at | −4.2576483 | golgi SNAP receptor complex member 1 | 124436 |
| 201853_s_at | −4.2599718 | cell division cycle 25B | 153752 |
| 214771_x_at | −4.2674176 | Rho interacting protein 3 | 430725 |
| 213539_at | −4.281273 | CD3D antigen, delta polypeptide (TiT3 complex) | 95327 |
| 202693_s_at | −4.2866716 | serine/threonine kinase 17a (apoptosis-inducing) | 9075 |
| 200953_s_at | −4.2970373 | cyclin D2 | 376071 |
| 205590_at | −4.3097591 | RAS guanyl releasing protein 1 (calcium and DAG-regulated) | 189527 |
| 213193_x_at | −4.3143922 | Homo sapiens T cell receptor beta chain BV20S1 BJ1-5 BC1 mRNA, complete cds | 487862 |
| 210915_x_at | −4.342139 | Homo sapiens T cell receptor beta chain BV20S1 BJ1-5 BC1 mRNA, complete cds | 349283 |
| 220176_at | −4.3595778 | chromosome 14 open reading frame 127 | 288981 |
| 38340_at | −4.3617132 | huntingtin interacting protein-1-related | 96731 |
| 209246_at | −4.3621957 | ATP-binding cassette, sub-family F (GCN20), member 2 | 438823 |
| 204633_s_at | −4.3717038 | ribosomal protein S6 kinase, 90 kDa, polypeptide 5 | 109058 |
| 202250_s_at | −4.3738264 | H326 | 120904 |
| 210538_s_at | −4.3739708 | baculoviral IAP repeat-containing 3 | 127799 |
| 219350_s_at | −4.3780164 | second mitochondria-derived activator of caspase | 169611 |
| 209014_at | −4.3855467 | melanoma antigen, family D, 1 | 5258 |
| 204642_at | −4.4025727 | endothelial differentiation, sphingolipid G-protein-coupled receptor, 1 | 154210 |
| 207892_at | −4.4032046 | tumor necrosis factor (ligand) superfamily, member 5 (hyper-IgM syndrome) | 652 |
| 217957_at | −4.4033051 | likely ortholog of mouse gene trap locus 3 | 279818 |
| 212333_at | −4.4079871 | DKFZP564F0522 protein | 23060 |
| 202178_at | −4.4303479 | protein kinase C, zeta | 407181 |
| 210279_at | −4.431287 | G protein-coupled receptor 18 | 88269 |
| 202726_at | −4.4373616 | ligase I, DNA, ATP-dependent | 1770 |
| 214298_x_at | −4.4417332 | septin 6 | |
| 207426_s_at | −4.4487533 | tumor necrosis factor (ligand) superfamily, member 4 (tax-transcriptionally activated glycoprotein 1, 34 kDa) | 181097 |
| 212126_at | −4.4504669 | Homo sapiens, clone IMAGE: 5288883, mRNA | 149466 |
| 206150_at | −4.4509904 | tumor necrosis factor receptor superfamily, member 7 | 355307 |
| 209282_at | −4.4662679 | protein kinase D2 | 205431 |
| 212313_at | −4.4669031 | hypothetical protein MGC29816 | 5019 |
| 205379_at | −4.4687636 | carbonyl reductase 3 | 154510 |
| 217961_at | −4.4688902 | hypothetical protein FLJ20551 | 7994 |
| 219843_at | −4.4747042 | intracisternal A particle-promoted polypeptide | 157180 |
| 219826_at | −4.4750415 | hypothetical protein FLJ23233 | 98593 |
| 209682_at | −4.4805853 | Cas-Br-M (murine) ecotropic retroviral transforming sequence b | 436986 |
| 221790_s_at | −4.4853949 | LDL receptor adaptor protein | 184482 |
| 203408_s_at | −4.4896587 | special AT-rich sequence binding protein 1 (binds to nuclear matrix/scaffold-associating DNA's) | 416026 |
| 210389_x_at | −4.4925237 | likely ortholog of mouse tubulin, delta 1 | 270847 |
| 221601_s_at | −4.5045431 | regulator of Fas-induced apoptosis | 58831 |
| 202478_at | −4.5256195 | tribbles homolog 2 | 155418 |
| 214439_x_at | −4.5286267 | bridging integrator 1 | 193163 |
| 36545_s_at | −4.5486784 | KIAA0542 gene product | 62209 |
| 211596_s_at | −4.571525 | leucine-rich repeats and immunoglobulin-like domains 1 | 166697 |
| 213587_s_at | −4.5921811 | chromosome 7 open reading frame 32 | 351612 |
| 203717_at | −4.6064222 | dipeptidylpeptidase 4 (CD26, adenosine deaminase complexing protein 2) | 44926 |
| 203648_at | −4.6075718 | KIAA0218 gene product | 75863 |
| 218723_s_at | −4.6189582 | RGC32 protein | 76640 |
| 201528_at | −4.6259618 | replication protein A1, 70 kDa | 84318 |

TABLE 2-continued

Ischemic stroke related-genes using Benjamini and Yekutieli correction.

| Affy ID No. | t-statistic* | Gene Name | UniGene ID No.^ |
|---|---|---|---|
| 202107_s_at | −4.6331766 | MCM2 minichromosome maintenance deficient 2, mitotin (*S. cerevisiae*) | 57101 |
| 32259_at | −4.665109 | enhancer of zeste homolog 1 (*Drosophila*) | 194669 |
| 221211_s_at | −4.6673208 | chromosome 21 open reading frame 7 | 41267 |
| 201313_at | −4.6724774 | enolase 2, (gamma, neuronal) | 511915 |
| 221234_s_at | −4.6843954 | BTB and CNC homology 1, basic leucine zipper transcription factor 2 | 88414 |
| 46665_at | −4.6856302 | sema domain, immunoglobulin domain (Ig), transmembrane domain (TM) and short cytoplasmic domain, (semaphorin) 4C | 7188 |
| 219590_x_at | −4.6895774 | CGI-30 protein | 406051 |
| 203965_at | −4.6942774 | ubiquitin specific protease 20 | 5452 |
| 205042_at | −4.7104355 | UDP-N-acetylglucosamine-2-epimerase/N-acetylmannosamine kinase | 5920 |
| 205233_s_at | −4.7127287 | platelet-activating factor acetylhydrolase 2, 40 kDa | 477083 |
| 209881_s_at | −4.723093 | linker for activation of T cells | 498997 |
| 210201_x_at | −4.7310315 | bridging integrator 1 | 193163 |
| 208795_s_at | −4.7315545 | MCM7 minichromosome maintenance deficient 7 (*S. cerevisiae*) | 438720 |
| 206829_x_at | −4.7446912 | zinc finger protein 430 | 309348 |
| 215785_s_at | −4.7595567 | cytoplasmic FMR1 interacting protein 2 | 211201 |
| 206337_at | −4.7716012 | chemokine (C—C motif) receptor 7 | 1652 |
| 214177_s_at | −4.7755992 | pre-B-cell leukemia transcription factor interacting protein 1 | 505806 |
| 204828_at | −4.7856359 | RAD9 homolog A (*S. pombe*) | 240457 |
| 205013_s_at | −4.8029535 | adenosine A2a receptor | 197029 |
| 203564_at | −4.8064489 | Fanconi anemia, complementation group G | 434873 |
| 202481_at | −4.811268 | short-chain dehydrogenase/reductase 1 | 17144 |
| 205310_at | −4.8291386 | hypothetical protein 20D7-FC4 | 128702 |
| 215235_at | −4.830164 | spectrin, alpha, non-erythrocytic 1 (alpha-fodrin) | 387905 |
| 203956_at | −4.8519414 | KIAA0852 protein | 143840 |
| 214833_at | −4.8566377 | KIAA0792 gene product | 119387 |
| 204957_at | −4.8590232 | origin recognition complex, subunit 5-like (yeast) | 153138 |
| 212414_s_at | −4.8647531 | septin 6 | 90998 |
| 213164_at | −4.8698375 | mitochondrial ribosomal protein S6 | 268016 |
| 211005_at | −4.9017443 | linker for activation of T cells | 498997 |
| 209670_at | −4.9218273 | T cell receptor alpha locus | 74647 |
| 57082_at | −4.9228846 | LDL receptor adaptor protein | 184482 |
| 203846_at | −4.9250454 | tripartite motif-containing 32 | 236218 |
| 200965_s_at | −5.0317556 | actin binding LIM protein 1 | 442540 |
| 214808_at | −5.0730906 | Homo sapiens cDNA FLJ11958 fis, clone HEMBB1000996. | 519791 |
| 35147_at | −5.0896447 | MCF.2 cell line derived transforming sequence-like | 436905 |
| 206039_at | −5.1020197 | RAB33A, member RAS oncogene family | 56294 |
| 201677_at | −5.1309712 | DC12 protein | 458320 |
| 221011_s_at | −5.1441771 | likely ortholog of mouse limb-bud and heart gene | 57209 |
| 203062_s_at | −5.1456619 | mediator of DNA damage checkpoint 1 | 433653 |
| 207231_at | −5.167881 | zinc finger DAZ interacting protein 3 | 409210 |
| 207734_at | −5.2935692 | hypothetical protein FLJ20340 | 272794 |
| 202423_at | −5.3252148 | MYST histone acetyltransferase (monocytic leukemia) 3 | 93231 |
| 201930_at | −5.3290801 | MCM6 minichromosome maintenance deficient 6 (MIS5 homolog, *S. pombe*) (*S. cerevisiae*) | 444118 |
| 213620_s_at | −5.4358397 | intercellular adhesion molecule 2 | 433303 |
| 38269_at | −5.5792458 | protein kinase D2 | 205431 |
| 209603_at | −5.9506916 | GATA binding protein 3 | 169946 |
| 219798_s_at | −5.9710113 | hypothetical protein FLJ20257 | 178011 |
| 210038_at | −6.1736133 | protein kinase C, theta | 408049 |

*Positive t-statistic indicates that the gene is upregulated following an ischemic stroke. Negative t-statistic indicates that the gene is downregulated following an ischemic stroke.

^UniGene ID number is system for automatically partitioning GenBank sequences into a non-redundant set of gene-oriented clusters. Each UniGene cluster contains sequences that represent a unique gene, as well as related information such as the tissue types in which the gene has been expressed and map location. UniGene numbers can be searched on the NCBI website.

Following Bonferroni correction, 231 gene probes, corresponding to 190 genes, were found to be significant (Table 3). Clear separation of the stroke and control gene expression levels were observed. As shown in Table 3, several genes were upregulated (positive T-statistic, such as a value that is at least 4.73) or downregulated (negative t-statistic, such as a value that is less than −4.73) following an ischemic stroke.

TABLE 3

Ischemic stroke related-genes using Bonferroni correction.

| Affy ID No. | t-statistic* | Gene Name | UniGene ID No. |
|---|---|---|---|
| 218454_at | 7.8939046 | hypothetical protein FLJ22662 | 178470 |
| 215049_x_at | 7.8695991 | CD163 antigen | 74076 |
| 203645_s_at | 7.7927429 | CD163 antigen | 74076 |
| 211404_s_at | 7.6192982 | amyloid beta (A4) precursor-like protein 2 | 279518 |
| 206120_at | 7.6130371 | CD33 antigen (gp67) | 83731 |
| 208771_s_at | 7.4480951 | leukotriene A4 hydrolase | 81118 |
| 210872_x_at | 7.2957674 | growth arrest-specific 7 | 226133 |
| 201328_at | 7.196077 | v-ets erythroblastosis virus E26 oncogene homolog 2 (avian) | 292477 |
| 222173_s_at | 7.0181137 | TBC1 domain family, member 2 | 371016 |
| 211612_s_at | 6.7100761 | interleukin 13 receptor, alpha 1 | 285115 |
| 211067_s_at | 6.6632809 | growth arrest-specific 7 | 226133 |
| 211368_s_at | 6.6564605 | caspase 1, apoptosis-related cysteine protease (interleukin 1, beta, convertase) | 2490 |
| 219788_at | 6.6357632 | paired immunoglobin-like type 2 receptor alpha | 122591 |
| 202896_s_at | 6.6343375 | protein tyrosine phosphatase, non-receptor type substrate 1 | 156114 |
| 221210_s_at | 6.6307936 | N-acetylneuraminate pyruvate lyase (dihydrodipicolinate synthase) | 64896 |
| 204924_at | 6.6002629 | toll-like receptor 2 | 439608 |
| 206488_s_at | 6.5474747 | CD36 antigen (collagen type I receptor, thrombospondin receptor) | 443120 |
| 208146_s_at | 6.5359521 | carboxypeptidase, vitellogenic-like | 95594 |
| 213006_at | 6.5058834 | KIAA0146 protein | 381058 |
| 208923_at | 6.4690445 | cytoplasmic FMR1 interacting protein 1 | 26704 |
| 208702_x_at | 6.4619855 | amyloid beta (A4) precursor-like protein 2 | 279518 |
| 204452_s_at | 6.452735 | frizzled homolog 1 (Drosophila) | 94234 |
| 205715_at | 6.4316015 | bone marrow stromal cell antigen 1 | 169998 |
| 216942_s_at | 6.4235387 | CD58 antigen, (lymphocyte function-associated antigen 3) | 75626 |
| 218217_at | 6.419306 | likely homolog of rat and mouse retinoid-inducible serine carboxypeptidase | 431107 |
| 212192_at | 6.4140293 | hypothetical protein BC013764 | 109438 |
| 200868_s_at | 6.3921161 | zinc finger protein 313 | 144949 |
| 202912_at | 6.3889633 | adrenomedullin | 441047 |
| 207691_x_at | 6.3716999 | ectonucleoside triphosphate diphosphohydrolase 1 | 444105 |
| 209124_at | 6.322399 | myeloid differentiation primary response gene (88) | 82116 |
| 204620_s_at | 6.3107101 | chondroitin sulfate proteoglycan 2 (versican) | 434488 |
| 203535_at | 6.2998102 | S100 calcium binding protein A9 (calgranulin B) | 112405 |
| 202878_s_at | 6.2900118 | complement component 1, q subcomponent, receptor 1 | 97199 |
| 204249_s_at | 6.2863054 | LIM domain only 2 (rhombotin-like 1) | 283063 |
| 208872_s_at | 6.2665313 | polyposis locus protein 1 | 173119 |
| 205603_s_at | 6.2533791 | diaphanous homolog 2 (Drosophila) | 226483 |
| 208818_s_at | 6.2031095 | catechol-O-methyltransferase | 240013 |
| 205158_at | 6.2009402 | ribonuclease, RNase A family, 4 | 283749 |
| 200765_x_at | 6.1928897 | catenin (cadherin-associated protein), alpha 1, 102 kDa | 254321 |
| 220615_s_at | 6.1326079 | hypothetical protein FLJ10462 | 134497 |
| 202897_at | 6.1313157 | protein tyrosine phosphatase, non-receptor type substrate 1 | 156114 |
| 204222_s_at | 6.1245309 | GLI pathogenesis-related 1 (glioma) | 511765 |
| 201743_at | 6.1155498 | CD14 antigen | 75627 |
| 211744_s_at | 6.0521758 | CD58 antigen, (lymphocyte function-associated antigen 3) | 75626 |
| 207168_s_at | 6.0419796 | H2A histone family, member Y | 75258 |
| 220034_at | 6.0415584 | interleukin-1 receptor-associated kinase 3 | 268552 |
| 204099_at | 6.0275171 | SWI/SNF related, matrix associated, actin dependent regulator of chromatin, subfamily d, member 3 | 444445 |
| 212335_at | 6.0167789 | glucosamine (N-acetyl)-6-sulfatase (Sanfilippo disease IIID) | 334534 |
| 211135_x_at | 6.0123178 | leukocyte immunoglobulin-like receptor, subfamily B (with TM and ITIM domains), member 3 | 511766 |
| 203127_s_at | 5.9862871 | serine palmitoyltransferase, long chain base subunit 2 | 59403 |
| 201041_s_at | 5.9752594 | dual specificity phosphatase 1 | 171695 |
| 209949_at | 5.9749633 | neutrophil cytosolic factor 2 (65 kDa, chronic granulomatous disease, autosomal 2) | 949 |
| 203922_s_at | 5.9579176 | cytochrome b-245, beta polypeptide (chronic granulomatous disease) | 88974 |
| 200838_at | 5.9562695 | cathepsin B | 135226 |
| 210844_x_at | 5.9341934 | catenin (cadherin-associated protein), alpha 1, 102 kDa | 254321 |
| 200886_s_at | 5.905732 | phosphoglycerate mutase 1 (brain) | 447492 |

TABLE 3-continued

Ischemic stroke related-genes using Bonferroni correction.

| Affy ID No. | t-statistic* | Gene Name | UniGene ID No. |
|---|---|---|---|
| 208949_s_at | 5.8880039 | lectin, galactoside-binding, soluble, 3 (galectin 3) | 411701 |
| 211284_s_at | 5.8723751 | granulin | 180577 |
| 210992_x_at | 5.7814222 | Fc fragment of IgG, low affinity IIa, receptor for (CD32) | 352642 |
| 204860_s_at | 5.7675599 | *Homo sapiens* transcribed sequence with strong similarity to protein sp: Q13075 (*H. sapiens*) BIR1_HUMAN Baculoviral LAP repeat-containing protein 1 (Neuronal apoptosis inhibitory protein) | 508565 |
| 212788_x_at | 5.7508112 | ferritin, light polypeptide | 433670 |
| 211776_s_at | 5.7448982 | erythrocyte membrane protein band 4.1-like 3 | 103839 |
| 221731_x_at | 5.7407504 | chondroitin sulfate proteoglycan 2 (versican) | 434488 |
| 210225_x_at | 5.7405956 | leukocyte immunoglobulin-like receptor, subfamily B (with TM and ITIM domains), member 3 | 511766 |
| 218404_at | 5.7312675 | sorting nexin 10 | 418132 |
| 214511_x_at | 5.7139856 | Fc fragment of IgG, high affinity Ia, receptor for (CD64) | 77424 |
| 200764_s_at | 5.6724223 | catenin (cadherin-associated protein), alpha 1, 102 kDa | 254321 |
| 210904_s_at | 5.6679489 | interleukin 13 receptor, alpha 1 | 285115 |
| 201200_at | 5.6494608 | cellular repressor of E1A-stimulated genes | 5710 |
| 209189_at | 5.6491225 | v-fos FBJ murine osteosarcoma viral oncogene homolog | 25647 |
| 202943_s_at | 5.6217726 | N-acetylgalactosaminidase, alpha- | 75372 |
| 201329_s_at | 5.6098071 | v-ets erythroblastosis virus E26 oncogene homolog 2 (avian) | 292477 |
| 200678_x_at | 5.5920695 | granulin | 180577 |
| 200839_s_at | 5.5911028 | cathepsin B | 135226 |
| 204053_x_at | 5.5889098 | phosphatase and tensin homolog (mutated in multiple advanced cancers 1) | 253309 |
| 204759_at | 5.5751089 | chromosome condensation 1-like | 27007 |
| 217897_at | 5.5697271 | FXYD domain containing ion transport regulator 6 | 410748 |
| 203973_s_at | 5.5691171 | KIAA0146 protein | 381058 |
| 210951_x_at | 5.5484656 | RAB27A, member RAS oncogene family | 298530 |
| 216041_x_at | 5.5475628 | granulin | 180577 |
| 208454_s_at | 5.5419198 | plasma glutamate carboxypeptidase | 197335 |
| 209970_x_at | 5.5292079 | caspase 1, apoptosis-related cysteine protease (interleukin 1, beta, convertase) | 2490 |
| 204646_at | 5.5021786 | dihydropyrimidine dehydrogenase | 1602 |
| 202990_at | 5.4976619 | phosphorylase, glycogen; liver (Hers disease, glycogen storage disease type VI) | 282417 |
| 218606_at | 5.4924926 | zinc finger, DHHC domain containing 7 | 9725 |
| 219316_s_at | 5.47794 | chromosome 14 open reading frame 58 | 267566 |
| 207574_s_at | 5.4709451 | growth arrest and DNA-damage-inducible, beta | 110571 |
| 212807_s_at | 5.462952 | sortilin 1 | 394609 |
| 214875_x_at | 5.4629191 | amyloid beta (A4) precursor-like protein 2 | 279518 |
| 202446_s_at | 5.4579541 | phospholipid scramblase 1 | 348478 |
| 210784_x_at | 5.416225 | leukocyte immunoglobulin-like receptor, subfamily B (with TM and ITIM domains), member 3 | 511766 |
| 203561_at | 5.4154987 | Fc fragment of IgG, low affinity IIa, receptor for (CD32) | 352642 |
| 210152_at | 5.408888 | leukocyte immunoglobulin-like receptor, subfamily B (with TM and ITIM domains), member 4 | 67846 |
| 210427_x_at | 5.374221 | annexin A2 | 462864 |
| 212830_at | 5.3739539 | EGF-like-domain, multiple 5 | 236216 |
| 204169_at | 5.3658872 | IMP (inosine monophosphate) dehydrogenase 1 | 317095 |
| 209500_x_at | 5.3457527 | tumor necrosis factor (ligand) superfamily, member 13 | 54673 |
| 201432_at | 5.3369374 | catalase | 395771 |
| 215646_s_at | 5.3337393 | chondroitin sulfate proteoglycan 2 (versican) | 434488 |
| 201422_at | 5.3321762 | interferon, gamma-inducible protein 30 | 14623 |
| 204112_s_at | 5.330181 | histamine N-methyltransferase | 42151 |
| 214318_s_at | 5.3243137 | hypothetical protein CG003 | 390874 |
| 204588_s_at | 5.3231924 | solute carrier family 7 (cationic amino acid transporter, y+ system), member 7 | 194693 |
| 211366_x_at | 5.3228655 | caspase 1, apoptosis-related cysteine protease (interleukin 1, beta, convertase) | 2490 |
| 217865_at | 5.2774855 | ring finger protein 130 | 155718 |
| 211133_x_at | 5.2667742 | leukocyte immunoglobulin-like receptor, subfamily B (with TM and ITIM domains), member 3 | 511766 |
| 209091_s_at | 5.2660794 | SH3-domain GRB2-like endophilin B1 | 136309 |
| 209474_s_at | 5.2656896 | ectonucleoside triphosphate diphosphohydrolase 1 | 444105 |
| 209514_s_at | 5.2571756 | RAB27A, member RAS oncogene family | 298530 |
| 211571_s_at | 5.254094 | chondroitin sulfate proteoglycan 2 (versican) | 434488 |
| 201426_s_at | 5.2533276 | vimentin | 435800 |

TABLE 3-continued

Ischemic stroke related-genes using Bonferroni correction.

| Affy ID No. | t-statistic* | Gene Name | UniGene ID No. |
|---|---|---|---|
| 209069_s_at | 5.2359413 | H3 histone, family 3B (H3.3B) | 180877 |
| 208130_s_at | 5.2328997 | thromboxane A synthase 1 (platelet, cytochrome P450, family 5, subfamily A) | 444510 |
| 220990_s_at | 5.2293055 | likely ortholog of rat vacuole membrane protein 1 | 166254 |
| 210314_x_at | 5.2226225 | tumor necrosis factor (ligand) superfamily, member 13 | 54673 |
| 203140_at | 5.2122493 | B-cell CLL/lymphoma 6 (zinc finger protein 51) | 155024 |
| 205147_x_at | 5.2045679 | neutrophil cytosolic factor 4, 40 kDa | 196352 |
| 210101_x_at | 5.1985794 | SH3-domain GRB2-like endophilin B1 | 136309 |
| 205896_at | 5.1985084 | solute carrier family 22 (organic cation transporter), member 4 | 441130 |
| 206130_s_at | 5.197136 | asialoglycoprotein receptor 2 | 1259 |
| 211367_s_at | 5.1824911 | caspase 1, apoptosis-related cysteine protease (interleukin 1, beta, convertase) | 2490 |
| 217521_at | 5.1760536 | histidine ammonia-lyase | 190783 |
| 212501_at | 5.1661262 | CCAAT/enhancer binding protein (C/EBP), beta | 99029 |
| 218013_x_at | 5.1602528 | dynactin 4 (p62) | 328865 |
| 209188_x_at | 5.1523164 | down-regulator of transcription 1, TBP-binding (negative cofactor 2) | 348418 |
| 202670_at | 5.1509752 | mitogen-activated protein kinase kinase 1 | 132311 |
| 217492_s_at | 5.1487987 | phosphatase and tensin homolog (mutated in multiple advanced cancers 1), pseudogene 1 | 493716 |
| 206600_s_at | 5.1452293 | solute carrier family 16 (monocarboxylic acid transporters), member 5 | 90911 |
| 208959_s_at | 5.1384925 | thioredoxin domain containing 4 (endoplasmic reticulum) | 154023 |
| 209073_s_at | 5.1251219 | numb homolog (*Drosophila*) | 445301 |
| 206237_s_at | 5.118236 | neuregulin 1 | 172816 |
| 209185_s_at | 5.116767 | insulin receptor substrate 2 | 143648 |
| 211702_s_at | 5.0981002 | ubiquitin specific protease 32 | 436133 |
| 200742_s_at | 5.0925572 | ceroid-lipofuscinosis, neuronal 2, late infantile (Jansky-Bielschowsky disease) | 429658 |
| 214449_s_at | 5.0883926 | ras homolog gene family, member Q | 442989 |
| 204834_at | 5.0700936 | fibrinogen-like 2 | 351808 |
| 204619_s_at | 5.0677445 | chondroitin sulfate proteoglycan 2 (versican) | 434488 |
| 208926_at | 5.0624784 | sialidase 1 (lysosomal sialidase) | 118721 |
| 201944_at | 5.0610548 | hexosaminidase B (beta polypeptide) | 69293 |
| 202727_s_at | 5.0520316 | interferon gamma receptor 1 | 180866 |
| 211676_s_at | 5.0386297 | interferon gamma receptor 1 | 180866 |
| 204493_at | 5.0317822 | BH3 interacting domain death agonist | 300825 |
| 219015_s_at | 5.0301077 | uncharacterized hematopoietic stem/progenitor cells protein MDS031 | 110853 |
| 209397_at | 5.0300249 | malic enzyme 2, NAD(+)-dependent, mitochondrial | 75342 |
| 217741_s_at | 5.0253595 | zinc finger protein 216 | 406096 |
| 201044_x_at | 5.0162483 | dual specificity phosphatase 1 | 171695 |
| 219694_at | 5.013375 | hypothetical protein FLJ11127 | 155085 |
| 201127_s_at | 5.0064345 | ATP citrate lyase | 387567 |
| 209304_x_at | 5.001544 | growth arrest and DNA-damage-inducible, beta | 110571 |
| 211395_x_at | 4.9985031 | Fc fragment of IgG, low affinity IIb, receptor for (CD32) | 126384 |
| 205786_s_at | 4.9968981 | integrin, alpha M (complement component receptor 3, alpha; also known as CD11b (p170), macrophage antigen alpha polypeptide) | 172631 |
| 212268_at | 4.9939523 | serine (or cysteine) proteinase inhibitor, clade B (ovalbumin), member 1 | 381167 |
| 202787_s_at | 4.9906145 | mitogen-activated protein kinase-activated protein kinase 3 | 234521 |
| 203888_at | 4.9896332 | thrombomodulin | 2030 |
| 221841_s_at | 4.9829736 | Kruppel-like factor 4 (gut) | 376206 |
| 201888_s_at | 4.9773809 | interleukin 13 receptor, alpha 1 | 285115 |
| 200785_s_at | 4.9557896 | low density lipoprotein-related protein 1 (alpha-2-macroglobulin receptor) | 162757 |
| 203167_at | 4.9520306 | tissue inhibitor of metalloproteinase 2 | 6441 |
| 201193_at | 4.9498323 | isocitrate dehydrogenase 1 (NADP+), soluble | 11223 |
| 208018_s_at | 4.9436874 | hemopoietic cell kinase | 89555 |
| 216202_s_at | 4.9129508 | serine palmitoyltransferase, long chain base subunit 2 | 59403 |
| 212820_at | 4.910653 | rabconnectin-3 | 200828 |
| 218092_s_at | 4.9105339 | HIV-1 Rev binding protein | 352962 |
| 207654_x_at | 4.8995961 | down-regulator of transcription 1, TBP-binding (negative cofactor 2) | 348418 |
| 203746_s_at | 4.8929704 | holocytochrome c synthase (cytochrome c heme-lyase) | 211571 |
| 207704_s_at | 4.8927493 | growth arrest-specific 7 | 226133 |
| 222218_s_at | 4.8926469 | paired immunoglobin-like type 2 receptor alpha | 122591 |

TABLE 3-continued

Ischemic stroke related-genes using Bonferroni correction.

| Affy ID No. | t-statistic* | Gene Name | UniGene ID No. |
|---|---|---|---|
| 207980_s_at | 4.8812625 | Cbp/p300-interacting transactivator, with Glu/Asprich carboxy-terminal domain, 2 | 82071 |
| 202917_s_at | 4.8743845 | S100 calcium binding protein A8 (calgranulin A) | 416073 |
| 207791_s_at | 4.8679359 | RAB1A, member RAS oncogene family | 227327 |
| 222148_s_at | 4.8580561 | ras homolog gene family, member T1 | 14202 |
| 207275_s_at | 4.8529301 | fatty-acid-Coenzyme A ligase, long-chain 2 | 511920 |
| 202803_s_at | 4.8492222 | integrin, beta 2 (antigen CD18 (p95), lymphocyte function-associated antigen 1; macrophage antigen 1 (mac-1) beta subunit) | 375957 |
| 211100_x_at | 4.8473744 | leukocyte immunoglobulin-like receptor, subfamily B (with TM and ITIM domains), member 1 | 149924 |
| 208817_at | 4.8450448 | catechol-O-methyltransferase | 240013 |
| 203767_s_at | 4.8305016 | steroid sulfatase (microsomal), arylsulfatase C, isozyme S | 79876 |
| 212606_at | 4.825363 | WD repeat and FYVE domain containing 3 | 105340 |
| 205174_s_at | 4.8219593 | glutaminyl-peptide cyclotransferase (glutaminyl cyclase) | 79033 |
| 204714_s_at | 4.8187971 | coagulation factor V (proaccelerin, labile factor) | 30054 |
| 221060_s_at | 4.8181475 | toll-like receptor 4 | 174312 |
| 211999_at | 4.8179764 | H3 histone, family 3B (H3.3B) | 180877 |
| 211102_s_at | 4.810938 | leukocyte immunoglobulin-like receptor, subfamily B (with TM and ITIM domains), member 1 | 149924 |
| 216243_s_at | 4.8029173 | interleukin 1 receptor antagonist | 81134 |
| 203126_at | 4.799087 | inositol(myo)-1(or 4)-monophosphatase 2 | 5753 |
| 210785_s_at | 4.7969428 | chromosome 1 open reading frame 38 | 10649 |
| 204232_at | 4.7891571 | Fc fragment of IgE, high affinity I, receptor for; gamma polypeptide | 433300 |
| 200648_s_at | 4.7863792 | glutamate-ammonia ligase (glutamine synthase) | 442669 |
| 218627_at | 4.7700567 | hypothetical protein FLJ11259 | 416393 |
| 209555_s_at | 4.769386 | CD36 antigen (collagen type I receptor, thrombospondin receptor) | 443120 |
| 206034_at | 4.7667445 | serine (or cysteine) proteinase inhibitor, clade B (ovalbumin), member 8 | 368077 |
| 221581_s_at | 4.7543565 | Williams-Beuren syndrome chromosome region 5 | 56607 |
| 203799_at | 4.7373434 | type I transmembrane C-type lectin receptor DCL-1 | 2441 |
| 203041_s_at | 4.7345873 | lysosomal-associated membrane protein 2 | 232432 |
| 209004_s_at | 4.734465 | F-box and leucine-rich repeat protein 5 | 5548 |
| 210201_x_at | -4.731032 | bridging integrator 1 | 193163 |
| 208795_s_at | -4.731554 | MCM7 minichromosome maintenance deficient 7 (S. cerevisiae) | 438720 |
| 206829_x_at | -4.744691 | zinc finger protein 430 | 309348 |
| 215785_s_at | -4.759557 | cytoplasmic FMR1 interacting protein 2 | 211201 |
| 206337_at | -4.771601 | chemokine (C—C motif) receptor 7 | 1652 |
| 214177_s_at | -4.775599 | pre-B-cell leukemia transcription factor interacting protein 1 | 505806 |
| 204828_at | -4.785636 | RAD9 homolog A (S. pombe) | 240457 |
| 205013_s_at | -4.802954 | adenosine A2a receptor | 197029 |
| 203564_at | -4.806449 | Fanconi anemia, complementation group G | 434873 |
| 202481_at | -4.811268 | short-chain dehydrogenase/reductase 1 | 17144 |
| 205310_at | -4.829139 | hypothetical protein 20D7-FC4 | 128702 |
| 215235_at | -4.830164 | spectrin, alpha, non-erythrocytic 1 (alpha-fodrin) | 387905 |
| 203956_at | -4.851941 | KIAA0852 protein | 143840 |
| 214833_at | -4.856638 | KIAA0792 gene product | 119387 |
| 204957_at | -4.859023 | origin recognition complex, subunit 5-like (yeast) | 153138 |
| 212414_s_at | -4.864753 | septin 6 | 90998 |
| 213164_at | -4.869838 | mitochondrial ribosomal protein S6 | 268016 |
| 211005_at | -4.901744 | linker for activation of T cells | 498997 |
| 209670_at | -4.921827 | T cell receptor alpha locus | 74647 |
| 57082_at | -4.922885 | LDL receptor adaptor protein | 184482 |
| 203846_at | -4.925045 | tripartite motif-containing 32 | 236218 |
| 200965_s_at | -5.031756 | actin binding LIM protein 1 | 442540 |
| 214808_at | -5.073091 | Homo sapiens cDNA FLJ11958 fis, clone HEMBB1000996. | 397369 |
| 35147_at | -5.089645 | MCF.2 cell line derived transforming sequence-like | 436905 |
| 206039_at | -5.10202 | RAB33A, member RAS oncogene family | 56294 |
| 201677_at | -5.130971 | DC12 protein | 458320 |
| 221011_s_at | -5.144177 | likely ortholog of mouse limb-bud and heart gene | 57209 |
| 203062_s_at | -5.145662 | mediator of DNA damage checkpoint 1 | 433653 |
| 207231_at | -5.167881 | zinc finger DAZ interacting protein 3 | 409210 |
| 207734_at | -5.293569 | hypothetical protein FLJ20340 | 272794 |
| 202423_at | -5.325215 | MYST histone acetyltransferase (monocytic leukemia) 3 | 93231 |
| 201930_at | -5.32908 | MCM6 minichromosome maintenance deficient 6 (MIS5 homolog, S. pombe) (S. cerevisiae) | 444118 |

TABLE 3-continued

Ischemic stroke related-genes using Bonferroni correction.

| Affy ID No. | t-statistic* | Gene Name | UniGene ID No.^ |
|---|---|---|---|
| 213620_s_at | −5.43584 | intercellular adhesion molecule 2 | 433303 |
| 38269_at | −5.579246 | protein kinase D2 | 205431 |
| 209603_at | −5.950692 | GATA binding protein 3 | 169946 |
| 219798_s_at | −5.971011 | hypothetical protein FLJ20257 | 178011 |
| 210038_at | −6.173613 | protein kinase C, theta | 408049 |

*Positive t-statistic indicates that the gene is upregulated following an ischemic stroke. Negative t-statistic indicates that the gene is downregulated following an ischemic stroke.
^UniGene ID number is system for automatically partitioning GenBank sequences into a non-redundant set of gene-oriented clusters. Each UniGene cluster contains sequences that represent a unique gene, as well as related information such as the tissue types in which the gene has been expressed and map location. UniGene numbers can be searched on the NCBI website.

After multiple comparison correction (MCC) using the Westfall and Young permutation approach, 91 gene probes, corresponding to 82 genes were found to be significantly different (Table 4). As shown in Table 4, several genes were upregulated (positive T-statistic, such as a value that is at least 5.3) or downregulated (negative t-statistic, such as a value that is less than −5.4) following an ischemic stroke.

TABLE 4

Ischemic stroke related-genes using Westfall and Young correction.

| Affy ID # | t-statistic* | Gene Name | UniGene ID No.^ |
|---|---|---|---|
| 218454_at | 7.893904631 | hypothetical protein FLJ22662 | 178470 |
| 215049_x_at | 7.869599129 | CD163 antigen | 74076 |
| 203645_s_at | 7.792742866 | CD163 antigen | 74076 |
| 211404_s_at | 7.61929825 | amyloid beta (A4) precursor-like protein 2 | 279518 |
| 206120_at | 7.613037145 | CD33 antigen (gp67) | 83731 |
| 208771_s_at | 7.448095101 | leukotriene A4 hydrolase | 81118 |
| 210872_x_at | 7.295767389 | growth arrest-specific 7 | 226133 |
| 201328_at | 7.196076979 | v-ets erythroblastosis virus E26 oncogene homolog 2 (avian) | 292477 |
| 222173_s_at | 7.01811369 | TBC1 domain family, member 2 | 371016 |
| 211612_s_at | 6.710076137 | interleukin 13 receptor, alpha 1 | 285115 |
| 211067_s_at | 6.663280893 | growth arrest-specific 7 | 226133 |
| 211368_s_at | 6.656460461 | caspase 1, apoptosis-related cysteine protease (interleukin 1, beta, convertase) | 2490 |
| 219788_at | 6.635763202 | paired immunoglobin-like type 2 receptor alpha | 122591 |
| 202896_s_at | 6.634337453 | protein tyrosine phosphatase, non-receptor type substrate 1 | 156114 |
| 221210_s_at | 6.630793631 | N-acetylneuraminate pyruvate lyase (dihydrodipicolinate synthase) | 64896 |
| 204924_at | 6.60026287 | toll-like receptor 2 | 439608 |
| 206488_s_at | 6.547474681 | CD36 antigen (collagen type I receptor, thrombospondin receptor) | 443120 |
| 208146_s_at | 6.535952056 | carboxypeptidase, vitellogenic-like | 95594 |
| 213006_at | 6.505883417 | KIAA0146 protein | 381058 |
| 208923_at | 6.469044495 | cytoplasmic FMR1 interacting protein 1 | 26704 |
| 208702_x_at | 6.461985493 | amyloid beta (A4) precursor-like protein 2 | 279518 |
| 204452_s_at | 6.452734953 | frizzled homolog 1 (Drosophila) | 94234 |
| 205715_at | 6.431601459 | bone marrow stromal cell antigen 1 | 169998 |
| 216942_s_at | 6.423538729 | CD58 antigen, (lymphocyte function-associated antigen 3) | 75626 |
| 218217_at | 6.419305978 | likely homolog of rat and mouse retinoid-inducible serine carboxypeptidase | 431107 |
| 212192_at | 6.414029336 | hypothetical protein BC013764 | 109438 |
| 200868_s_at | 6.392116081 | zinc finger protein 313 | 144949 |
| 202912_at | 6.388963292 | adrenomedullin | 441047 |
| 207691_x_at | 6.371699946 | ectonucleoside triphosphate diphosphohydrolase 1 | 444105 |
| 209124_at | 6.322399002 | myeloid differentiation primary response gene (88) | 82116 |
| 204620_s_at | 6.310710071 | chondroitin sulfate proteoglycan 2 (versican) | 434488 |
| 203535_at | 6.299810247 | S100 calcium binding protein A9 (calgranulin B) | 112405 |
| 202878_s_at | 6.290011829 | complement component 1, q subcomponent, receptor 1 | 97199 |
| 204249_s_at | 6.286305359 | LIM domain only 2 (rhombotin-like 1) | 283063 |
| 208872_s_at | 6.266531252 | polyposis locus protein 1 | 173119 |
| 205603_s_at | 6.253379078 | diaphanous homolog 2 (Drosophila) | 226483 |

TABLE 4-continued

Ischemic stroke related-genes using Westfall and Young correction.

| Affy ID # | t-statistic* | Gene Name | UniGene ID No. |
|---|---|---|---|
| 208818_s_at | 6.203109452 | catechol-O-methyltransferase | 240013 |
| 205158_at | 6.200940206 | ribonuclease, RNase A family, 4 | 283749 |
| 200765_x_at | 6.192889656 | catenin (cadherin-associated protein), alpha 1, 102 kDa | 254321 |
| 220615_s_at | 6.13260793 | hypothetical protein FLJ10462 | 134497 |
| 202897_at | 6.131315699 | protein tyrosine phosphatase, non-receptor type substrate 1 | 156114 |
| 204222_s_at | 6.124530943 | GLI pathogenesis-related 1 (glioma) | 511765 |
| 201743_at | 6.115549767 | CD14 antigen | 75627 |
| 211744_s_at | 6.052175772 | CD58 antigen, (lymphocyte function-associated antigen 3) | 75626 |
| 207168_s_at | 6.04197964 | H2A histone family, member Y | 75258 |
| 220034_at | 6.041558439 | interleukin-1 receptor-associated kinase 3 | 268552 |
| 204099_at | 6.027517093 | SWI/SNF related, matrix associated, actin dependent regulator of chromatin, subfamily d, member 3 | 444445 |
| 212335_at | 6.016778906 | glucosamine (N-acetyl)-6-sulfatase (Sanfilippo disease IIID) | 334534 |
| 211135_x_at | 6.012317836 | leukocyte immunoglobulin-like receptor, subfamily B (with TM and ITIM domains), member 3 | 511766 |
| 203127_s_at | 5.986287131 | serine palmitoyltransferase, long chain base subunit 2 | 59403 |
| 201041_s_at | 5.975259394 | dual specificity phosphatase 1 | 171695 |
| 209949_at | 5.974963258 | neutrophil cytosolic factor 2 (65 kDa, chronic granulomatous disease, autosomal 2) | 949 |
| 203922_s_at | 5.957917579 | cytochrome b-245, beta polypeptide (chronic granulomatous disease) | 88974 |
| 200838_at | 5.956269465 | cathepsin B | 135226 |
| 210844_x_at | 5.934193387 | catenin (cadherin-associated protein), alpha 1, 102 kDa | 254321 |
| 200886_s_at | 5.905731995 | phosphoglycerate mutase 1 (brain) | 447492 |
| 208949_s_at | 5.888003927 | lectin, galactoside-binding, soluble, 3 (galectin 3) | 411701 |
| 211284_s_at | 5.872375053 | granulin | 180577 |
| 210992_x_at | 5.781422168 | Fc fragment of IgG, low affinity IIa, receptor for (CD32) | 352642 |
| 204860_s_at | 5.767559943 | *Homo sapiens* transcribed sequence with strong similarity to protein sp: Q13075 (*H. sapiens*) BIR1_HUMAN Baculoviral IAP repeat-containing protein 1 (Neuronal apoptosis inhibitory protein) | 508565 |
| 212788_x_at | 5.750811183 | ferritin, light polypeptide | 433670 |
| 211776_s_at | 5.744898203 | erythrocyte membrane protein band 4.1-like 3 | |
| 221731_x_at | 5.740750361 | chondroitin sulfate proteoglycan 2 (versican) | 434488 |
| 210225_x_at | 5.740595562 | leukocyte immunoglobulin-like receptor, subfamily B (with TM and ITIM domains), member 3 | 511766 |
| 218404_at | 5.731267464 | sorting nexin 10 | 418132 |
| 214511_x_at | 5.713985599 | Fc fragment of IgG, high affinity Ia, receptor for (CD64) | 77424 |
| 200764_s_at | 5.672422269 | catenin (cadherin-associated protein), alpha 1, 102 kDa | 254321 |
| 210904_s_at | 5.667948907 | interleukin 13 receptor, alpha 1 | 285115 |
| 201200_at | 5.649460774 | cellular repressor of E1A-stimulated genes | 5710 |
| 209189_at | 5.649122471 | v-fos FBJ murine osteosarcoma viral oncogene homolog | 25647 |
| 202943_s_at | 5.621772605 | N-acetylgalactosaminidase, alpha- | 75372 |
| 201329_s_at | 5.609807116 | v-ets erythroblastosis virus E26 oncogene homolog 2 (avian) | 292477 |
| 200678_x_at | 5.592069508 | granulin | 180577 |
| 200839_s_at | 5.591102824 | cathepsin B | 135226 |
| 204053_x_at | 5.588909808 | phosphatase and tensin homolog (mutated in multiple advanced cancers 1) | 253309 |
| 204759_at | 5.575108906 | chromosome condensation 1-like | 27007 |
| 217897_at | 5.56972714 | FXYD domain containing ion transport regulator 6 | 410748 |
| 203973_s_at | 5.569117146 | KIAA0146 protein | 381058 |
| 210951_x_at | 5.548465566 | RAB27A, member RAS oncogene family | 298530 |
| 216041_x_at | 5.547562803 | granulin | 180577 |
| 208454_s_at | 5.541919824 | plasma glutamate carboxypeptidase | 197335 |
| 209970_x_at | 5.529207916 | caspase 1, apoptosis-related cysteine protease (interleukin 1, beta, convertase) | 2490 |
| 204646_at | 5.502178632 | dihydropyrimidine dehydrogenase | 1602 |

TABLE 4-continued

Ischemic stroke related-genes using Westfall and Young correction.

| Affy ID # | t-statistic* | Gene Name | UniGene ID No. |
|---|---|---|---|
| 202990_at | 5.497661918 | phosphorylase, glycogen; liver (Hers disease, glycogen storage disease type VI) | 282417 |
| 218606_at | 5.492492596 | zinc finger, DHHC domain containing 7 | 9725 |
| 219316_s_at | 5.477939952 | chromosome 14 open reading frame 58 | 267566 |
| 207574_s_at | 5.470945076 | growth arrest and DNA-damage-inducible, beta | 110571 |
| 212807_s_at | 5.462951979 | sortilin 1 | 394609 |
| 214875_x_at | 5.462919125 | amyloid beta (A4) precursor-like protein 2 | 279518 |
| 202446_s_at | 5.457954078 | phospholipid scramblase 1 | 348478 |
| 210784_x_at | 5.416225005 | leukocyte immunoglobulin-like receptor, subfamily B (with TM and ITIM domains), member 3 | 511766 |
| 203561_at | 5.415498696 | Fc fragment of IgG, low affinity IIa, receptor for (CD32) | 352642 |
| 210152_at | 5.408887988 | leukocyte immunoglobulin-like receptor, subfamily B (with TM and ITIM domains), member 4 | 67846 |
| 210427_x_at | 5.374221003 | annexin A2 | 462864 |
| 212830_at | 5.373953889 | EGF-like-domain, multiple 5 | 236216 |
| 204169_at | 5.36588724 | IMP (inosine monophosphate) dehydrogenase 1 | 317095 |
| 213620_s_at | −5.435839683 | intercellular adhesion molecule 2 | 433303 |
| 38269_at | −5.579245846 | protein kinase D2 | 205431 |
| 209603_at | −5.950691641 | GATA binding protein 3 | 169946 |
| 219798_s_at | −5.971011322 | hypothetical protein FLJ20257 | 178011 |
| 210038_at | −6.173613284 | protein kinase C, theta | 408049 |

*Positive t-statistic indicates that the gene is upregulated following an ischemic stroke. Negative t-statistic indicates that the gene is downregulated following an ischemic stroke.

^UniGene ID number is system for automatically partitioning GenBank sequences into a non-redundant set of gene-oriented clusters. Each UniGene cluster contains sequences that represent a unique gene, as well as related information such as the tissue types in which the gene has been expressed and map location. UniGene numbers can be searched on the NCBI website.

In contrast to the Benjamini and Yekutieli approach, the Westfall and Young approach limits the probability of making even one false positive declaration at 5%. There was a predominant up-regulation pattern with 77/82 genes up-regulated and 5 down-regulated (Table 4).

After PAM correction, 28 gene probes, corresponding to 22 genes were found to be significantly different (Table 5). As shown in Table 5, several genes were upregulated following an ischemic stroke.

TABLE 5

Ischemic stroke related-genes using PAM correction.

| Affymetrix Probe ID | Name and Function |
|---|---|
| | White Blood Cell Activation and Differentiation |
| 215049_x_at | CD163 |
| 218454_at | Hypothetical protein FLJ22662 Laminin A motif |
| 211404_s_at | Amyloid beta (A4) precursor-like protein 2 |
| 221210_s_at | N-acetylneuraminate pyruvate lysase |
| 209189_at | v-fos FBJ murine osteosarcoma viral oncogene homolog |
| 204924_at | Toll-like receptor 2 |
| 211571_s_at | Chondroitin sulfate proteoglycan 2 (versican) |
| 211612_s_at | Interleukin 13 receptor, alpha 1 |
| 201743_at | CD14 antigen |
| 205715_at | Bone marrow stromal cell antigen 1/CD157 |
| 202878_s_at | Complement component 1, q subcomponent, receptor 1 |
| 219788_at | Paired immunoglobin-like type 2 receptor alpha |
| 214511_x_at | Fc fragment of IgG, high affinity Ia, receptor for (CD64) |
| | Vascular Repair |
| 203888_at | Thrombomodulin |
| 207691_x_at | Ectonucleoside triphosphate diphosphohydrolase 1 |
| 206488_s_at | CD36 antigen (collagen type I receptor, thrombospondin receptor) |
| | Response to Hypoxia |
| 202912_at | Adrenomedullin |
| 201041_s_at | Dual specificity phosphatase 1 |
| 203922_s_at | Cytochrome b-245, beta polypeptide (chronic granulomatous disease) |

TABLE 5-continued

Ischemic stroke related-genes using PAM correction.

| Affymetrix Probe ID | Name and Function |
| --- | --- |
| 208771_s_at | Leukotriene A4 hydrolase |
| 201328_at | Erythroblastosis virus E26 oncogene homolog 2 (avian) |
| 209949_at | Neutrophil cytosolic factor 2 (65 kDa, chronic granulomatous disease, autosomal 2) |
| | Response to Altered Cerebral Microenvironment |
| 208818_s_at | Catechol-O-methyltransferase |
| 200648_s_at | Glutamate-ammonia ligase (glutamine ligase) |
| 202917_s_at | S100 calcium binding protein A8 (calgranulin A) |
| 204860_s_at | Neuronal apoptosis inhibitory protein: *Homo sapiens* transcribed sequence with strong similarity to protein sp: Q13075 (*H. sapiens*) BIR1_HUMAN Baculoviral IAP repeat-containing protein 1 |
| 212807_s_at | Sortilin |
| 202446_s_at | Phospholipid scramblase 1 |
| 211067_s_at | Growth-arrest-specific 7 |
| 204222_s_at | GLI pathogenesis-related 1 (glioma) |

Table 6 provides a summary of the number of ischemic-stroke related genes found using different correction methods.

TABLE 6

Number of genes different between stroke and control subjects by multiple comparison correction filter.*

| Multiple comparison filter | No. of genes |
| --- | --- |
| PAM dataset | 22 |
| Westfall and Young dataset | 82 |
| Bonferroni correction set | 231 |
| Benjamini & Yekutieli set | 771 |
| Raw p value list | 5060 |

*There were 22,283 gene probes on the microarray. The most conservative multiple comparison correction is the PAM dataset, then the Westfall and Young and Bonferroni dataset followed by the Benjamini & Yekutieli dataset.

Example 4

Classes of Gene Expression Increased Following Ischemic Stroke

This example describes the four classes of genes whose expression was increased following ischemic stroke, based on the results obtained in Example 3.

A number of broad classes of gene expression were found (representative examples are shown in Table 5 above). The first were genes that indicated differentiation of monocytes into macrophages and lymphocyte activation (for example, CD14, toll-like receptor 2 and FcR2a). Concomitantly, a number of genes for cell cycle arrest were up-regulated. Some other up-regulated genes were for cytoskeletal proteins (for example, alpha-catenin and galectin 3) involved in anchoring of white blood cells to tissue.

The second main grouping was related to hypoxia, many being inducible by hypoxia inducible factor-1 (for example, adrenomedullin, FcR2a and CD14). There may be a common promoter region for hypoxia inducible factor-1.

A third class of genes is related to vascular repair. For example, up-regulation of ectonucleoside triphosphate diphosphohydrolase 1 results in decreased platelet interaction and aggregation.

The fourth broad class of genes is related to a specific PBMC response to the altered cerebral microenvironment.

Surprisingly, no specific steroid stress-related genes were identified.

In summary, the gene classes demonstrate both specific and non-specific gene expression in PBMCs during acute ischemic stroke. The finding of genes induced by hypoxic stress, vascular repair genes and neuronal specific genes demonstrates a specific response to ischemic stroke.

Example 5

Predicting Severity and Neurological Recovery of Ischemic Stroke

This example describes methods used to analyze PBMCs isolated from 26 subjects at three time-points following ischemic stroke, to demonstrate that there is a correlation between recovery and alterations in gene expression.

Expression of the 22 genes listed in Table 5 was determined using the methods described in the above examples in a second and independent series of 26 patients studied two years after the initial series. These patients had blood samples drawn at day 1 (within 24 hours of onset of symptoms), day 7-14 and day 90 post stroke (26 subjects had blood draws at day 1, 25 subjects had a blood draw at day 7-14 and 21 subjects had a blood draw at day 90 [some patients were deceased by this time]). At day 1, detecting differential gene expression in the 22 genes accurately classified 81% of subjects (21/26) as having had an ischemic stroke. The 5 subjects classified as control (that is, subjects classified as not having had an ischemic stroke) using the method tended to be younger or to have mild stroke severity scores. These results confirm the diagnostic accuracy of the PAM list (Table 5) for acute stroke diagnosis (shown in Table 9), as this was the second independent series of subjects on which these results have been confirmed.

At days 7-14, detecting differential gene expression in the 22 genes accurately classified 64% of subjects (16/25) as having had an ischemic stroke. At day 90, detecting differential gene expression in the 22 genes accurately classified 62% of subjects (13/21) as having had an ischemic stroke. Without wishing to be bound to a particular theory, it is proposed that the persistent gene changes of ischemic stroke at the day 7-14 and day 90 time points reflects ongoing inflammatory or other processes related to the stroke or a lack of recovery of these processes. Those who remained classified as a stroke at these time points were those with the more severe strokes and worse outcomes (see below).

The recovery of the subjects was compared to their classification determined using the 22 genes listed in Table 5. An excellent recovery was defined as a Barthel score of 100 at three months post stroke (for example see Mahoney et al., *Md. State Med. J.* 14:61-5, 1965). The Barthel score is a measure of 10 activities of daily living such as getting dressed, walking, going to the toilet. The score ranges from 100 (fully independent) to 0 (totally dependent and incapacitated or deceased).

In terms of excellent stroke recovery, all 9/9 (100%) patients who were classified as a control at their last measurement (whether classified as a stroke or a control at the first time point) had excellent recovery. In contrast only 8/17 (47%) patients who remained classified as a stroke at their last follow-up measurement (at day 7-14 in 3 patients who died and day 90 in the remaining) had excellent stroke recovery (p=0.008). This indicates persistence of the stroke state is related to changes in gene expression.

Therefore, it appears that the reason that some of the subjects were indicated to not have had an ischemic stroke is that they recovered by day 90. Therefore, the disclosed ischemic stroke related molecules, such as those listed in Tables 2-5, for example those listed in Table 5 can be used to be determine the prognosis of a subject who has had an ischemic stroke.

In view of these results, disclosed are methods of stratifying the seriousness of a stroke, and assessing the likely neurological recovery of the subject. For example, stratification or assessing the likely neurological recovery of the subject can be performed as early as one day (or within 24 hours) after the ischemic stroke, 7-14 days after the ischemic stroke, or 90 days after the ischemic stroke. In particular examples, the method includes detecting differential expression in at least four ischemic stroke-related molecules, such as at least the 22 genes (or corresponding proteins) listed in Table 5. Detection of increased expression of at least four ischemic stroke-related molecules, such as at least the 22 genes (or corresponding proteins) listed in Table 5, indicates that the stroke was severe and the subject has a lower probability of neurological recovery (for example as compared to an amount of expected neurological recovery in a subject who did not have increased expression of the 22 genes/proteins listed in Table 5). In particular examples, the increased expression is determined by calculating a t-statistic value, wherein a t-statistic value of at least 3, at least 5.3, or at least 6 indicates that expression is increased.

In particular examples, the assay results can predict a Barthel score of at least 45, for example at least 50, 90 or 100, as an indication of neurological recovery.

Example 6

Temporal Relationship of Evaluating a Stroke

This example describes the temporal relationship of the disclosed methods to the stroke or suspected stroke. The assay can be performed following the onset of signs and symptoms associated with ischemic stroke. Particular examples of signs and symptoms associated with ischemic stroke include but are not limited to: headache, sensory loss (such as numbness, particularly confined to one side of the body or face), paralysis (such as hemiparesis), pupillary changes, blindness (including bilateral blindness), ataxia, memory impairment, dysarthria, somnolence, and other effects on the central nervous system recognized by those of skill in the art.

A sample can be obtained from the subject (such as a PBMC sample) and analyzed using the disclosed methods, for example, within 1 hour, within 6 hours, within 12 hours, or even within 24 hours of having signs or symptoms associated with ischemic stroke. In another example, a sample is obtained at least 7 days later following the onset of signs and symptoms associated with ischemic stroke, such as within 7-14 days of having signs or symptoms associated with ischemic stroke, or within 90 days.

In particular examples, the assay can be performed after a sufficient period of time for the differential regulation of the genes (or proteins) to occur, for example at least 24 hours after onset of the symptom or constellation of symptoms that have indicated a potential cerebral ischemic event. In other examples it occurs prior to performing any imaging tests are performed to find anatomic evidence of ischemic stroke. Moreover, it is often difficult for imaging modalities (such as CT and MRI) to detect acute ischemic strokes, at least until brain changes (such as edema) have taken place in response to the ischemia. Hence the assay described herein in particular examples is able to detect the ischemic stroke even before definitive brain imaging evidence of the stroke is known.

Since the results of this assay are also highly reliable predictors of the ischemic nature of the stroke, the results of the assay can also be used (for example in combination with other clinical evidence and brain scans) to determine whether thrombolytic therapy designed to lyse a neurovascular occlusion such as a thrombus (for example by using tissue plasminogen activator or streptokinase) should be administered to the subject. In certain example, thrombolytic therapy is given to the subject once the results of the differential gene assay are known if the assay provides an indication that the stroke is ischemic in nature.

Moreover, the neurological sequelae of an ischemic event in the central nervous system can have consequences that range from the insignificant to the devastating, and the disclosed assay permits early and accurate stratification of risk of long-lasting neurological impairment. For example, a test performed as early as within the first 24 hours of onset of signs and symptoms of a stroke, and even as late as 7-14 days or even as late as 90 days or more after the event can provide clinical data that is highly predictive of the eventual care needs of the subject.

The disclosed assay is also able to identify subjects who have had an ischemic stroke in the past, for example more than 2 weeks ago, or even more than 90 days ago. The identification of such subjects helps evaluate other clinical data (such as neurological impairment or brain imaging information) to determine whether an ischemic stroke has occurred. Subjects identified or evaluated in this manner can then be provided with appropriate treatments, such as anti-platelet agents (for example aspirin) that would be appropriate for a subject identified as having had an ischemic stroke but not as appropriate for subject who have had a hemorrhagic stroke. It is helpful to be able to classify subject as having had an ischemic stroke, because the treatments for ischemic stroke are often distinct from the treatments for hemorrhagic stroke. In fact, treating a hemorrhagic stroke with a therapy designed for an ischemic stroke (such as a thrombolytic agent) can have devastating clinical consequences. Hence using the results of the disclosed assay to help distinguish ischemic from hemorrhagic stroke offers substantial clinical benefit, and allows subjects to be selected for treatments appropriate to ischemic stroke but not hemorrhagic stroke.

Example 7

Quantitative Real Time Polymerase Chain Reaction

This example describes the use of quantitative real time polymerase chain reaction to confirm results obtained using the microarrays.

Quantitative real time polymerase chain reaction of gene expression levels were performed using RNA samples from 10 patients and 9 controls. Nine genes were selected for analysis on the basis of their significantly high expression in the index set. One further gene, not up-regulated in the permutation dataset was selected as a negative control. Primers were obtained from the published literature and ordered from Invitrogen (Carlsbad, Calif.) as listed in Table 7.

TABLE 7

Primers for real time-PCR

| Gene | GenBank ID No | Primer Forward* | Primer reverse* |
|---|---|---|---|
| Adreno-medullin | NM_001124 | CGAAAGAAGTGGAATAAGTGGGC (1) | CCGCAGTTCCCTCTTCCC (2) |
| CD14 | NM_000591 | CAAGGTACTGAGCATTGCCCA (3) | TGTTCGCAGGAAAAGGCAG (4) |
| CD36 | M24795 | GATGCAGCCTCATTTCCACCT (5) | AGGCCTTGGATGGAAGAACA (6) |
| Caspase 1 | NM_033292 | GACCCGAGCTTTGATTGACTCC (7) | TTGATCTGCTGAGAGTCGCAGC (8) |
| a-Catenin | BC000385 | GATGACCGTCGTGAGCGAATT (9) | TTACGTCCAGCATTGCCCA (10) |
| FcR2a | NM_021642 | GACTGTGCTTTCCGAATGGCT (11) | TGACCTTGACCAGAGGCTTGTC (12) |
| FcER1a | NM_002001. | AGATGGCGTGTTAGCAGTCCCT (13) | GCCATTGTGGAACCATTTGG (14) |
| Cathepsin B | NM_147781 | CTGGCTGGTTGCCAACTCC (15) | AAAGAAGCCATTGTCACCCCA (16) |
| TRL2 | BC033756. | TCGGCGTTCTCTCAGGTGAC (17) | TGCAACACCAAACACTGGGAG (18) |
| INFGR1 | BC005333 | AGAATTTGCTGTATGCCGAGATG (19) | TGATATCCAGTTTAGGTGGTCCAAT (20) |

*SEQ ID NOS: shown in parenthesis.

Real time PCR was performed with an Opticon 2 (MJ research). Real time PCR results between patients and controls were compared using non-parametric statistics (Mann Whitney U tests).

As shown in Table 8, expression values derived from the microarrays correlated with RT-PCR for 9 up-regulated genes. Using RT-PCR, higher values for 8/9 genes in the up-regulated list were found, with a significant difference in 7/9 genes between 10 patients and 9 controls. A negative control was also included (gene not up-regulated in the permutation dataset) with no significant difference observed between patients who suffered a stroke and controls.

TABLE 8

Correlation of expression data with real time-PCR values

| Gene Name | Genbank ID | Median Patients n = 10 | Median Controls n = 9 | p |
|---|---|---|---|---|
| Up-regulated in Westfall and Young Set | | | | |
| Adrenomedullin | NM_001124 | 1.295 | 0.39 | 0.0015 |
| CD14 | NM_000591 | 2.207 | 1.094 | 0.0003 |
| CD36 | M24795 | 2.08 | 1.23 | 0.02 |
| Caspase 1 | NM_033292 | 14.24 | 6.62 | 0.0041 |
| a-Catenin | BC000385 | 2.559 | 1.5487 | 0.0789 |
| FcR2a | NM_021642 | 0.58 | 0.26 | 0.003 |
| FcER1a | NM_002001 | 2.655 | 2.87 | 0.9048 |
| Cathepsin B | NM_147781 | 0.9 | 0.32 | 0.0041 |
| Toll-like receptor 2 | BC033756 | 0.4939 | 0.1561 | 0.0021 |
| Not Up-regulated in Westfall and Young Set | | | | |
| INFGR1 | BC005333 | 0.985 | 0.64 | 0.1128 |

Using data from 9 patients and 10 controls and the PAM, stroke was prospectively classified with a sensitivity of 78% and a specificity of 80% (Table 9).

TABLE 9

Accuracy of training dataset in the prediction of stroke.*

| | Sensitivity | Specificity | Positive Predictive Value | Negative Predictive Value |
|---|---|---|---|---|
| No. | 7/9 | 8/10 | 7/9 | 8/10 |
| % | 78 | 80 | 78 | 80 |

*An independent cohort of 9 stroke patients and 10 controls was used. Using a nearest shrunken centroid algorithm, stroke was classified with a sensitivity of 78% and a specificity of 80%.

In summary, a distinct genomic profile of acute ischemic stroke in the peripheral blood mononuclear cells was identified. In addition, four broad classes of ischemic stroke related genes were identified that are upregulated following an ischemic stroke: white blood cell activation and differentiation genes, genes associated with hypoxia, vascular repair genes and genes associated with an altered cerebral microenvironment, including neuronal apoptosis inhibitory protein.

Example 8

Array for Evaluating a Stroke

This example describes particular arrays that can be used to evaluate a stroke, for example to diagnose an ischemic stroke.

In one example, the array includes probes (such as an oligonucleotide or antibody) that can recognize at least one gene (or protein) that is upregulated following an ischemic stroke, such as one or more of CD163; hypothetical protein FLJ22662 Laminin A motif; BST-1; FcγRI; baculoviral IAP repeat-containing protein 1; and KIAA0146, or any 1, 2, 3, 4, 5, or 6 of these. For example, the array can include a probe (such as an oligonucleotide or antibody) recognizes CD163. In yet another example, the array includes probes (such as an oligonucleotide or antibody) that can recognize at least one gene (or protein) that is downregulated following an ischemic stroke, such as one or more of intercellular adhesion molecule 2; protein kinase D2; GATA binding protein 3; hypothetical protein FLJ20257; or protein kinase C, theta. In a particular example, the array includes probes (such as an oligonucleotide or antibody) that can recognize at least one gene (or protein) that is upregulated following an ischemic stroke (such as at least one of CD163; hypothetical protein FLJ22662 Laminin A motif; BST-1; FcγRI; baculoviral IAP repeat-containing protein 1; and KIAA0146) and at least one gene (or protein) that is downregulated following an ischemic stroke (such as one or more of intercellular adhesion molecule 2; protein kinase D2; GATA binding protein 3; hypothetical protein FLJ20257; or protein kinase C, theta).

Other examplary probes that can be used are listed in Tables 2-5 and are identified by their Affymetrix identification number. The disclosed oligonucleotide probes can further include one or more detectable labels, to permit detection of hybridization signals between the probe and a target sequence.

In one example, the array includes probes (such as an oligonucleotide or antibody) that recognize any combination of at least four different genes (or proteins) listed in Tables 2-5. In particular examples, the array includes probes recognize all 22 genes (or proteins) listed in Table 5. The accuracy of the PAM list (Table 5) to diagnose ischemic acute stroke has been confirmed in two independent series of subjects. The ability of the PAM list (Table 5) to provide an indication of the severity of the stroke and to determine the likelihood of neurological recovery has also been demonstrated. In some examples, the array includes oligonucleotides, proteins, or antibodies that recognize any combination of at least one gene from each of the four classes listed in Table 5 (such as at least 2 or at least 3 genes from each class).

In another example, the array includes probes (such as an oligonucleotide or antibody) that recognize any combination of at least 150 different genes listed in Table 3 or all 190 genes listed in Table 3. In yet another example, the array includes probes that recognize at least 500 different genes listed in Table 2. In particular examples, the probes recognize all 637 genes listed in Table 2.

Compilation of "loss" and "gain" of hybridization signals will reveal the genetic status of the individual with respect to the ischemic stroke-associated genes listed in Tables 2-5.

Example 9

Quantitative Spectroscopic Methods

This example describes quantitative spectroscopic approaches methods, such as SELDI, that can be used to detect differential protein expression of ischemic stroke related proteins.

In one example, surface-enhanced laser desorption-ionization time-of-flight (SELDI-TOF) mass spectrometry is used to detect changes in differential protein expression, for example by using the ProteinChip™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586, all herein incorporated by reference). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as ischemic stroke related proteins. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as ischemic stroke related proteins) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that recognize ischemic stroke related proteins. In one example, antibodies are immobilized onto the surface using a bacterial Fc binding support. The chromatographic surface is incubated with a sample from the subject, such as a sample that includes PMBC proteins (such as a PBMC lysate). The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

Example 10

Nucleic Acid-Based Analysis

The ischemic stroke-related nucleic acid molecules provided herein (such as those disclosed in Tables 2-5) can be used in evaluating a stroke, for example for determining whether a subject has had an ischemic stroke, determining the severity or likely neurological recovery of a subject who has had an ischemic stroke, and determining a treatment regimen for a subject who has had an ischemic stroke. For such procedures, a biological sample of the subject is assayed for an increase or decrease in expression of ischemic stroke-related nucleic acid molecules, such as those listed in Tables 2-5. Suitable biological samples include samples containing genomic DNA or RNA (including mRNA) obtained from cells of a subject, such as those present in peripheral blood, urine, saliva, tissue biopsy, surgical specimen, amniocentesis samples and autopsy material. In a particular example, the sample includes PBMCs (or components thereof, such as nucleic acids or proteins isolated from PBMCs).

The detection in the biological sample of increased or decreased expression in four or more ischemic stroke-related nucleic acid molecules, such any combination of four or more molecules listed in Table 5, 150 or more molecules listed in Table 3, or 500 or more molecules listed in Table 2, can be achieved by methods known in the art. In some examples, expression is determined for any combination of at least one gene from each class listed in Table 5 (such as at least 2 or at least 3 genes from each class). In some examples, expression is determined for at least CD163; hypothetical protein FLJ22662 Laminin A motif, BST-1; FcγRI; baculoviral IAP repeat-containing protein 1; and KIAA0146.

Increased or decreased expression of an ischemic stroke-related molecule also can be detected by measuring the cellular level of ischemic stroke-related nucleic acid molecule-specific mRNA. mRNA can be measured using techniques well known in the art, including for instance Northern analysis, RT-PCR and mRNA in situ hybridization. Details of mRNA analysis procedures can be found, for instance, in provided examples and in Sambrook et al. (ed.), *Molecular Cloning: A Laboratory Manual,* 2nd ed., vol. 1-3, Cold Spring Harbor Laboratory Press, Cold Spring Harbor, N.Y., 1989.

Oligonucleotides specific to ischemic stroke-related sequences can be chemically synthesized using commercially available machines. These oligonucleotides can then be labeled, for example with radioactive isotopes (such as $^{32}$P) or with non-radioactive labels such as biotin (Ward and Langer et al., *Proc. Natl. Acad. Sci. USA* 78:6633-57, 1981) or a fluorophore, and hybridized to individual DNA samples immobilized on membranes or other solid supports by dot-blot or transfer from gels after electrophoresis. These specific sequences are visualized, for example by methods such as autoradiography or fluorometric (Landegren et al., *Science* 242:229-37, 1989) or colorimetric reactions (Gebeyehu et al., *Nucleic Acids Res.* 15:4513-34, 1987).

Nucleic acid molecules isolated from PBMCs can be amplified using routine methods to form nucleic acid amplification products. These nucleic acid amplification products can then be contacted with an oligonucleotide probe that will hybridize under stringent conditions with an ischemic stroke-related nucleic acid. The nucleic acid amplification products which hybridize with the probe are then detected and quantified. The sequence of the oligonucleotide probe can bind specifically to a nucleic acid molecule represented by the sequences listed in Tables 2-5.

Example 11

Protein-Based Analysis

This example describes methods that can be used to detect changes in expression of ischemic stroke-related proteins. Ischemic stroke-related protein sequences can be used in methods of evaluating a stroke, for example for determining whether a subject has had an ischemic stroke, determining the severity or likely neurological recovery of a subject who has had an ischemic stroke, and determining a treatment regimen for a subject who has had an ischemic stroke. For such procedures, a biological sample of the subject is assayed for a change in expression (such as an increase or decrease) of any combination of at least four ischemic stroke-related proteins, such as any combination of at least four of those listed in Table 5, at least 150 of those listed in Table 3, or at least 500 of those listed in Table 2. In some examples, protein expression is determined for any combination of at least one gene from each of the four classes of genes listed in Table 5 (such as at least 2 or at least 3 genes from each of the four classes of genes listed in Table 5). In some examples, protein expression is determined for at least CD163; hypothetical protein FLJ22662 Laminin A motif; BST-1; FcγRI; baculoviral IAP repeat-containing protein 1; and KIAA0146.

Suitable biological samples include samples containing protein obtained from cells of a subject, such as those present in peripheral blood. A change in the amount of four or more ischemic stroke-related proteins in a subject, such as an increase in four or more ischemic stroke-related proteins listed in Table 5, can indicate that the subject has suffered an ischemic stroke.

The determination of increased or decreased ischemic stroke-related protein levels, in comparison to such expression in a normal subject (such as a subject who has not previously had an ischemic stroke), is an alternative or supplemental approach to the direct determination of the expression level of ischemic stroke-related nucleic acid sequences by the methods outlined above. The availability of antibodies specific to ischemic stroke-related protein(s) will facilitate the detection and quantitation of ischemic stroke-related protein(s) by one of a number of immunoassay methods that are well known in the art, such as those presented in Harlow and Lane (*Antibodies, A Laboratory Manual*, CSHL, New York, 1988). Methods of constructing such antibodies are known in the art.

Any standard immunoassay format (such as ELISA, Western blot, or RIA assay) can be used to measure ischemic stroke-related protein levels. A comparison to wild-type (normal) ischemic stroke-related protein levels and an increase or decrease in ischemic stroke-related polypeptide levels (such as an increase in any combination of at least 4 proteins listed in Table 5 or a decrease in any combination of at least 4 proteins listed in Tables 2-4 with a negative t-statistic) is indicative of ischemic stroke. Immunohistochemical techniques can also be utilized for ischemic stroke-related protein detection and quantification. For example, a tissue sample can be obtained from a subject, and a section stained for the presence of an ischemic stroke-related protein using the appropriate ischemic stroke-related protein specific binding agents and any standard detection system (such as one that includes a secondary antibody conjugated to horseradish peroxidase). General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating ischemic stroke-related proteins, a biological sample of the subject that includes cellular proteins can be used. Quantitation of an ischemic stroke-related protein can be achieved by immunoassay and the amount compared to levels of the protein found in cells from a subject who has not had an ischemic stroke. A significant increase in the amount of four or more ischemic stroke-related proteins in the cells of a subject compared to the amount of the same ischemic stroke-related protein found in normal human cells is usually at least 2-fold, at least 3-fold, at least 4-fold or greater difference. Substantial overexpression of four or more ischemic stroke-related protein(s) can be indicative of an ischemic stroke. Similarly, a significant decrease in the amount of four or more ischemic stroke-related proteins in the cells of a subject compared to the amount of the same ischemic stroke-related protein found in normal human cells is usually at least 2-fold, at least 3-fold, at least 4-fold or greater difference. Substantial underexpression of four or more ischemic stroke-related protein(s) can be indicative of an ischemic stroke or poor prognosis.

An alternative method of evaluating a stroke is to quantitate the level of four or more ischemia-related proteins in a subject, for instance in the cells of the subject. This diagnostic tool is useful for detecting reduced or increased levels of ischemia-related proteins, for instance, though specific techniques can be used to detect changes in the size of proteins, for instance. Localization or coordinated expression (temporally or spatially) of ischemia-related proteins can also be examined using well known techniques.

Example 12

Kits

Kits are provided for evaluating a stroke, for example for determining whether a subject has had an ischemic stroke, determining the severity or likely neurological recovery of a subject who has had an ischemic stroke, and determining a treatment regimen for a subject who has had an ischemic stroke (such as kits containing ischemic stroke detection arrays). Kits are also provided that contain the reagents need to detect hybridization complexes formed between oligonucleotides on an array and ischemic stroke-related nucleic acid molecules obtained from a subject, or between proteins or antibodies on an array and proteins obtained from a subject suspected of having had (or known to have had) an ischemic stroke. These kits can each include instructions, for instance instructions that provide calibration curves or charts to compare with the determined (such as experimentally measured) values. The disclosed kits can include reagents needed to determine gene copy number (genomic amplification or deletion), such as probes or primers specific for an ischemia-related nucleic acid sequence.

Kits are provided to determine the level (or relative level) of expression or of any combination of four or more ischemic stroke-related nucleic acids (such as mRNA) or ischemic stroke-related proteins (such as kits containing nucleic acid probes, proteins, antibodies, or other ischemic stroke-related protein specific binding agents) listed in Tables 2-5.

Kits are provided that permit detection of ischemic stroke-related mRNA expression levels (including over- or under-expression, in comparison to the expression level in a control sample). Such kits include an appropriate amount of one or more of the oligonucleotide primers for use in, for instance, reverse transcription PCR reactions, and can also include reagents necessary to carry out RT-PCR or other in vitro amplification reactions, including, for instance, RNA sample preparation reagents (such as an RNAse inhibitor), appropriate buffers (such as polymerase buffer), salts (such as magnesium chloride), and deoxyribonucleotides (dNTPs).

In some examples, kits are provided with the reagents needed to perform quantitative or semi-quantitative Northern analysis of ischemic stroke-related mRNA. Such kits can include at least four ischemic stroke-related sequence-specific oligonucleotides for use as probes. Oligonucleotides can be labeled, for example with a radioactive isotope, enzyme substrate, co-factor, ligand, chemiluminescent or fluorescent agent, hapten, or enzyme.

Kits are provided that permit detection of ischemic stroke-related genomic amplification or deletion. Nucleotide sequences encoding an ischemic stroke-related protein, and fragments thereof, can be supplied in the form of a kit for use in detection of ischemic stroke-related genomic amplification/deletion or diagnosis of an ischemic stroke, progression of an ischemic stroke, or therapy assessment for subjects who have suffered an ischemic stroke. In examples of such a kit, an appropriate amount of one or more oligonucleotide primers specific for an ischemic stroke-related-sequence (such as those listed in Table 1) is provided in one or more containers. The oligonucleotide primers can be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers are provided in pre-measured single use amounts in individual, typically disposable, tubes, or equivalent containers. With such an arrangement, the sample to be tested for the presence of ischemic stroke-related genomic amplification/deletion can be added to the individual tubes and in vitro amplification carried out directly.

The amount of each primer supplied in the kit can be any amount, depending for instance on the market to which the product is directed. For instance, if the kit is adapted for research or clinical use, the amount of each oligonucleotide primer provided is likely an amount sufficient to prime several in vitro amplification reactions. Those of ordinary skill in the art know the amount of oligonucleotide primer that is appropriate for use in a single amplification reaction. General guidelines can be found in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, John Wiley & Sons, New York, 1998).

A kit can include more than two primers to facilitate the in vitro amplification of ischemic stroke-related genomic sequences, such as those listed in Tables 2-5, or the 5' or 3' flanking region thereof.

In some examples, kits also include the reagents needed to perform in vitro amplification reactions, such as DNA sample preparation reagents, appropriate buffers (for example polymerase buffer), salts (for example magnesium chloride), and deoxyribonucleotides (dNTPs). Written instructions can also be included. Kits can further include labeled or unlabeled oligonucleotide probes to detect the in vitro amplified sequences. The appropriate sequences for such a probe will be any sequence that falls between the annealing sites of two provided oligonucleotide primers, such that the sequence the probe is complementary to is amplified during the in vitro amplification reaction (if it is present in the sample).

One or more control sequences can be included in the kit for use in the in vitro amplification reactions. The design of appropriate positive and negative control sequences is well known to one of ordinary skill in the art.

In particular examples, a kit includes an array with oligonucleotides (or antibodies) that recognize any combination of at least four ischemic stroke-related sequences, such as any combination of at least four of those listed in Table 5, at least 22 of those listed in Table 5, at least 150 of those listed in Table 3, or at least 500 of those listed in Table 2. In one example, the array includes oligonucleotides (or antibodies) that recognize at least 1, at least 2, at least 3, at least 4, at least 5, or at least 6 of the following: CD163; hypothetical protein FLJ22662 Laminin A motif; BST-1; FcγRI; baculoviral IAP repeat-containing protein 1; and KIAA0146. For example, the array can include oligonucleotides (or antibodies) that recognize at least CD163; hypothetical protein FLJ22662 Laminin A motif; BST-1; FcγRI; baculoviral IAP repeat-containing protein 1; and KIAA0146.

In some examples, the array includes agents (such as oligonucleotides, proteins, or antibodies) that can recognize any combination of at least one gene (or protein) from each class listed in Table 5 (such as at least 2 or at least 3 genes (or proteins) from each class). The array can include other oligonucleotides, for example to serve as negative or positive controls. The oligonucleotides that recognize ischemic stroke-related and control sequences can be on the same array, or on different, arrays. Particular arrays are disclosed in Examples 7-9.

Kits are also provided for the detection of ischemic stroke-related protein expression, for instance increased expression of any combination of at least 4 proteins listed in Table 5. Such kits include one or more ischemic stroke-related proteins (full-length, fragments, or fusions) or specific binding agent (such as a polyclonal or monoclonal antibody or antibody fragment), and can include at least one control. The ischemic stroke-related protein specific binding agent and control can be contained in separate containers. The kits can also include agents for detecting ischemic stroke-related protein:agent complexes, for instance the agent can be detectably labeled. If the detectable agent is not labeled, it can be detected by second antibodies or protein A, for example, either of both of which also can be provided in some kits in one or more separate containers. Such techniques are well known.

Additional components in some kits include instructions for carrying out the assay. Instructions permit the tester to determine whether ischemic stroke-linked expression levels are elevated, reduced, or unchanged in comparison to a control sample. Reaction vessels and auxiliary reagents such as chromogens, buffers, enzymes, etc. can also be included in the kits.

Example 13

Gene Expression Profiles (Fingerprints)

With the disclosure of many ischemic stroke-related molecules (as represented for instance by those listed in Tables 2-5), gene expression profiles that provide information on evaluating a stroke, for example for determining whether a subject has had an ischemic stroke, determining the severity or likely neurological recovery of a subject who has had an ischemic stroke, and determining a treatment regimen for a subject who has had an ischemic stroke, are now enabled.

Ischemic stroke-related expression profiles include the distinct and identifiable pattern of expression (or level) of sets of ischemic stroke-related genes, for instance a pattern of increased and decreased expression of a defined set of genes, or molecules that can be correlated to such genes, such as mRNA levels or protein levels or activities. The set of molecules in a particular profile can include any combination of at least four of the sequences listed in any of Tables 2-5.

Another set of molecules that could be used in a profile include any combination of at least four sequences listed in Table 5, each of which is overexpressed following an ischemic stroke. For example, an ischemic stroke-related gene expression profile can include one sequence from each of the following four classes of genes: white blood cell activation and differentiation genes, genes related to hypoxia, genes involved in vascular repair, and genes related to a specific PBMC response to the altered cerebral microenvironment. In another example, the molecules included in the profile include at least CD163; hypothetical protein FLJ22662 Laminin A motif; BST-1; FcγRI; baculoviral LAP repeat-containing protein 1; and KIAA0146, or any one of these.

Yet another example of a set of molecules that could be used in a profile would include any combination of at least 150 of the sequences listed in Table 3, whose expression is upregulated or downregulated following an ischemic stroke. In a particular example, a set of molecules that could be used in a profile would include any combination of at least 500 of the sequences listed in Table 2, whose expression is upregulated or downregulated following an ischemic stroke.

Particular profiles can be specific for a particular stage or age of normal tissue (such as PMBCs). Thus, gene expression profiles can be established for a pre-ischemic stroke tissue (such as normal tissue not subjected to an ischemic challenge or preconditioning) or an ischemic challenged tissue. Each of these profiles includes information on the expression level of at least four or more genes whose expression is altered following an ischemic stroke. Such information can include relative as well as absolute expression levels of specific genes. Likewise, the value measured can be the relative or absolute level of protein expression or protein activity, which can be correlated with a "gene expression level." Results from the gene expression profiles of an individual subject can be viewed in the context of a test sample compared to a baseline or control sample fingerprint/profile.

The levels of molecules that make up a gene expression profile can be measured in any of various known ways, which may be specific for the type of molecule being measured. Thus, nucleic acid levels (such as direct gene expression levels, such as the level of mRNA expression) can be measured using specific nucleic acid hybridization reactions. Protein levels can be measured using standard protein assays, using immunologic-based assays (such as ELISAs and related techniques), or using activity assays. Examples for measuring nucleic acid and protein levels are provided herein; other methods are well known to those of ordinary skill in the art.

Examples of ischemia-related gene expression profiles can be in array format, such as a nucleotide (such as polynucleotide) or protein array or microarray. The use of arrays to determine the presence and/or level of a collection of biological macromolecules is now well known (see, for example, methods described in published PCT application number WO 99/48916, describing hypoxia-related gene expression arrays). In array-based measurement methods, an array can be contacted with polynucleotides (in the case of a nucleic acid-based array) or polypeptides (in the case of a protein-based array) from a sample from a subject. The amount or position of binding of the subject's polynucleotides or polypeptides then can be determined, for instance to produce a gene expression profile for that subject. Such gene expression profile can be compared to another gene expression profile, for instance a control gene expression profile from a subject known to have suffered a stroke, or known to not have suffered a stroke. Such a method could be used to determine whether a subject had an ischemic stroke or determine the prognosis of a subject who had an ischemic stroke. In addition, the subject's gene expression profile can be correlated with one or more appropriate treatments, which can be correlated with a control (or set of control) expression profiles for levels of ischemia, for instance.

Example 14

Rapid Screening Assays

Prior to performing any assays to identify agents that alter the activity (such as the expression) of an ischemic stroke-related molecule, rapid screening assays can be used to screen a large number of agents to determine if they bind to an ischemic stroke-related protein.

Rapid screening assays for detecting binding to HIV proteins have been disclosed, for example in U.S. Pat. No. 5,230, 998, which is incorporated by reference. Briefly, an ischemic stroke-related protein (such as one or more of those listed in Tables 2-5) is incubated with a first antibody capable of binding to the protein, and incubated with one or more test agents. Excess unbound first antibody is washed and removed, and antibody bound to the ischemic stroke-related protein is detected by adding a second labeled antibody which binds the first antibody. Excess unbound second antibody is then removed, and the amount of detectable label is quantitated. The effect of the binding is then determined in percentages by the formula: (quantity of the label in the absence of the test agent)−(quantity of the label in the presence of the test agent/quantity of the label in the absence of the test agent)× 100.

Agents that have a high binding affinity to the ischemic stroke-related protein can then be used in other assays more specifically designed to determine the activity (such as the expression) of an ischemic stroke-related molecule.

Example 15

In Vitro Screening Assay

This example describes particular in vitro methods that can be used to screen test agents for their ability to alter the activity of an ischemic stroke-related molecule. However, the disclosure is not limited to these particular methods. One skilled in the art will appreciate that other in vitro assays could be used.

As disclosed in the Examples above, expression of the disclosed ischemic stroke-related molecules (such as those listed in Tables 2-5) is increased or decreased following an ischemic stroke. Therefore, screening assays can be used to identify and analyze agents that normalize such activity (such as decrease expression/activity of a gene that is increased following an ischemic stroke, increase expression/activity of a gene that is decreased following an ischemic stroke, or combinations thereof), or further enhance the change in activity (such as further decrease expression/activity of a gene that is decreased following an ischemic stroke, or further increase expression/activity of a gene that is increased following an ischemic stroke). For example, it may be desirable to further enhance the change in activity if such a change provides a beneficial effect to the subject or it may be desirable to neutralize the change in activity if such a change provides a harmful effect to the subject.

Agents identified via the disclosed assays can be useful, for example, in decreasing one or more symptoms associated with stroke, such as a decrease of at least about 10%, at least about 20%, at least about 50%, or even at least about 90%. Once identified, test agents found to alter the activity of an ischemic stroke-related molecule can be formulated in therapeutic products (or even prophylactic products) in pharmaceutically acceptable formulations, and used to treat a subject who has had an ischemic stroke.

Cells (such as at least 50,000 cells) that provide a model what happens in vivo following an ischemic stroke are cultured under hypoxic conditions, hypoglycemic conditions, or combinations thereof. For example, PBMCs can be cultured at 37° C. in hypoxic conditions of 94% $N_2$, 5% $CO_2$, and 1% $O_2$, for at least 1 hour, such as 4 hours or 24 hours. In another example, PBMCs are cultured at 37° C. in the absence of added glucose for at least 1 hour, such as 4 hours or 24 hours. In yet another example, PBMCs are cultured at 37° C. in at 94% $N_2$, 5% $CO_2$, and 1% $O_2$ in the absence of added glucose for at least 1 hour, such as 4 hours or 24 hours.

Simultaneous to incubation in the hypoxic or hypoglycemic conditions, or at a time later, one or more test agents are incubated with the cells under conditions sufficient for the test agent to have the desired effect on the cell, for example to alter (such as normalize) the activity of a ischemic stroke-related molecule. In one example, the agent is added at least 30 minutes after culturing the cells in the hypoxic or hypoglycemic conditions, such as at least 1 hour, at least 2 hours, at least 6 hours, or at least 24 hours after culturing the cells in the hypoxic or hypoglycemic conditions.

To determine the effect of the test agents on the activity of one or more ischemic stroke-related molecules, RNA can be isolated from the PBMCs and labeled (see Examples 1 and 2). The labeled RNA is exposed to an array containing one or more nucleic acid molecules (such as a primer or probe) that can specifically hybridize to one or more ischemic stroke-related genes, such at least 1, at least 2, or at least 3 of those listed in Tables 2-5 (for example using the methods described herein).

Alternatively, to determine the effect of the test agents on the activity of one or more ischemic stroke-related molecules, proteins are isolated from the PBMCs. The isolated proteins can be analyzed to detect differential expression of one or more ischemic stroke-related proteins, such at least 1, at least 2, or at least 3 of those listed in Tables 2-5, such as using the methods described in Example 9

Example 16

In Vivo Screening Assay

This example describes particular in vivo methods that can be used to screen test agents for their ability to alter the activity of an ischemic stroke-related molecule. However, the disclosure is not limited to these particular methods. One skilled in the art will appreciate that other in vivo assays could be used (such as other mammals or other means of inducing an ischemic stroke).

A mammal is exposed to conditions that induce an ischemic stroke. In a particular example, an ischemic stroke is induced in a mouse by occlusion of the middle cerebral artery (MCA) under anesthesia (for example 1 mL/kg of a mixture of ketamine (75 mg/mL) and xylazine (5 mg/mL)). The mouse is anesthetized and a U-shape incision made between the left ear and left eye. The top and back segments of the temporal muscle are transected, and the skull exposed by retraction of the temporal muscle. A small opening (1 to 2 mm in diameter) is made in the region over the MCA with saline superfusion to prevent heat injury. The meninges can be removed, and the MCA occluded by ligation, for example with 10-0 nylon thread (Ethylon). Occlusion of the MCA can be persistent (for example by transecting the MCA distally to the ligation point), or reversible, for example by occluding for a finite period of time, such as at least 10 minutes, at least 30 minutes, or at least 60 minutes. Alternatively or in addition, the mouse is exposed hypoxic conditions, such as 8-11% oxygen for 2 hours.

Simultaneous to inducing the ischemic stroke, or at a time later, one or more test agents are administered to the subject under conditions sufficient for the test agent to have the desired effect on the subject. Any appropriate method of administration can be used, such as intravenous, intramuscular, or transdermal. In one example, the agent is added at least 30 minutes after the ischemic stroke, such as at least 1 hour, at least 2 hours, at least 6 hours, or at least 24 hours after the ischemic stroke.

The effect of the test agents on the activity of one or more ischemic stroke-related molecules can be determined using methods described in Example 15. For example, PBMCs can be isolated from the subject following exposure to the test agent. RNA or proteins isolated from the PBMCs can be analyzed to determine the activity of one or more ischemic stroke-related molecules.

Example 17

Assays for Determining Effective Dose and Effect on Ischemic Stroke

This example describes methods that can be used to further evaluate test agents that alter the activity of an ischemic stroke-related molecule, such as those identified using the methods described in Examples 15 and 16. For example, effective doses of the test agents, and the ability of the agent to treat an ischemic stroke can be determined in vitro or in vivo.

Cell-Based Assays

Cells (such as 20,000 to 500,000 cells) are exposed to conditions that mimic an ischemic stroke, such as hypoxic or hypoglycemic conditions (or both), and the incubation continued for at least 1 hour (such as at least 4 hours or at least 24 hours). The test agent can be applied to the cells before, during, or after mimicking an ischemic stroke. In some examples, several different doses of the potential therapeutic agent are administered, to identify optimal dose ranges. For example, milligram, microgram, and nanogram concentrations can be used. Subsequently, assays are conducted to determine the activity of one or more ischemic stroke-related molecules.

Animal Model Assays

The ability of an agent, such as those identified using the methods provide above, to treat an ischemic stroke, can be assessed in animal models. Several methods of inducing an ischemic stroke in a mammal are known, and particular examples are provided herein. Mammals of any species, including, but not limited to, mice, rats, rabbits, dogs, guinea pigs, pigs, micro-pigs, goats, and non-human primates, such as baboons, monkeys, and chimpanzees, can be used to generate an animal model of ischemic stroke. Such animal models can also be used to test agents for an ability to ameliorate symptoms associated with ischemic stroke. In addition, such animal models can be used to determine the LD50 and the ED50 in animal subjects, and such data can be used to determine the in vivo efficacy of potential agents.

An ischemic stroke is induced in the mammal, and one or more test agents identified in the examples above administered. The amount of test agent administered can be determined by skilled practitioners. In some examples, several different doses of the potential therapeutic agent can be administered to different test subjects, to identify optimal dose ranges. The therapeutic agent can be administered before, during, or after inducing the ischemic stroke. Subsequent to the treatment, animals are observed for one or more symptoms associated with ischemic stroke. A decrease in the development of symptoms associated with ischemic stroke in the presence of the test agent provides evidence that the test agent is a therapeutic agent that can be used to decrease or even inhibit ischemic stroke in a subject.

Example 18

Differential Expression Associated with Ischemic Stroke

This example describes particular changes in expression, such as gene or protein expression, that are associated with ischemic stroke. Although particular ischemic stroke-related molecules are listed in this example, one skilled in the art will appreciated that other molecules can be used based on the teachings in this disclosure.

In particular examples detecting differential expression includes detecting differences in expression (such as an increase, decrease, or both). The method can further include determining the magnitude of the difference in expression, wherein the magnitude of the change is associated with ischemic stroke. Particular examples of ischemic stroke-related molecules that are differentially expressed in association with the diagnosis of an ischemic stroke, and their direction of change (upregulated or downregulated), and the magnitude of the change (as expressed as a percent, t-statistic, and fold change) are provided in Table 10.

TABLE 10

Exemplary patterns of expression associated with ischemic stroke

| Ischemic Stroke Molecule | Change in Expression | Magnitude of the change |
|---|---|---|
| CD163 | Upregulated | t-statistic of at least 7 (such as at least 7.8) at least 50% at least 4-fold |
| hypothetical protein FLJ22662 Laminin A motif | upregulated | t-statistic of at least 7.5 (such as at least 7.8) at least 50% at least 4-fold |
| BST-1 | upregulated | t-statistic of at least 6 (such as at least 6.4) at least 50% at least 4-fold |
| FcγRI | upregulated | t-statistic of at least 4.5 (such as at least 5.7) at least 50% at least 4-fold |
| baculoviral IAP repeat-containing protein 1 | upregulated | t-statistic of at least 4 (such as at least 4.4) at least 50% at least 4-fold |
| KIAA0146 | upregulated | t-statistic of at least 5 (such as at least 6.5) at least 50% at least 4-fold |
| intercellular adhesion molecule 2 | downregulated | t-statistic of no more than −5.0 (such as no more than −5.4) at least 50% at least 4-fold |
| protein kinase D2 | downregulated | t-statistic of no more than −5.0 (such as no more than −5.5) at least 50% at least 4-fold |
| GATA binding protein 3 | downregulated | t-statistic of no more than −5.5 (such as no more than −5.9) at least 50% at least 4-fold |
| hypothetical protein FLJ20257 | downregulated | t-statistic of no more than −5.5 (such as no more than −5.9) at least 50% at least 4-fold |
| protein kinase C, theta | downregulated | t-statistic of no more than −6 (such as no more than −6.1) at least 50% at least 4-fold |

Therefore, CD163; hypothetical protein FLJ22662 Laminin A motif; BST-1; FcγRI; baculoviral IAP repeat-containing protein 1; and KIAA0146 are upregulated by a magnitude of at least 50%, at least 4-fold or have a t-statistic of at least 4. That is, CD163; hypothetical protein FLJ22662 Laminin A motif; BST-1; FcγRI; baculoviral IAP repeat-containing protein 1; and KIAA0146 are upregulated by an amount associated with ischemic stroke, for example at least 50% or at least 4-fold (or have a t-statistic of at least 4). In addition, intercellular adhesion molecule 2, protein kinase D2, GATA binding protein 3, hypothetical protein FLJ20257, and protein kinase C, theta are downregulated by a magnitude of at least 50%, at least 4-fold or have a t-statistic of no more than −5. That is, intercellular adhesion molecule 2, protein kinase D2, GATA binding protein 3, hypothetical protein FLJ20257, and protein kinase C, theta are downregulated by an amount associated with ischemic stroke, for example at least 50% or at least 4-fold (or have a t-statistic of no more than −5).

One example of a pattern of expression of proteins that have been found to be associated with ischemic stroke, such as upregulation of CD163; hypothetical protein FLJ22662 Laminin A motif; and BST-1, wherein the magnitude of change is at least 4-fold for each of CD163; hypothetical protein FLJ22662 Laminin A motif; and BST-1. Another example of a pattern of expression of proteins that have been found to be associated with ischemic stroke is as upregulation of CD163; hypothetical protein FLJ22662 Laminin A motif; BST-1; FcγRI; baculoviral IAP repeat-containing protein 1; and KIAA0146, for example wherein the magnitude of change is at least 4-fold for each of these proteins.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

---

We claim:

1. A method of determining whether a human subject has had an ischemic stroke, comprising:

detecting expression of ischemic stroke-related nucleic acid molecules of the subject obtained from a blood sample, wherein the ischemic stroke-related molecules comprise CD163 detectable by using any of SEQ ID NOS: 21-42; hypothetical protein FLJ22662 laminin A motif detectable by using any of SEQ ID NOS: 43-53; amyloid beta (A4) precursor-like protein 2 detectable by using any of SEQ ID NOS: 54-86; N-acetylneuraminate pyruvate lyase detectable by using any of SEQ ID NOS: 87-97; v-fos FBJ murine osteosarcoma viral oncogene homolog detectable by using any of SEQ ID NOS: 98-108; toll-like receptor 2 detectable by using any of SEQ ID NOS: 109-119; chondroitin sulfate proteoglycan 2 (versican) detectable by using any of SEQ ID NOS: 120-174; interleukin 13 receptor, alpha 1 detectable by using any of SEQ ID NOS: 175-218; CD14 antigen detectable by using any of SEQ ID NOS: 219-229; bone marrow stromal cell antigen 1/CD157 detectable by using any of SEQ ID NOS: 230-240; complement component 1, q subcomponent, receptor 1 detectable by using any of SEQ ID NOS: 241-262; paired immunoglobin-like type 2 receptor alpha detectable by using any of SEQ ID NOS: 263-284; Fc fragment of IgG, high affinity Ia, receptor for (CD64) detectable by using any of SEQ ID NOS: 285-295; ectonucleoside triphosphate diphosphohydrolase 1 detectable by using any of SEQ ID NOS: 296-328; CD36 antigen (collagen type I receptor, thrombospondin receptor) detectable by using any of SEQ ID NOS: 329-350; adrenomedullin detectable by using any of SEQ ID NOS: 351-361; dual specificity phosphatase 1 detectable by using any of SEQ ID NOS: 362-383; cytochrome b-245, beta polypeptide (chronic granulomatous disease) detectable by using any of SEQ ID NOS: 384-394; leukotriene A4 hydrolase detectable by using any of SEQ ID NOS: 395-405; erythroblastosis virus E26 oncogene homolog 2 (avian) detectable by using any of SEQ ID NOS: 406-427; neuronal apoptosis inhibitory protein: *Homo sapiens* transcribed sequence with strong similarity to protein sp:Q13075 (*H. sapiens*) BIR1_HUMAN Baculoviral IAP repeat-containing protein 1 detectable by using any of SEQ ID NOS: 428-438; and KIAA0146 protein detectable by using any of SEQ ID NOS: 439-460;

comparing expression of the ischemic stroke-related nucleic acid molecules to a control representing expression of the ischemic stroke-related nucleic acid molecules expected in a subject who has not had an ischemic stroke; and determining that the subject has had an ischemic stroke when the presence of an at least 4-fold increase in expression of the ischemic stroke-related nucleic acid molecules in the subject relative to the control is detected.

2. The method of claim 1, wherein expression of ischemic stroke-related nucleic acid molecules is detected within 24 hours of onset of clinical signs and symptoms that indicate a potential stroke.

3. The method of claim 1, wherein expression of ischemic stroke-related nucleic acid molecules is detected within 7-14 days of onset of clinical signs and symptoms that indicate a potential stroke.

4. The method of claim 1, wherein expression of ischemic stroke-related nucleic acid molecules is detected within 90 days of onset of clinical signs and symptoms that indicate a potential stroke.

5. The method of claim 1, wherein the method has a sensitivity of at least 78% and accuracy of at least 80% for determining that the subject has had an ischemic stroke.

6. The method of claim 1, wherein the subject had an onset of clinical signs and symptoms of an ischemic stroke no more than 72 hours prior to detecting expression of the ischemic stroke-related molecules.

7. The method of claim 1, wherein the nucleic acid molecules are isolated from the blood sample, thereby generating isolated nucleic acid molecules, and wherein the isolated nucleic acid molecules are hybridized with oligonucleotides that detect the ischemic stroke-related molecules.

8. The method of claim 7, wherein the nucleic acid molecules isolated from the blood sample are obtained from peripheral blood mononuclear cells (PBMCs).

9. A method of determining whether a human subject has had an ischemic stroke, comprising:

applying isolated nucleic acid molecules obtained from PBMCs of the subject to an array, wherein the array consists of oligonucleotides complementary to ischemic stroke-related nucleic acid molecules consisting of CD163 detectable by using any of SEQ ID NOS: 21-42; hypothetical protein FLJ22662 laminin A motif detectable by using any of SEQ ID NOS: 43-53; amyloid beta (A4) precursor-like protein 2 detectable by using any of SEQ ID NOS: 54-86; N-acetylneuraminate pyruvate lyase detectable by using any of SEQ ID NOS: 87-97; v-fos FBJ murine osteosarcoma viral oncogene homolog detectable by using any of SEQ ID NOS: 98-108; toll-like receptor 2 detectable by using any of SEQ ID NOS: 109-119; chondroitin sulfate proteoglycan 2 (versican) detectable by using any of SEQ ID NOS: 120-174; interleukin 13 receptor, alpha 1 detectable by using any of SEQ ID NOS: 175-218; CD14 antigen detectable by using any of SEQ ID NOS: 219-229; bone marrow stromal cell antigen 1/CD157 detectable by using any of SEQ ID NOS: 230-240; complement component 1, q subcomponent, receptor 1 detectable by using any of SEQ ID NOS: 241-262; paired immunoglobin-like type 2 receptor alpha detectable by using any of SEQ ID NOS: 263-284; Fc fragment of IgG, high affinity Ia, receptor for (CD64) detectable by using any of SEQ ID NOS: 285-295; ectonucleoside triphosphate diphosphohydrolase 1 detectable by using any of SEQ ID NOS: 296-328; CD36 antigen (collagen type I receptor, thrombospondin receptor) detectable by using any of SEQ ID NOS: 329-350; adrenomedullin detectable by using any of SEQ ID NOS: 351-361; dual specificity phosphatase 1 detectable by using any of SEQ ID NOS: 362-383; cytochrome b-245, beta polypeptide (chronic granulomatous disease) detectable by using any of SEQ ID NOS: 384-394; leukotriene A4 hydrolase detectable by using any of SEQ ID NOS: 395-405; erythroblastosis virus E26 oncogene homolog 2 (avian) detectable by using any of SEQ ID NOS: 406-427; neuronal apoptosis inhibitory protein: *Homo sapiens* transcribed sequence with strong similarity to protein sp:Q13075 (*H. sapiens*) BIR1_HUMAN Baculoviral IAP repeat-containing protein 1 detectable by using any of SEQ ID NOS: 428-438; and KIAA0146 protein detectable by using any of SEQ ID NOS: 439-460;

incubating the isolated nucleic acid molecules with the array for a time sufficient to allow hybridization between the isolated nucleic acid molecules and oligonucleotide probes, thereby forming isolated nucleic acid molecule: oligonucleotide complexes;

comparing expression of the ischemic stroke-related nucleic acid molecules to a control representing expression of the ischemic stroke-related nucleic acid molecules expected in a subject who has not had an ischemic stroke, and determining that the subject has had an ischemic stroke when the presence of an at least 4-fold increase in expression of all the ischemic stroke-related nucleic acid molecules in the subject relative to the control is detected.

10. The method of claim 1, further comprising administering to the subject a treatment to avoid or reduce ischemic injury if the presence of increased expression indicates that the subject has had an ischemic stroke.

11. The method of claim 1, wherein detecting expression comprises quantitating expression of the ischemic stroke-related nucleic acid molecules.

* * * * *

SEQUENCE LISTING

```
<160> NUMBER OF SEQ ID NOS: 460

<210> SEQ ID NO 1
<211> LENGTH: 23
<212> TYPE: DNA
<213> ORGANISM: Artificial Sequence
<220> FEATURE:
<223> OTHER INFORMATION: real time pcr primer

<400> SEQUENCE: 1
cgaaagaagt ggaataagtg ggc                                          23

<210> SEQ ID NO 2
<211> LENGTH: 18
<212> TYPE: DNA
<213> ORGANISM: Artificial Sequence
<220> FEATURE:
<223> OTHER INFORMATION: real time pcr primer

<400> SEQUENCE: 2
ccgcagttcc ctcttccc                                                18

<210> SEQ ID NO 3
<211> LENGTH: 21
<212> TYPE: DNA
<213> ORGANISM: Artificial Sequence
<220> FEATURE:
<223> OTHER INFORMATION: real time pcr primer

<400> SEQUENCE: 3
caaggtactg agcattgccc a                                            21

<210> SEQ ID NO 4
<211> LENGTH: 19
<212> TYPE: DNA
<213> ORGANISM: Artificial Sequence
<220> FEATURE:
<223> OTHER INFORMATION: real time pcr primer

<400> SEQUENCE: 4
tgttcgcagg aaaaggcag                                               19

<210> SEQ ID NO 5
<211> LENGTH: 21
<212> TYPE: DNA
<213> ORGANISM: Artificial Sequence
<220> FEATURE:
<223> OTHER INFORMATION: real time pcr primer
```

```
<400> SEQUENCE: 5
gatgcagcct catttccacc t                                              21

<210> SEQ ID NO 6
<211> LENGTH: 20
<212> TYPE: DNA
<213> ORGANISM: Artificial Sequence
<220> FEATURE:
<223> OTHER INFORMATION: real time pcr primer

<400> SEQUENCE: 6
aggccttgga tggaagaaca                                                20

<210> SEQ ID NO 7
<211> LENGTH: 22
<212> TYPE: DNA
<213> ORGANISM: Artificial Sequence
<220> FEATURE:
<223> OTHER INFORMATION: real time pcr primer

<400> SEQUENCE: 7
gacccgagct ttgattgact cc                                             22

<210> SEQ ID NO 8
<211> LENGTH: 22
<212> TYPE: DNA
<213> ORGANISM: Artificial Sequence
<220> FEATURE:
<223> OTHER INFORMATION: real time pcr primer

<400> SEQUENCE: 8
ttgatctgct gagagtccca gc                                             22

<210> SEQ ID NO 9
<211> LENGTH: 21
<212> TYPE: DNA
<213> ORGANISM: Artificial Sequence
<220> FEATURE:
<223> OTHER INFORMATION: real time pcr primer

<400> SEQUENCE: 9
gatgaccgtc gtgagcgaat t                                              21

<210> SEQ ID NO 10
<211> LENGTH: 19
<212> TYPE: DNA
<213> ORGANISM: Artificial Sequence
<220> FEATURE:
<223> OTHER INFORMATION: real time pcr primer

<400> SEQUENCE: 10
ttacgtccag cattgccca                                                 19

<210> SEQ ID NO 11
<211> LENGTH: 21
<212> TYPE: DNA
<213> ORGANISM: Artificial Sequence
<220> FEATURE:
<223> OTHER INFORMATION: real time pcr primer

<400> SEQUENCE: 11
gactgtgctt tccgaatggc t                                              21

<210> SEQ ID NO 12
```

```
<211> LENGTH: 22
<212> TYPE: DNA
<213> ORGANISM: Artificial Sequence
<220> FEATURE:
<223> OTHER INFORMATION: real time pcr primer

<400> SEQUENCE: 12
tgaccttgac cagaggcttg tc                                              22

<210> SEQ ID NO 13
<211> LENGTH: 22
<212> TYPE: DNA
<213> ORGANISM: Artificial Sequence
<220> FEATURE:
<223> OTHER INFORMATION: real time pcr primer

<400> SEQUENCE: 13
agatggcgtg ttagcagtcc ct                                              22

<210> SEQ ID NO 14
<211> LENGTH: 20
<212> TYPE: DNA
<213> ORGANISM: Artificial Sequence
<220> FEATURE:
<223> OTHER INFORMATION: real time pcr primer

<400> SEQUENCE: 14
gccattgtgg aaccatttgg                                                 20

<210> SEQ ID NO 15
<211> LENGTH: 19
<212> TYPE: DNA
<213> ORGANISM: Artificial Sequence
<220> FEATURE:
<223> OTHER INFORMATION: real time pcr primer

<400> SEQUENCE: 15
ctggctggtt gccaactcc                                                  19

<210> SEQ ID NO 16
<211> LENGTH: 21
<212> TYPE: DNA
<213> ORGANISM: Artificial Sequence
<220> FEATURE:
<223> OTHER INFORMATION: real time pcr primer

<400> SEQUENCE: 16
aaagaagcca ttgtcacccc a                                               21

<210> SEQ ID NO 17
<211> LENGTH: 20
<212> TYPE: DNA
<213> ORGANISM: Artificial Sequence
<220> FEATURE:
<223> OTHER INFORMATION: real time pcr primer

<400> SEQUENCE: 17
tcggcgttct ctcaggtgac                                                 20

<210> SEQ ID NO 18
<211> LENGTH: 21
<212> TYPE: DNA
<213> ORGANISM: Artificial Sequence
<220> FEATURE:
<223> OTHER INFORMATION: real time pcr primer

<400> SEQUENCE: 18
```

```
tgcaacacca aacactggga g                                              21

<210> SEQ ID NO 19
<211> LENGTH: 23
<212> TYPE: DNA
<213> ORGANISM: Artificial Sequence
<220> FEATURE:
<223> OTHER INFORMATION: real time pcr primer

<400> SEQUENCE: 19
agaatttgct gtatgccgag atg                                            23

<210> SEQ ID NO 20
<211> LENGTH: 25
<212> TYPE: DNA
<213> ORGANISM: Artificial Sequence
<220> FEATURE:
<223> OTHER INFORMATION: real time PCR primer

<400> SEQUENCE: 20
tgatatccag tttaggtggt ccaat                                          25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 21
cgtcagtcat cctttattgc agtcg                                          25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 22
tattgcagtc gggatccttg gggtt                                          25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 23
ggccattttc gtcgcattat tcttc                                          25

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 24
cagagacagc ggcttgcagt ttcct                                          25

<210> SEQ ID NO 25
<211> LENGTH: 25
<212> TYPE: DNA
```

-continued

```
<213> ORGANISM: Artificial Sequence
<220> FEATURE:
<223> OTHER INFORMATION: Synthetic oligonucleotide probe

<400> SEQUENCE: 25
aattcccatg agtcagctga tttca                                              25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 26
aaaggaggcc attctgagcc acact                                              25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 27
ataacccagt gagttcagcc tttaa                                              25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 28
tggagcagaa attcacctct ctcac                                              25

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 29
tcacctctct cactgactat tacag                                              25

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 30
ggagttcttc ttctcctagg attcc                                              25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 31
ctaggattcc taagactgct gctga                                              25
```

<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 32
gccagacgct ggggccatag tgagt                                  25

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 33
cgtcagtcat cctttattgc agtcg                                  25

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 34
tattgcagtc gggatccttg gggtt                                  25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 35
ggccattttc gtcgcattat tcttc                                  25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 36
cagagacagc ggcttgcagt ttcct                                  25

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 37
ttagtccacc aaattcaata ccggg                                  25

<210> SEQ ID NO 38
<211> LENGTH: 25
<212> TYPE: DNA
<213> ORGANISM: Artificial Sequence
<220> FEATURE:

-continued

<223> OTHER INFORMATION: Synthetic oligonucleotide probe

<400> SEQUENCE: 38
taccgggaga tgaattcttg cctga                                          25

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 39
gccattctga gccacactga aaagg                                          25

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 40
ataacccagt gagttcagcc tttaa                                          25

<210> SEQ ID NO 41
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 41
tggagcagaa attcacctct ctcac                                          25

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 42
ggagttcttc ttctcctagg attcc                                          25

<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 43
gtggctatcc actgttagtt cagaa                                          25

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 44
ctgggcttgg actactctta tgatt                                          25

```
<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 45
agctccacga gccaaaattt tccgg                                              25

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 46
agaggtgacc cctgtaatac catct                                              25

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 47
gctgccgtga ggacctgaac tcacc                                              25

<210> SEQ ID NO 48
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 48
ctcacctaac ccaagtcctg gaggt                                              25

<210> SEQ ID NO 49
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 49
gtggcagata tctacctagc atctc                                              25

<210> SEQ ID NO 50
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 50
ctagcatctc agtacacatc ctatg                                              25

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide probe
```

<400> SEQUENCE: 51
atcctatgcc ataagtggtc ccaca                                              25

<210> SEQ ID NO 52
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 52
ggcatgccag aggtctacaa ctttg                                              25

<210> SEQ ID NO 53
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 53
ttagctatgt ttttcccatc agaat                                              25

<210> SEQ ID NO 54
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 54
cccactgcgg gaggacttca gtctg                                              25

<210> SEQ ID NO 55
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 55
ggaggacttc agtctgagta gcagt                                              25

<210> SEQ ID NO 56
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 56
gagggatgca ggtgggccgg aagat                                              25

<210> SEQ ID NO 57
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 57
gtgggccgga agatcccacg attcc                                              25

<210> SEQ ID NO 58
<211> LENGTH: 25

```
<212> TYPE: DNA
<213> ORGANISM: Artificial Sequence
<220> FEATURE:
<223> OTHER INFORMATION: Synthetic oligonucleotide probe

<400> SEQUENCE: 58
cggaagatcc cacgattccg atcga                                          25

<210> SEQ ID NO 59
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 59
tccgatcgac tgccaagcag cagcc                                          25

<210> SEQ ID NO 60
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 60
atcctgacct cctggactgt aggac                                          25

<210> SEQ ID NO 61
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 61
gacctcctgg actgtaggac tatat                                          25

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 62
taggactata taaagtacta ctgta                                          25

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 63
gtactactgt agaactgcaa tttcc                                          25

<210> SEQ ID NO 64
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 64
```
tgtagaactg caatttccat tcttt                                              25

<210> SEQ ID NO 65
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 65
gtagcagtgc tctcattggc ctgct                                              25

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 66
atcgcagtgg ccattgccac ggtca                                              25

<210> SEQ ID NO 67
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 67
gaggcagtat ggcaccatca gccac                                              25

<210> SEQ ID NO 68
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 68
tggaggttga tccaatgctc acccc                                              25

<210> SEQ ID NO 69
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 69
gaaccatggc tatgagaacc ccacc                                              25

<210> SEQ ID NO 70
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 70
accccaccta caaatacctg gagca                                              25

<210> SEQ ID NO 71
<211> LENGTH: 25
<212> TYPE: DNA
<213> ORGANISM: Artificial Sequence

```
<220> FEATURE:
<223> OTHER INFORMATION: Synthetic oligonucleotide probe

<400> SEQUENCE: 71
ttaggtggca gggagcgcgg cagcc                                          25

<210> SEQ ID NO 72
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 72
tccgatcgac tgccaagcag cagcc                                          25

<210> SEQ ID NO 73
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 73
atcctgacct cctggactgt aggac                                          25

<210> SEQ ID NO 74
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 74
attaatcaga aaccccactt ccatt                                          25

<210> SEQ ID NO 75
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 75
gtattgtctg acacatgctc tcaat                                          25

<210> SEQ ID NO 76
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 76
gcaggatggg ggactgatcg gtgcc                                          25

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 77
ggaagagcgg gaatccgtgg gccca                                          25
```

<210> SEQ ID NO 78
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 78
tggtcatcgc agtggccatt gccac                                    25

<210> SEQ ID NO 79
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 79
gtcatcgtca tcagcctggt gatgc                                    25

<210> SEQ ID NO 80
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 80
gaggcagtat ggcaccatca gccac                                    25

<210> SEQ ID NO 81
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 81
tggaggttga tccaatgctc acccc                                    25

<210> SEQ ID NO 82
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 82
gaaccatggc tatgagaacc ccacc                                    25

<210> SEQ ID NO 83
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 83
accccaccta caaatacctg gagca                                    25

<210> SEQ ID NO 84
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 84
ttaggtggca gggagcgcgg cagcc					25

<210> SEQ ID NO 85
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 85
ggcggaggga tgcagatgtg caggc					25

<210> SEQ ID NO 86
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 86
tcctctctgg actttctcca aaggc					25

<210> SEQ ID NO 87
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 87
tggaagctgg tagctagtgc ctctc					25

<210> SEQ ID NO 88
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 88
agtgcctctc tatcaaatca gggtt					25

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 89
atcagggttt gcaccttgag acata					25

<210> SEQ ID NO 90
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 90
ttgaggtacc ttttgtgagc cttaa					25

<210> SEQ ID NO 91

<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 91
acaactctca gtcattcatt tcaca                                          25

<210> SEQ ID NO 92
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 92
ccatctgtct ttaggagctc tcatt                                          25

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 93
ttaggagctc tcattatctc ggtct                                          25

<210> SEQ ID NO 94
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 94
aaactctgag ctactgcatt taggc                                          25

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 95
gcatttaggc aggcacttta atacc                                          25

<210> SEQ ID NO 96
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 96
gtaacatgtc tcaactgtat acaac                                          25

<210> SEQ ID NO 97
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 97
acaccagctc atttggctgc tcagt                                              25

<210> SEQ ID NO 98
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 98
ctgcccgagc tggtgcatta cagag                                              25

<210> SEQ ID NO 99
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 99
gagaaacaca tcttccctag agggt                                              25

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 100
gagggttcct gtagacctag ggagg                                              25

<210> SEQ ID NO 101
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 101
aggaccttat ctgtgcgtga aacac                                              25

<210> SEQ ID NO 102
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 102
gtgaaacaca ccaggctgtg ggcct                                              25

<210> SEQ ID NO 103
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 103
gtgtggactc aagtccttac ctctt                                              25

<210> SEQ ID NO 104
<211> LENGTH: 25
<212> TYPE: DNA

```
<213> ORGANISM: Artificial Sequence
<220> FEATURE:
<223> OTHER INFORMATION: Synthetic oligonucleotide probe

<400> SEQUENCE: 104
tccttacctc ttccggagat gtagc                                            25

<210> SEQ ID NO 105
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 105
tgtattgttc ccagtgacac ttcag                                            25

<210> SEQ ID NO 106
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 106
ttagtagcat gttgagccag gcctg                                            25

<210> SEQ ID NO 107
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 107
tctccttagt cttctcatag catta                                            25

<210> SEQ ID NO 108
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 108
gtgttcctgg caatagtgtg ttctg                                            25

<210> SEQ ID NO 109
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 109
gtttcttaca gtgagcggga tgcct                                            25

<210> SEQ ID NO 110
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 110
gagaacctta tggtccagga gctgg                                            25
```

<210> SEQ ID NO 111
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 111
ataagcggga cttcattcct ggcaa                                    25

<210> SEQ ID NO 112
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 112
gtatgaactg gacttctccc atttc                                    25

<210> SEQ ID NO 113
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 113
ctcccatttc cgtctttttg aagag                                    25

<210> SEQ ID NO 114
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 114
aatgatgctg ccattctcat tcttc                                    25

<210> SEQ ID NO 115
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 115
agcgcttctg caagctgcgg aagat                                    25

<210> SEQ ID NO 116
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 116
acaccaagac ctacctggag tggcc                                    25

<210> SEQ ID NO 117
<211> LENGTH: 25
<212> TYPE: DNA
<213> ORGANISM: Artificial Sequence
<220> FEATURE:

<223> OTHER INFORMATION: Synthetic oligonucleotide probe

<400> SEQUENCE: 117
tggagtggcc catggacgag gctca    25

<210> SEQ ID NO 118
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 118
agctgcgata aagtcctagg ttccc    25

<210> SEQ ID NO 119
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 119
gaccagtctt tgtctagttg ggatc    25

<210> SEQ ID NO 120
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 120
tgccgtgctc ccaaaacatt ttaaa    25

<210> SEQ ID NO 121
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 121
gcatttccag cctatctaat ttctt    25

<210> SEQ ID NO 122
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 122
tagttttcta tttgcctcca gtgca    25

<210> SEQ ID NO 123
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 123
gtataccagc ctactgtact attta    25

```
<210> SEQ ID NO 124
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 124
tttcagcacc gatggccatg taaat                                        25

<210> SEQ ID NO 125
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 125
ggagccttag aggtctttaa tcatt                                        25

<210> SEQ ID NO 126
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 126
ggctgctttt atgtagttta ggctg                                        25

<210> SEQ ID NO 127
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 127
ggctggaaat ggtttcactt gctct                                        25

<210> SEQ ID NO 128
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 128
ggtgcagttt gcttctacat gatgc                                        25

<210> SEQ ID NO 129
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 129
aaggctgcga atgggatcct gatgg                                        25

<210> SEQ ID NO 130
<211> LENGTH: 25
<212> TYPE: DNA
<213> ORGANISM: Artificial Sequence
<220> FEATURE:
<223> OTHER INFORMATION: Synthetic oligonucleotide probe
```

```
<400> SEQUENCE: 130
ccaatgtcga actcttcttt gctgc                                              25

<210> SEQ ID NO 131
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 131
tttcagcacc gatggccatg taaat                                              25

<210> SEQ ID NO 132
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 132
gaaatggttt cacttgctct ttgac                                              25

<210> SEQ ID NO 133
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 133
gaagatggct tttcctggac agcta                                              25

<210> SEQ ID NO 134
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 134
tgtaggtcat tgcacctatc tcagc                                              25

<210> SEQ ID NO 135
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 135
ggtgcagttt gcttctacat gatgc                                              25

<210> SEQ ID NO 136
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 136
ggctgcgaat gggatcctga tggaa                                              25

<210> SEQ ID NO 137
<211> LENGTH: 25
```

```
<212> TYPE: DNA
<213> ORGANISM: Artificial Sequence
<220> FEATURE:
<223> OTHER INFORMATION: Synthetic oligonucleotide probe

<400> SEQUENCE: 137
ccaatgtcga actcttcttt gctgc                                         25

<210> SEQ ID NO 138
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 138
cattcctttt tcttcactta caaga                                         25

<210> SEQ ID NO 139
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 139
ggtctacttt ttaatggctt tcata                                         25

<210> SEQ ID NO 140
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 140
aaggttaccg atcaatgcat ttcat                                         25

<210> SEQ ID NO 141
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 141
agacctaggg ctctggaggg tgggg                                         25

<210> SEQ ID NO 142
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 142
tctcacctat acgtgcaaga aagga                                         25

<210> SEQ ID NO 143
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 143
```

-continued

| | |
|---|---|
| gaaaatgcca agacctttgg aaaga | 25 |

<210> SEQ ID NO 144
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 144

| | |
|---|---|
| ggaaagatga aacctcgtta tgaaa | 25 |

<210> SEQ ID NO 145
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 145

| | |
|---|---|
| aacctcgtta tgaaatcaac tccct | 25 |

<210> SEQ ID NO 146
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 146

| | |
|---|---|
| gatggtttca ttcaacgtca ccttc | 25 |

<210> SEQ ID NO 147
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 147

| | |
|---|---|
| tcaccttcca actatccggt gctta | 25 |

<210> SEQ ID NO 148
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 148

| | |
|---|---|
| ccttccaact atccggtgct tagga | 25 |

<210> SEQ ID NO 149
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 149

| | |
|---|---|
| tccaactatc cggtgcttag gaaat | 25 |

<210> SEQ ID NO 150
<211> LENGTH: 25
<212> TYPE: DNA
<213> ORGANISM: Artificial Sequence

```
<220> FEATURE:
<223> OTHER INFORMATION: Synthetic oligonucleotide probe

<400> SEQUENCE: 150
ggaaatggaa gatgggctat accta                                  25

<210> SEQ ID NO 151
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 151
gatgggctat acctaaaatt acctg                                  25

<210> SEQ ID NO 152
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 152
atacctaaaa ttacctgcat gaacc                                  25

<210> SEQ ID NO 153
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 153
acaagcatcc tgtctcacga agaac                                  25

<210> SEQ ID NO 154
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 154
tgtttgttaa tcgtgtgggc catga                                  25

<210> SEQ ID NO 155
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 155
atcagtggat aggcctcaat gacaa                                  25

<210> SEQ ID NO 156
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 156
atgtttgagc atgacttccg ttgga                                  25
```

<210> SEQ ID NO 157
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 157
atgacttccg ttggactgat ggcag                                    25

<210> SEQ ID NO 158
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 158
gatggcagca cactgcaata cgaga                                    25

<210> SEQ ID NO 159
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 159
gagaattgga gacccaacca gccag                                    25

<210> SEQ ID NO 160
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 160
cagccagaca gcttcttttc tgctg                                    25

<210> SEQ ID NO 161
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 161
gactgtgttg taatcatttg gcatg                                    25

<210> SEQ ID NO 162
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 162
ctgcatgaac ccatctgcat accaa                                    25

<210> SEQ ID NO 163
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 163
tgatcatcgt tggagccgga ggtgg                                    25

<210> SEQ ID NO 164
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 164
agtgtatgtg ttgacatttc tcccc                                    25

<210> SEQ ID NO 165
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 165
ttttctcccc attatttgaa taaag                                    25

<210> SEQ ID NO 166
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 166
tccttcccta atttcagttt agagc                                    25

<210> SEQ ID NO 167
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 167
ggcacaaagg gattggccca atatt                                    25

<210> SEQ ID NO 168
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 168
atgactctag ctacaataat acaca                                    25

<210> SEQ ID NO 169
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 169
taagcaggtt cccttggttg ttgca                                    25

<210> SEQ ID NO 170

```
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 170
taaatgtaat ccacctttag gtatt                                          25

<210> SEQ ID NO 171
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 171
tgatctagta ggtttctatt tttcc                                          25

<210> SEQ ID NO 172
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 172
acaatgcaca taatactttc ctgta                                          25

<210> SEQ ID NO 173
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 173
actttcctgt atttatatca taacg                                          25

<210> SEQ ID NO 174
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 174
tttatatctg cttttgtttc accaa                                          25

<210> SEQ ID NO 175
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 175
taagaagcgc aattccacac tctac                                          25

<210> SEQ ID NO 176
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 176
```

-continued gttactcatt gttccagtca tcgtc                                              25

<210> SEQ ID NO 177
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 177
atcatagtac tcctgcttta cctaa                                              25

<210> SEQ ID NO 178
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 178
gattattata ttccctccaa ttcct                                              25

<210> SEQ ID NO 179
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 179
tccaattcct gatcctggca agatt                                              25

<210> SEQ ID NO 180
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 180
gaatgatgat actctgcact ggaag                                              25

<210> SEQ ID NO 181
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 181
ggaaaccgac tctgtagtgc tgata                                              25

<210> SEQ ID NO 182
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 182 tttatttta ccttcactgt gacct                                               25

<210> SEQ ID NO 183
<211> LENGTH: 25
<212> TYPE: DNA

```
<213> ORGANISM: Artificial Sequence
<220> FEATURE:
<223> OTHER INFORMATION: Synthetic oligonucleotide probe

<400> SEQUENCE: 183
tcccattctc catttgttat ctggg                                              25

<210> SEQ ID NO 184
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 184
ggaaactgaa actactgcac cattt                                              25

<210> SEQ ID NO 185
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 185
gccacaggtc tttatgttga gtcgc                                              25

<210> SEQ ID NO 186
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 186
tcccgacact aactatactc tctac                                              25

<210> SEQ ID NO 187
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 187
actatactct ctactattgg cacag                                              25

<210> SEQ ID NO 188
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 188
gaaggccaat actttggttg ttcct                                              25

<210> SEQ ID NO 189
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 189
actttggttg ttcctttgat ctgac                                              25
```

<210> SEQ ID NO 190
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 190
ggattccagt tttgaacaac acagt                                              25

<210> SEQ ID NO 191
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 191
aaaccatcct tcaatatagt gcctt                                              25

<210> SEQ ID NO 192
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 192
aatatagtgc ctttaacttc ccgtg                                              25

<210> SEQ ID NO 193
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 193
taacttcccg tgtgaaacct gatcc                                              25

<210> SEQ ID NO 194
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 194
aacctgatcc tccacatatt aaaaa                                              25

<210> SEQ ID NO 195
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 195
ctccttccac aatgatgacc tatat                                              25

<210> SEQ ID NO 196
<211> LENGTH: 25
<212> TYPE: DNA
<213> ORGANISM: Artificial Sequence
<220> FEATURE:

```
<223> OTHER INFORMATION: Synthetic oligonucleotide probe

<400> SEQUENCE: 196
gatgacctat atgtgcaatg ggaga                                      25

<210> SEQ ID NO 197
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 197
tttatgttga gtcgcgcacc gaaaa                                      25

<210> SEQ ID NO 198
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 198
gttgagtcgc gcaccgaaaa actaa                                      25

<210> SEQ ID NO 199
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 199
aaaataatgg gcgctttgga gaaga                                      25

<210> SEQ ID NO 200
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 200
cgctttggag aagagtgtgg agtca                                      25

<210> SEQ ID NO 201
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 201
attgaattat aaaagccagc aggct                                      25

<210> SEQ ID NO 202
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 202
agcaggcttc aaactagggg acaaa                                      25
```

<210> SEQ ID NO 203
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 203
aatcttatca agagttgtga caact                                           25

<210> SEQ ID NO 204
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 204
ttgtgacaac ttcctgaggg atcta                                           25

<210> SEQ ID NO 205
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 205
cttcctgagg gatctatact tgctt                                           25

<210> SEQ ID NO 206
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 206
ggatctatac ttgctttgtg ttctt                                           25

<210> SEQ ID NO 207
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 207
gctttgtgtt ctttgtgtca acatg                                           25

<210> SEQ ID NO 208
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 208
ctgggaagca aaacccatgc ctccc                                           25

<210> SEQ ID NO 209
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 209
actgttatcc tatttagatg gccat 25

<210> SEQ ID NO 210
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 210
tgctgacagt catgcagtct gggag 25

<210> SEQ ID NO 211
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 211
ggaagtgatc ttttgttccc atcct 25

<210> SEQ ID NO 212
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 212
acctgtggtg gttgtgatcc ctagg 25

<210> SEQ ID NO 213
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 213
gatccctagg tcttgggagc tcttg 25

<210> SEQ ID NO 214
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 214
gagctcttgg aggtgtctgt atcag 25

<210> SEQ ID NO 215
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 215
aacataccta agcaaaccca gtgtc 25

<210> SEQ ID NO 216
<211> LENGTH: 25

```
<212> TYPE: DNA
<213> ORGANISM: Artificial Sequence
<220> FEATURE:
<223> OTHER INFORMATION: Synthetic oligonucleotide probe

<400> SEQUENCE: 216
gtaattctta ttctttcgtt cagtt                                              25

<210> SEQ ID NO 217
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 217
tcatctgggc actgaaggga tatgt                                              25

<210> SEQ ID NO 218
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 218
tggtagtctt caaccaggga ttgtt                                              25

<210> SEQ ID NO 219
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 219
ccatccagaa tctagcgctg cgcaa                                              25

<210> SEQ ID NO 220
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 220
ccctagcgct ccgagatgca tgtgg                                              25

<210> SEQ ID NO 221
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 221
gtgcctaaag gactgccagc caagc                                              25

<210> SEQ ID NO 222
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 222
```

```
gccaagctca gagtgctcga tctca                                            25

<210> SEQ ID NO 223
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 223
gcaacagact gaacagggcg ccgca                                            25

<210> SEQ ID NO 224
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 224
tgacgagctg cccgaggtgg ataac                                            25

<210> SEQ ID NO 225
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 225
ctgacactgg acgggaatcc cttcc                                            25

<210> SEQ ID NO 226
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 226
acgagggctc aatgaactcc ggcgt                                            25

<210> SEQ ID NO 227
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 227
cccggggctt tgcctaagat ccaag                                            25

<210> SEQ ID NO 228
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 228
gggagtcccg tcaggacgtt gagga                                            25

<210> SEQ ID NO 229
<211> LENGTH: 25
<212> TYPE: DNA
<213> ORGANISM: Artificial Sequence
```

```
<220> FEATURE:
<223> OTHER INFORMATION: Synthetic oligonucleotide probe

<400> SEQUENCE: 229
tgaggacttt tcgaccaatt caacc                                              25

<210> SEQ ID NO 230
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 230
aggacatggg gttccagtac agctg                                              25

<210> SEQ ID NO 231
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 231
gattaccgac cagtgaagct cttac                                              25

<210> SEQ ID NO 232
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 232
tacagtgcgt ggaccacagc accca                                              25

<210> SEQ ID NO 233
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 233
gtgccttaaa gtcggcagca gccgc                                              25

<210> SEQ ID NO 234
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 234
gcagcagccg ctactcaaag aaaag                                              25

<210> SEQ ID NO 235
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 235
gaaaagcccc aagtctttat acaga                                              25
```

<210> SEQ ID NO 236
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 236
gaacaaaggg cgggtcttat cattc                                               25

<210> SEQ ID NO 237
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 237
cttcccggac tcaactgtaa ctgga                                               25

<210> SEQ ID NO 238
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 238
ctggaaactg tgttgctcta accct                                               25

<210> SEQ ID NO 239
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 239
agtcatcatt cgtgttctgt gtata                                               25

<210> SEQ ID NO 240
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 240
gagtcagact gcttgtatat tatca                                               25

<210> SEQ ID NO 241
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 241
atccgaattc tccatatatt cacta                                               25

<210> SEQ ID NO 242
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 242
ggtctgttct tgtagataat gccct 25

<210> SEQ ID NO 243
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 243
tggaatccct ttattgtgct gttgc 25

<210> SEQ ID NO 244
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 244
gtgctgttgc tcttatctgc aaggt 25

<210> SEQ ID NO 245
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 245
tcagcagatt ttgcccacta ttcct 25

<210> SEQ ID NO 246
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 246
cccactattc ctctgagctg aagtt 25

<210> SEQ ID NO 247
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 247
gcttaagctt gaattagatc cctgc 25

<210> SEQ ID NO 248
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 248
gcaaaggctt gctctgtgat gtcag 25

<210> SEQ ID NO 249

```
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 249
atttaccttc atcctgtgca tgttt                                       25

<210> SEQ ID NO 250
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 250
gctttgaggg tcagcctttta ggaag                                      25

<210> SEQ ID NO 251
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 251
gaaggtgcag ctttgttgtc ctttg                                       25

<210> SEQ ID NO 252
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 252
gcatcctctg tagagggact ccacc                                       25

<210> SEQ ID NO 253
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 253
cctgctcaac agcttggctt ccagg                                       25

<210> SEQ ID NO 254
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 254
aagaccaacc acatctggtc tctgc                                       25

<210> SEQ ID NO 255
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 255
```
acctaagcgt catcgtcatt gccat                                          25

<210> SEQ ID NO 256
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 256
atgtggggaa gtgggctgcg gtcac                                          25

<210> SEQ ID NO 257
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 257
cactgtcggc cttgcaaggc cacct                                          25

<210> SEQ ID NO 258
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 258
gcctgtctgt tagccagtgg tggag                                          25

<210> SEQ ID NO 259
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 259
ccatcttccc tgcgatcagg caaaa                                          25

<210> SEQ ID NO 260
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 260
ttcaagttgc tttgtctttt ccatc                                          25

<210> SEQ ID NO 261
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 261
catcctcatc acaagcccctt gtttg                                         25

<210> SEQ ID NO 262
<211> LENGTH: 25
<212> TYPE: DNA

```
<213> ORGANISM: Artificial Sequence
<220> FEATURE:
<223> OTHER INFORMATION: Synthetic oligonucleotide probe

<400> SEQUENCE: 262
tgtttgagtg tcttatccct gagca                                          25

<210> SEQ ID NO 263
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 263
gcctcagggt cacacagggc aaacg                                          25

<210> SEQ ID NO 264
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 264
agggtcacac agggcaaacg acgct                                          25

<210> SEQ ID NO 265
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 265
gtcacacagg gcaaacgacg ctcag                                          25

<210> SEQ ID NO 266
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 266
acacagggca aacgacgctc agact                                          25

<210> SEQ ID NO 267
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 267
acgctcagac tcttggcaca taagt                                          25

<210> SEQ ID NO 268
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 268
actcttggca cataagtctg gagac                                          25
```

-continued

<210> SEQ ID NO 269
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 269
ggcacataag tctggagact gctgt                                              25

<210> SEQ ID NO 270
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 270
cactgtgctc ggaatcatga ttttg                                              25

<210> SEQ ID NO 271
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 271
cggaatcatg attttgggac tgatc                                              25

<210> SEQ ID NO 272
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 272
ggccagcttt ggataatggg agcga                                              25

<210> SEQ ID NO 273
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 273
taatgggagc gaggatgcca tctct                                              25

<210> SEQ ID NO 274
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 274
acagctcccg acgtgagaat atcct                                              25

<210> SEQ ID NO 275
<211> LENGTH: 25
<212> TYPE: DNA
<213> ORGANISM: Artificial Sequence
<220> FEATURE:

-continued

<223> OTHER INFORMATION: Synthetic oligonucleotide probe

<400> SEQUENCE: 275
ttcctcagga tctccaacct gcaga                                              25

<210> SEQ ID NO 276
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 276
ttctgccgag ttgagctgga cacac                                              25

<210> SEQ ID NO 277
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 277
gttgagctgg acacacggag ctcag                                              25

<210> SEQ ID NO 278
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 278
cccttccaaa acacagagga gccat                                              25

<210> SEQ ID NO 279
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 279
gatcccaagc taaatcccaa ggatg                                              25

<210> SEQ ID NO 280
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 280
ggatgacggc atcgtctatg cttcc                                              25

<210> SEQ ID NO 281
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 281
agaacgagac cctgtactct gtctt                                              25

```
<210> SEQ ID NO 282
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 282
gaccctgtac tctgtcttaa aggcc                                          25

<210> SEQ ID NO 283
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 283
aaaggcctaa ccaatggaca gccct                                          25

<210> SEQ ID NO 284
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 284
ctgaatggtg aggccaggta cagtg                                          25

<210> SEQ ID NO 285
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 285
gcaaagcctt taagttttc cactg                                           25

<210> SEQ ID NO 286
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 286
tttccactgg aattctaacc tcacc                                          25

<210> SEQ ID NO 287
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 287
taacctcacc attctgaaaa ccaac                                          25

<210> SEQ ID NO 288
<211> LENGTH: 25
<212> TYPE: DNA
<213> ORGANISM: Artificial Sequence
<220> FEATURE:
<223> OTHER INFORMATION: Synthetic oligonucleotide probe
```

```
<400> SEQUENCE: 288
cacctaccat tgctcaggca tggga                                    25

<210> SEQ ID NO 289
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 289
gaaagcatcg ctacacatca gcagg                                    25

<210> SEQ ID NO 290
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 290
ctccagttac caactcctgt ctggt                                    25

<210> SEQ ID NO 291
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 291
ttcatgtcct tttctatctg gcagt                                    25

<210> SEQ ID NO 292
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 292
gtgaacactg ttctctgggt gacaa                                    25

<210> SEQ ID NO 293
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 293
ccacgtagca gcggctcagt tggtg                                    25

<210> SEQ ID NO 294
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 294
tcagttggtg gccatcgatc tggac                                    25

<210> SEQ ID NO 295
<211> LENGTH: 25
```

```
<212> TYPE: DNA
<213> ORGANISM: Artificial Sequence
<220> FEATURE:
<223> OTHER INFORMATION: Synthetic oligonucleotide probe

<400> SEQUENCE: 295
ctccccatga gcactgcgta caaac                                               25

<210> SEQ ID NO 296
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 296
tgaaaaagtt ctgtgctcag ccttg                                               25

<210> SEQ ID NO 297
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 297
gaatactgct tttctggtac ctaca                                               25

<210> SEQ ID NO 298
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 298
ccttctgcaa ggctatcatt tcaca                                               25

<210> SEQ ID NO 299
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 299
gggagcacat ccatttcatt ggcaa                                               25

<210> SEQ ID NO 300
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 300
cattggcaag atccagggca gcgac                                               25

<210> SEQ ID NO 301
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 301
``` gctggactttt gggctacatg ctgaa 25

<210> SEQ ID NO 302
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 302
tgatcccagc tgagcaacca ttgtc 25

<210> SEQ ID NO 303
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 303
gccatcatag gcttgcttat ctttc 25

<210> SEQ ID NO 304
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 304
ctttcacaag ccttcatatt tctgg 25

<210> SEQ ID NO 305
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 305
aaaatcgtcc agggagcatt ttcct 25

<210> SEQ ID NO 306
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 306
tccatcgcag tgttcaaggc catcc 25

<210> SEQ ID NO 307
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 307
ttaaagccaa gccacatctt atttt 25

<210> SEQ ID NO 308
<211> LENGTH: 25
<212> TYPE: DNA
<213> ORGANISM: Artificial Sequence

```
<220> FEATURE:
<223> OTHER INFORMATION: Synthetic oligonucleotide probe

<400> SEQUENCE: 308
gtggagtggc atgcttttgc cctat                                          25

<210> SEQ ID NO 309
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 309
gcttttgccc tatcgtggaa tttac                                          25

<210> SEQ ID NO 310
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 310
gggctttgtt tgcttattcc atgaa                                          25

<210> SEQ ID NO 311
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 311
gcagcagcta tagaccttac catgg                                          25

<210> SEQ ID NO 312
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 312
ggattgctgc aagagttacc tgttg                                          25

<210> SEQ ID NO 313
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 313
gtgatgtttc attctgacct tgtcc                                          25

<210> SEQ ID NO 314
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 314
gctctccatc tctagatctg gggac                                          25
```

```
<210> SEQ ID NO 315
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 315
atctggggac tgactgttga gctga                                             25

<210> SEQ ID NO 316
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 316
aagctctcac acaaaccgga agcca                                             25

<210> SEQ ID NO 317
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 317
aatgtcccct atctcttgaa tgatc                                             25

<210> SEQ ID NO 318
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 318
gaatactgct tttctggtac ctaca                                             25

<210> SEQ ID NO 319
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 319
gattcctggg agcacatcca tttca                                             25

<210> SEQ ID NO 320
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 320
ggactttggg ctacatgctg aacct                                             25

<210> SEQ ID NO 321
<211> LENGTH: 25
<212> TYPE: DNA
<213> ORGANISM: Artificial Sequence
<220> FEATURE:
<223> OTHER INFORMATION: Synthetic oligonucleotide probe
```

```
<400> SEQUENCE: 321
tgaacctgac caacatgatc ccagc                                          25

<210> SEQ ID NO 322
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 322
tgatcccagc tgagcaacca ttgtc                                          25

<210> SEQ ID NO 323
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 323
acctatgtct tcctcatggt tctat                                          25

<210> SEQ ID NO 324
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 324
gccatcatag gcttgcttat ctttc                                          25

<210> SEQ ID NO 325
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 325
aaatcgtcca gggagcattt tcctc                                          25

<210> SEQ ID NO 326
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 326
tccatcgcag tgttcaaggc catcc                                          25

<210> SEQ ID NO 327
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 327
gtgaagcttc cttggctttt actga                                          25

<210> SEQ ID NO 328
```

```
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 328
ggtattcaat atcctttgcc tcaag                                           25

<210> SEQ ID NO 329
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 329
aaccaatttg tgttgttctg attca                                           25

<210> SEQ ID NO 330
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 330
ttggtttctg ggtggccaat tcaga                                           25

<210> SEQ ID NO 331
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 331
aacagtctcc aggaccatca gtata                                           25

<210> SEQ ID NO 332
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 332
gtatactgca tttcatgtgc accaa                                           25

<210> SEQ ID NO 333
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 333
gtcactgatc ctgcaaatgg acatc                                           25

<210> SEQ ID NO 334
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 334
```

```
atggacatca ttttagcaca ctagc                                          25

<210> SEQ ID NO 335
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 335
agcacactag cggtttatat tttaa                                          25

<210> SEQ ID NO 336
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 336
tttaaggacc ttcattctct gttct                                          25

<210> SEQ ID NO 337
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 337
cagttgcaac ttacgcttgg catct                                          25

<210> SEQ ID NO 338
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 338
gcttggcatc ttcagaatgc ttttc                                          25

<210> SEQ ID NO 339
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 339
tttttgctgt cataatcgcc tcata                                          25

<210> SEQ ID NO 340
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 340
aactggattc actttacaat ttgca                                          25

<210> SEQ ID NO 341
<211> LENGTH: 25
<212> TYPE: DNA
```

```
<213> ORGANISM: Artificial Sequence
<220> FEATURE:
<223> OTHER INFORMATION: Synthetic oligonucleotide probe

<400> SEQUENCE: 341
gcaaaacggc tgcaggtcaa cctat                                          25

<210> SEQ ID NO 342
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 342
gtcaacctat tggtcaagcc atcag                                          25

<210> SEQ ID NO 343
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 343
ggaactatat tgtgcctatt ctttg                                          25

<210> SEQ ID NO 344
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 344
gtgcctattc tttggcttaa tgaga                                          25

<210> SEQ ID NO 345
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 345
aatgagactg ggaccattgg tgatg                                          25

<210> SEQ ID NO 346
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 346
tggaaaaata aacctccttg gcctg                                          25

<210> SEQ ID NO 347
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 347
cctccttggc ctgatagaaa tgatc                                          25
```

```
<210> SEQ ID NO 348
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 348
gatcttactc agtgttggtg tggtg                                   25

<210> SEQ ID NO 349
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 349
ttggtgtggt gatgtttgtt gcttt                                   25

<210> SEQ ID NO 350
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 350
gatttcatat tgtgcatgca gatcg                                   25

<210> SEQ ID NO 351
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 351
agccttgctc aggtgcaagt gcccc                                   25

<210> SEQ ID NO 352
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 352 caggggggcgg ggtgcagaag aatcc                                  25

<210> SEQ ID NO 353
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 353
agaatccgag tgtttgccag gctta                                   25

<210> SEQ ID NO 354
<211> LENGTH: 25
<212> TYPE: DNA
<213> ORGANISM: Artificial Sequence
<220> FEATURE:
```

-continued

```
<223> OTHER INFORMATION: Synthetic oligonucleotide probe

<400> SEQUENCE: 354
acaaactgat ttctcacggc gtgtc                                              25

<210> SEQ ID NO 355
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 355
ggcgcaagcc tcactattac ttgaa                                              25

<210> SEQ ID NO 356
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 356
aagcaattat attgtcctcc cctat                                              25

<210> SEQ ID NO 357
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 357
gacgtgaatg tctcagcgag gtgta                                              25

<210> SEQ ID NO 358
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 358
gaggtgtaaa gttgttcgcc gcgtg                                              25

<210> SEQ ID NO 359
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 359
cgccgcgtgg aatgtgagtg tgttt                                              25

<210> SEQ ID NO 360
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 360
agaaagactg attacctcct gtgtg                                              25
```

```
<210> SEQ ID NO 361
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 361
ggaaacaccg agtctctgta taatc                                            25

<210> SEQ ID NO 362
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 362
gcaataactc tgggaggggc tcgag                                            25

<210> SEQ ID NO 363
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 363
gctcgagagg gctggtcctt attta                                            25

<210> SEQ ID NO 364
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 364
gagttcctct gggtttctaa gcagt                                            25

<210> SEQ ID NO 365
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 365
agcgtcaaga catttgctga actca                                            25

<210> SEQ ID NO 366
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 366
tgaactcagc acattcggga ccaat                                            25

<210> SEQ ID NO 367
<211> LENGTH: 25
<212> TYPE: DNA
<213> ORGANISM: Artificial Sequence
<220> FEATURE:
<223> OTHER INFORMATION: Synthetic oligonucleotide probe
```

```
<400> SEQUENCE: 367
gtgggtacat caagtccatc tgaca                                           25

<210> SEQ ID NO 368
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 368
gactcagtgt gtgatccggt ttctt                                           25

<210> SEQ ID NO 369
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 369
tgtagaatct cttcatgctt gacat                                           25

<210> SEQ ID NO 370
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 370
cagtattatt cccgacgaca catat                                           25

<210> SEQ ID NO 371
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 371
taggtgtctg ccttcacaaa tgtca                                           25

<210> SEQ ID NO 372
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 372
caaatgtcat tgtctactcc tagaa                                           25

<210> SEQ ID NO 373
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 373
ggcagtcggg ggaaccgcga agaag                                           25

<210> SEQ ID NO 374
<211> LENGTH: 25
```

```
<212> TYPE: DNA
<213> ORGANISM: Artificial Sequence
<220> FEATURE:
<223> OTHER INFORMATION: Synthetic oligonucleotide probe

<400> SEQUENCE: 374
gaaccgcgaa gaagccgagg agccc                                        25

<210> SEQ ID NO 375
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 375
cgaagaagcc gaggagcccg gagcc                                        25

<210> SEQ ID NO 376
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 376
tctctcagtc caaaagcggc ttttg                                        25

<210> SEQ ID NO 377
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 377
ggcttttggt tcggcgcaga gagac                                        25

<210> SEQ ID NO 378
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 378
gcagagagac ccgggggtct agctt                                        25

<210> SEQ ID NO 379
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 379
tagcttttcc tcgaaaagcg ccgcc                                        25

<210> SEQ ID NO 380
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 380
```

-continued ccttggcccc gagaacagac aaaga					25

<210> SEQ ID NO 381
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 381
aacagacaaa gagcaccgca gggcc					25

<210> SEQ ID NO 382
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 382
ctgaggccgg ccatggtcat ggaag					25

<210> SEQ ID NO 383
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 383
tcatggaagt gggcaccctg gacgc					25

<210> SEQ ID NO 384
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 384
agcagggatt ggggtcacac ccttc					25

<210> SEQ ID NO 385
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 385
ataacgccac caatctgaag ctcaa					25

<210> SEQ ID NO 386
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 386
aaagatctac ttctactggc tgtgc					25

<210> SEQ ID NO 387
<211> LENGTH: 25
<212> TYPE: DNA
<213> ORGANISM: Artificial Sequence

```
<220> FEATURE:
<223> OTHER INFORMATION: Synthetic oligonucleotide probe

<400> SEQUENCE: 387
ccgggacaca catgcctttg agtgg                                              25

<210> SEQ ID NO 388
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 388
gcctttgagt ggtttgcaga tctgc                                              25

<210> SEQ ID NO 389
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 389
aaaggaacaa tgccggcttc ctcag                                              25

<210> SEQ ID NO 390
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 390
tcagctacaa catctacctc actgg                                              25

<210> SEQ ID NO 391
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 391
cactggctgg gatgagtctc aggcc                                              25

<210> SEQ ID NO 392
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 392
gtctcaggcc aatcactttg ctgtg                                              25

<210> SEQ ID NO 393
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 393
gactttgtat ggacggccca actgg                                              25
```

-continued

<210> SEQ ID NO 394
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 394
gcaagtcaac accctaatac cagaa                                              25

<210> SEQ ID NO 395
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 395
gattggaatg cctggctcta ctctc                                              25

<210> SEQ ID NO 396
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 396
gccacagacc tgaaggatct ctctt                                              25

<210> SEQ ID NO 397
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 397
ggatctctct tctcatcaat tgaat                                              25

<210> SEQ ID NO 398
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 398
gagtttttag cacagacgct ccaga                                              25

<210> SEQ ID NO 399
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 399
tgggaggacg caattccttt ggcgc                                              25

<210> SEQ ID NO 400
<211> LENGTH: 25
<212> TYPE: DNA
<213> ORGANISM: Artificial Sequence
<220> FEATURE:
<223> OTHER INFORMATION: Synthetic oligonucleotide probe

```
<400> SEQUENCE: 400
ggcccttatt caaggatctt gctgc                                              25

<210> SEQ ID NO 401
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 401
ttgctgcctt tgacaaatcc catga                                              25

<210> SEQ ID NO 402
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 402
aaatcccatg atcaagctgt ccgaa                                              25

<210> SEQ ID NO 403
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 403
gtccgaacct accaagagca caaag                                              25

<210> SEQ ID NO 404
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 404
caaagcaagc atgcatcccg tgact                                              25

<210> SEQ ID NO 405
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 405
catcccgtga ctgcaatgct ggtgg                                              25

<210> SEQ ID NO 406
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 406
agcatcggag ccattcattc ggaga                                              25

<210> SEQ ID NO 407
```

```
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 407
gcacctgagt catgtgtatt cccgg                                              25

<210> SEQ ID NO 408
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 408
cgacaggctt gtctgtttac tagct                                              25

<210> SEQ ID NO 409
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 409
tggccttgga cgggtggctg acatc                                              25

<210> SEQ ID NO 410
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 410
tgaggaatcg ggtggccggg caagc                                              25

<210> SEQ ID NO 411
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 411
ctgcctcaat acccacaaaa gacca                                              25

<210> SEQ ID NO 412
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 412
aagaccattc ccagtataca taagc                                              25

<210> SEQ ID NO 413
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 413
```

```
gtatttatca cttggacatc tgttt                                              25

<210> SEQ ID NO 414
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 414
agaatcctag gcagtggctc attgt                                              25

<210> SEQ ID NO 415
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 415
ggagtttcat ggggttcagc ctaac                                              25

<210> SEQ ID NO 416
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 416
acagtcctta taaaccattg gcatg                                              25

<210> SEQ ID NO 417
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 417
tccagcccga cacggaggac tgagg                                              25

<210> SEQ ID NO 418
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 418
cacggaggac tgaggtcgcc gggac                                              25

<210> SEQ ID NO 419
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 419
gccccaggct cgtggactga gtggg                                              25

<210> SEQ ID NO 420
<211> LENGTH: 25
<212> TYPE: DNA
```

```
<213> ORGANISM: Artificial Sequence
<220> FEATURE:
<223> OTHER INFORMATION: Synthetic oligonucleotide probe

<400> SEQUENCE: 420
ccttgtggca gcaacggcac agcta                                              25

<210> SEQ ID NO 421
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 421
cggcacagct aattctactc acagt                                              25

<210> SEQ ID NO 422
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 422
gtccgtggga cgggatggtt ctggc                                              25

<210> SEQ ID NO 423
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 423
ggttctggct gtttgagatt ctcaa                                              25

<210> SEQ ID NO 424
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 424
caaaggagcg agcatgtcgt ggaca                                              25

<210> SEQ ID NO 425
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 425
ggacacacac agactatttt tagat                                              25

<210> SEQ ID NO 426
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 426
ttgccttttg caaccaggaa cagca                                              25
```

```
<210> SEQ ID NO 427
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 427
ttctcagaat cccttaacag ttgta                                   25

<210> SEQ ID NO 428
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 428
gccaaactga tcatccagca gtgtc                                   25

<210> SEQ ID NO 429
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 429
tccgagtcct ctcatttttc aagac                                   25

<210> SEQ ID NO 430
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 430
atttctttca agcactggac aacat                                   25

<210> SEQ ID NO 431
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 431
ttggacatct ccaggcattt cacag                                   25

<210> SEQ ID NO 432
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 432
gagtgtatca aagctcaggc cacaa                                   25

<210> SEQ ID NO 433
<211> LENGTH: 25
<212> TYPE: DNA
<213> ORGANISM: Artificial Sequence
<220> FEATURE:
```

-continued

<223> OTHER INFORMATION: Synthetic oligonucleotide probe

<400> SEQUENCE: 433
ctcaggccac aacagtcaag tcttt                                          25

<210> SEQ ID NO 434
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 434
tgtgtgttac gactaccaag gctca                                          25

<210> SEQ ID NO 435
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 435
gttggctctt ggatgcagat gatat                                          25

<210> SEQ ID NO 436
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 436
aagacatcct caatctaagt actta                                          25

<210> SEQ ID NO 437
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 437
aagtacttaa ctattctcca gaaat                                          25

<210> SEQ ID NO 438
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 438
gccgttctct ccaatcattc agaaa                                          25

<210> SEQ ID NO 439
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 439
aagcggcgca accaggagat gcagc                                          25

```
<210> SEQ ID NO 440
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 440
ggacagcaga ctgccggtaa cgcgc                                              25

<210> SEQ ID NO 441
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 441
gggcgggaga gactcagcaa cgacc                                              25

<210> SEQ ID NO 442
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 442
tgcccgctgc agtttcttgg gacat                                              25

<210> SEQ ID NO 443
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 443
gcagtttctt gggacatagg agcgc                                              25

<210> SEQ ID NO 444
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 444
agaagctaca gcctggactt accac                                              25

<210> SEQ ID NO 445
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 445
acttaccacc actaaactgc gagag                                              25

<210> SEQ ID NO 446
<211> LENGTH: 25
<212> TYPE: DNA
<213> ORGANISM: Artificial Sequence
<220> FEATURE:
<223> OTHER INFORMATION: Synthetic oligonucleotide probe
```

```
<400> SEQUENCE: 446
ggtagctttt tctacatctt actcc                                         25

<210> SEQ ID NO 447
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 447
atcttactcc tgttgatgca gctaa                                         25

<210> SEQ ID NO 448
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 448
ccagactttt cagacaaacc ctttg                                         25

<210> SEQ ID NO 449
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 449
gagcatgctc acttttttat attaa                                         25

<210> SEQ ID NO 450
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 450
ttcaaaagtg ctccagaaag gccgg                                         25

<210> SEQ ID NO 451
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 451
gtgctccaga aaggccggaa tagtc                                         25

<210> SEQ ID NO 452
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 452
gaaaggccgg aatagtcatg tagtg                                         25

<210> SEQ ID NO 453
<211> LENGTH: 25
```

```
<212> TYPE: DNA
<213> ORGANISM: Artificial Sequence
<220> FEATURE:
<223> OTHER INFORMATION: Synthetic oligonucleotide probe

<400> SEQUENCE: 453
aggccggaat agtcatgtag tggat                                    25

<210> SEQ ID NO 454
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 454
gcagtgcttt aagatttaat tagtc                                    25

<210> SEQ ID NO 455
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 455
gatttaatta gtcacggctg ctacg                                    25

<210> SEQ ID NO 456
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 456
acggctgcta cgtgtatctg atgta                                    25

<210> SEQ ID NO 457
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 457
gtatctgatg tagttaacca tggcc                                    25

<210> SEQ ID NO 458
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 458
gatgtagtta accatggcct gtcat                                    25

<210> SEQ ID NO 459
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 459
```

-continued

```
gttaaccatg gcctgtcatg attat                                          25

<210> SEQ ID NO 460
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 460
ggcctgtcat gattatattg ctata                                          25
```